United States Patent
Zhan et al.

(10) Patent No.: US 11,598,774 B2
(45) Date of Patent: Mar. 7, 2023

(54) METHODS OF DIAGNOSIS AND TREATMENT OF ALZHEIMER'S DISEASE

(71) Applicant: The Regents of the University of California, Oakland, CA (US)

(72) Inventors: Xinhua Zhan, Vacaville, CA (US); Boryana S. Stamova-Kiossepacheva, Davis, CA (US); Frank R. Sharp, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 671 days.

(21) Appl. No.: 16/392,182

(22) Filed: Apr. 23, 2019

(65) Prior Publication Data

US 2020/0088724 A1  Mar. 19, 2020

Related U.S. Application Data

(63) Continuation of application No. PCT/US2017/058039, filed on Oct. 24, 2017.

(60) Provisional application No. 62/412,684, filed on Oct. 25, 2016.

(51) Int. Cl.
*G01N 33/569* (2006.01)
*C12Q 1/689* (2018.01)
*G01N 33/68* (2006.01)

(52) U.S. Cl.
CPC ....... *G01N 33/56916* (2013.01); *C12Q 1/689* (2013.01); *G01N 33/6896* (2013.01); *C12Q 2600/158* (2013.01); *G01N 2333/245* (2013.01); *G01N 2800/2821* (2013.01)

(58) Field of Classification Search
CPC ....... G01N 33/56916; G01N 2333/245; G01N 2800/2821; G01N 33/6896
See application file for complete search history.

(56) References Cited

U.S. PATENT DOCUMENTS

| 6,531,131 | B1 | 3/2003 | Gu et al. |
| 2002/0091074 | A1 | 7/2002 | Wooley et al. |
| 2009/0238840 | A1 | 9/2009 | Pfeifer et al. |

FOREIGN PATENT DOCUMENTS

WO  2018/081085 A1  5/2018

OTHER PUBLICATIONS

Stein et al. Serum antibodies to periodontal pathogens are a risk factor for Alzheimer's disease. Alzheimers Dement. May 2012; 8(3): 196-203.*
Schofield et al. The Role of Olfactory Challenge Tests in Incipient Dementia and Clinical Trial Design. Current Neurology and Neuroscience Reports vol. 14: 479 (2014).*
Miklossy, J. Historic evidence to support a causal relationship between spirochetal infections and Alzheimer's disease. Front Aging Neurosci. Apr. 16, 2015;7:46.*
Ghanem et al. Sexually Transmitted Diseases. From Encyclopedia of Microbiology. 4th Edition. Academic Press. 2019.*
Jaiswal et al. The pan-genome of Treponema pallidum reveals differences in genome plasticity between subspecies related to venereal and non-venereal syphilis. BMC Genomics 21, 33 (2020). https://doi.org/10.1186/s12864-019-6430-6.*
Kubanov et al. Novel Treponema pallidum Recombinant Antigens for Syphilis Diagnostics: Current Status and Future Prospects, BioMed Research International, vol. 2017, Article ID 1436080, 12 pages, 2017. https://doi.org/10.1155/2017/1436080.*
Bartzokis et al., Heterogeneous Age-Related Breakdown of White Matter Structural Integrity Implications for Cortical "Disconnection" in Aging and Alzheimer's Disease, Neurobiology of Aging, vol. 25, No. 7, Aug. 2004, pp. 843-851.
Bibi et al., Link Between Chronic Bacterial Inflammation and Alzheimer Disease, CNS & Neurological Disorders - Drug Targets, vol. 13, No. 7, Sep. 2014, pp. 1140-1147.
Braak et al., Frequency of Stages of Alzheimer-Related Lesions in Different Age Categories, Neurobiology of Aging, vol. 18, No. 4, July-Aug. 1997, pp. 351-357.
Branton et al., Brain Microbial Populations in HIV/AIDS: a-Proteobacteria Predominate Independent of Host Immune Status, PLoS One, vol. 8, Issue 1, Jan. 2013, 16 pages.
Bu et al., A Study on the Association Between Infectious Burden and Alzheimer's Disease, European Journal of Neurology, vol. 22, No. 12, 2015, pp. 1519-1525.
Chapman et al., Role of Escherichia coli Curli Operons in Directing Amyloid Fiber Formation, Science, vol. 295, No. 5556, Feb. 1, 2002, pp. 851-855.
Civitelli et al., Herpes Simplex Virus Type 1 Infection in Neurons Leads to Production and Nuclear Localization of App Intracellular Domain (AICD): Implications for Alzheimer's Disease Pathogenesis, J. Neurovirol., vol. 21, No. 5, Oct. 2015, pp. 480-490.
Debroy et al., Detection of O antigens in *Escherichia coli*, Animal Health Research Reviews, vol. 12, No. 2, Dec. 2011, pp. 169-185.
Dunn et al., Association between Dementia and Infectious Disease *Evidence from a Case-Control Study*, Alzheimer Dis Assoc. Disord., vol. 19, No. 2, Apr.-Jun. 2005, pp. 91-94.
Engelhart et al., Inflammatory Proteins in Plasma and the Risk of Dementia, Arch Neurol., vol. 61, No. 5, May 2004, pp. 668-672.
Erickson et al., Lipopolysaccharide Impairs Amyloid Beta Efflux from Brain: Altered Vascular Sequestration, Cerebrospinal Fluid Reabsorption, Peripheral Clearance and Transporter Function at the Blood-brain Barrier, Journal of Neuroinflammation, vol. 9, No. 150, Jun. 2012, 15 pages.

(Continued)

*Primary Examiner* — Gregory S Emch
(74) *Attorney, Agent, or Firm* — Kilpatrick Townsend & Stockton LLP

(57) ABSTRACT

Provided are methods of mitigating, reversing or eliminating in a subject one or more symptoms associated with cognitive impairment associated with amyloid deposits in the brain (e.g., olfactory dysfunction as a risk factor of dementia, mild cognitive impairment, Alzheimer's Disease) by detecting and targeting gram negative bacteria in the brain.

21 Claims, 26 Drawing Sheets

Specification includes a Sequence Listing.

(56) References Cited

OTHER PUBLICATIONS

Fowler et al., Functional amyloid—from bacteria to humans, Trends in Biochemical Sciences, vol. 32, No. 5, May 2007, pp. 217-224.
Holmes et al., Systemic Inflammation and Alzheimer's Disease, Biochemical Society Transactions, vol. 39, No. 4, Aug. 2011, pp. 898-901.
Imbimbo, B., An Update on the Efficacy of Non-Steroidal Anti-Inflammatory Drugs in Alzheimer's Disease, Expert Opinion on Investigational Drugs, vol. 18, No. 8, Aug. 2009, pp. 1147-11468.
Janota et al., Dissecting the Contribution of Vascular Alterations and Aging to Alzheimer's Disease, Mol. Neurobiol., vol. 53, No. 6, Aug. 2016, pp. 3793-3811.
Khan et al., Peripheral Biomarkers of Alzheimer's Disease, Journal of Alzheimer's Disease, vol. 44, No. 3, 2015, pp. 729-744.
Klemm et al., Bacterial Adhesins: Function and Structure, Int. J. Med. Microbiol., vol. 290, No. 1, Mar. 2000, pp. 27-35.
Kountouras et al., Eradication of Helicobacter Pylori May Be Beneficial in the Management of Alzheimer's Disease, Journal of Neurology, vol. 256. No. 5, May 2009, pp. 758-767.
Mawanda et al., Can Infections Cause Alzheimer's Disease?, Epidemiologic Reviews, vol. 35, Issue 1, Jan. 1, 2013, pp. 161-180.
Nagy et al., Enterotoxigenic *Escherichia coli* (ETEC) in Farm Animals, Veterinary Research, vol. 30, No. 2-3, Mar.-Jun. 1999, pp. 259-284.
Noble et al., Serum IgG Antibody Levels to Periodontal Microbiota are Associated with Incident Alzheimer Disease, PLoS One, vol. 9, No. 12, Dec. 18, 2014, 14 pages.
Quinones et al., O-antigen and Virulence Profiling of Shiga Toxin-producing *Escherichia coli* by a Rapid and Cost-effective DNA Microarray Colorimetric Method, Frontier in Cell Infection Microbiology, vol. 2, No. 61, May 11, 2012, 10 pages.
Schmidt et al., Early Inflammation and Dementia: A 25-Year Follow-up of the Honolulu-Asia Aging Study, Annals of Neurology, vol. 52, No. 2, Aug. 2002, pp. 168-174.
Schmidt et al., Thinking from the Gut: The Microbiome May Yield a New Class of Psychobiotics for the Treatment of Anxiety, Depression and Other Mood Disorders, Nature, vol. 518, Issue 7540, Feb. 26, 2015, pp. S13-S15.
Schrijver et al., Bacterial Peptidoglycan and Immune Reactivity in the Central Nervous System in Multiple Sclerosis, Brain, vol. 124, No. 8, Aug. 2001, pp. 1544-1554.
Singhrao et al., Porphyromonas Gingivalis Periodontal Infection and its Putative Links with Alzheimer's Disease, Mediators of Inflammation, 2015, pp. 1-10.
Tyas et al., Risk Factors for Alzheimer's Disease: A Population-Based, Longitudinal Study in Manitoba, Canada, International Journal of Epidemiology, vol. 30, No. 3, Jun. 2001, pp. 590-597.
Verreault et al., Past Exposure to Vaccines and Subsequent Risk of Alzheimer's Disease, Canadian Medical Association Journal, vol. 165, No. 11, Nov. 27, 2001, pp. 1495-1498.
Visser et al., Phagocytes Containing a Disease-Promoting Toll-Like Receptor/Nod Ligand are Present in the Brain During Demyelinating Disease in Primates, The American Journal of Pathology, vol. 169, No. 5, Nov. 2006, pp. 1671-1685.
Vlad et al., Protective Effects of NSAIDs on the Development of Alzheimer Disease, Neurology, vol. 70, No. 19, May 6, 2008, 1672-1677.
Walker et al., Etiology of Diarrhea in Older Children, Adolescents and Adults: A Systematic Review, PLoS Neglected Tropical Diseases, vol. 4, Issue 8, Aug. 3, 2010, 8 pages.
Zhan et al., Gram-Negative Bacterial Molecules Associate with Alzheimer Disease Pathology, Neurology, vol. 87, No. 22, Nov. 29, 2016, pp. 2324-2332.
Zhan et al., Inflammation Combined with Ischemia Produces Myelin Injury and Plaque-Like Aggregates of Myelin, Amyloid-β and AβPP in Adult Rat Brain, Journal of Alzheimer's Disease, vol. 46, No. 2, 2015, pp. 507-523.
Zhan et al., Myelin Basic Protein Associates with AβPP, Aβ$_{1-42}$, and Amyloid Plaques in Cortex of Alzheimer's Disease Brain, Journal of Alzheimer's Disease, vol. 44, No. 4, 2015, pp. 1213-1229.
Zhan et al., Myelin Injury and Degraded Myelin Vesicles in Alzheimer's Disease, Current Alzheimer Research, vol. 11, No. 3, Mar. 2014, pp. 232-238.

\* cited by examiner

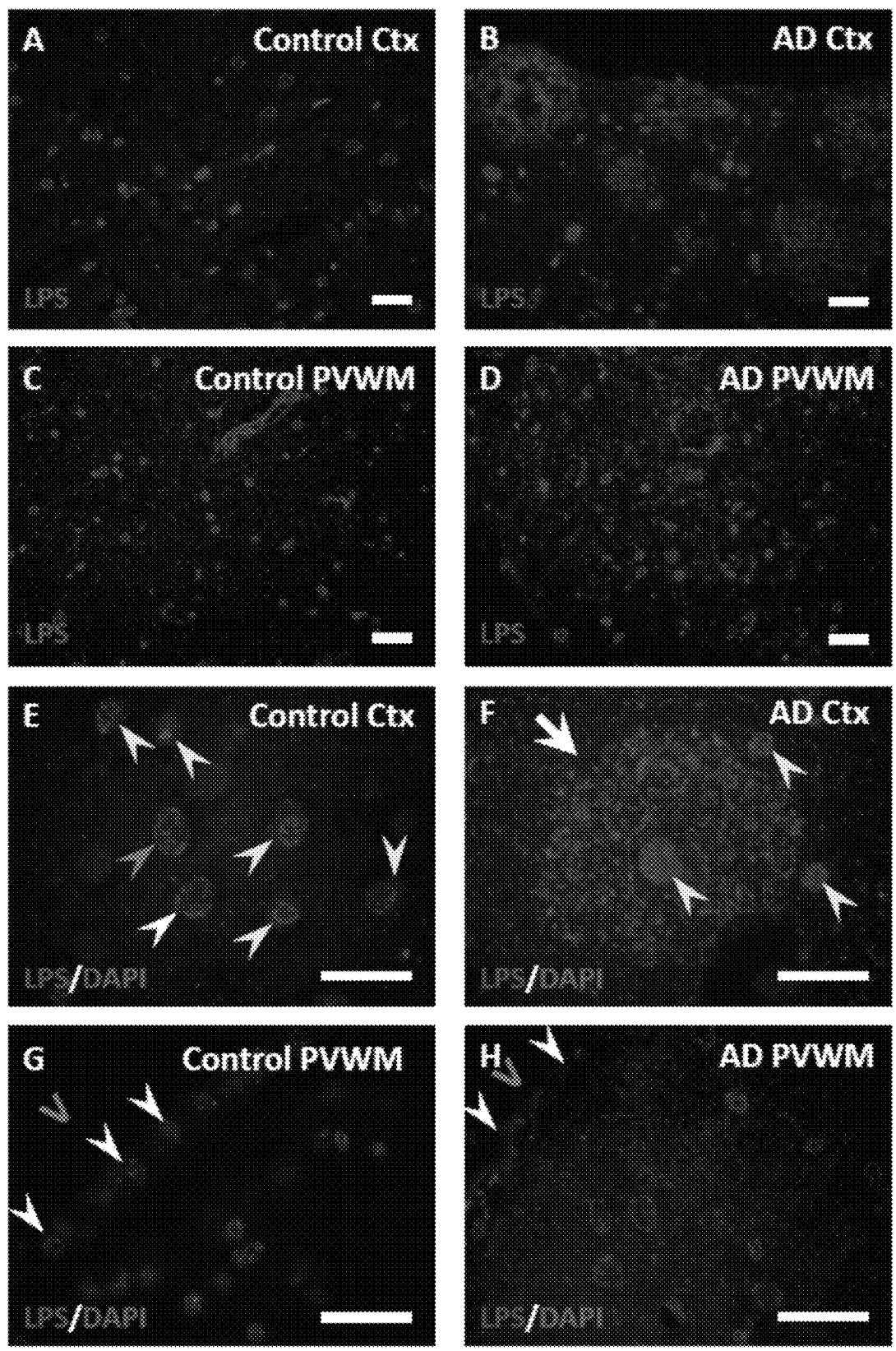
Fig. 3A-H

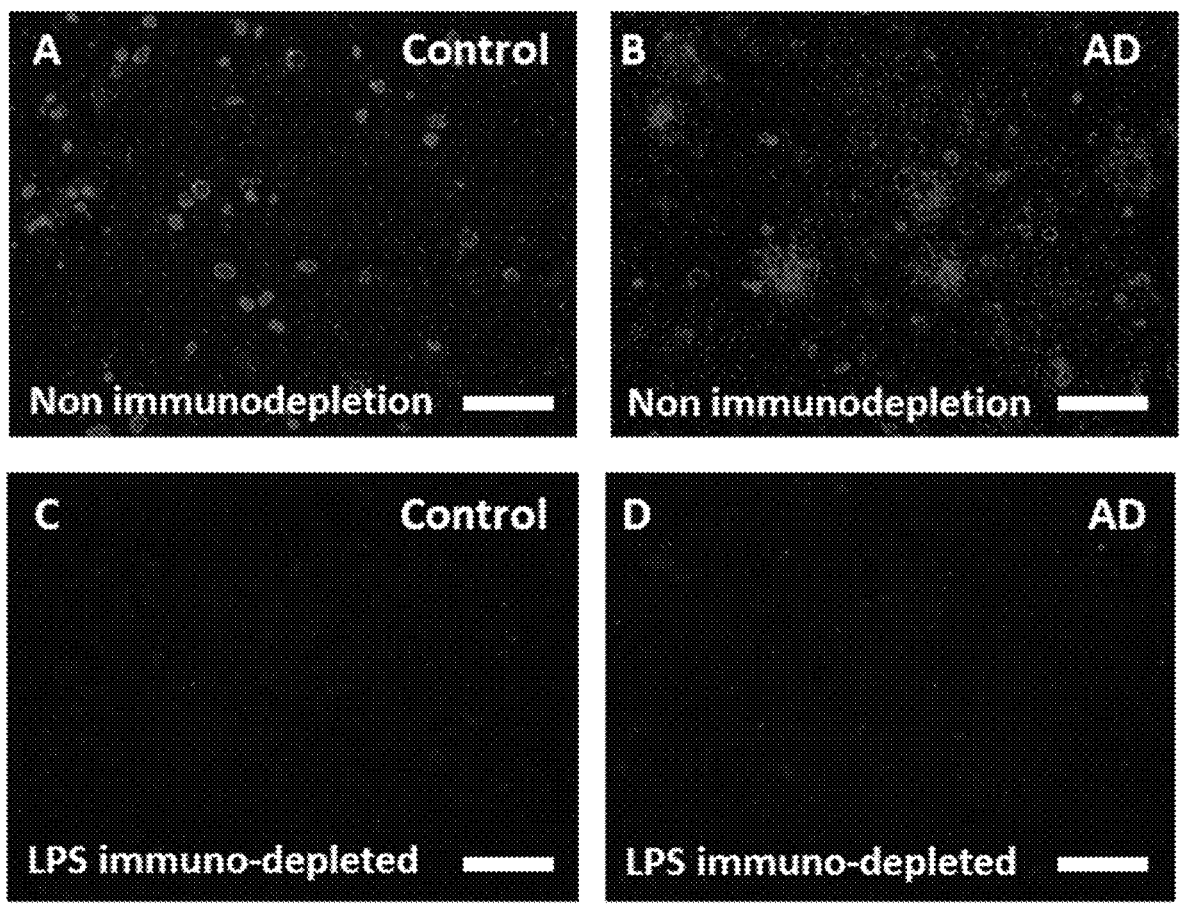
Fig. 4A-D

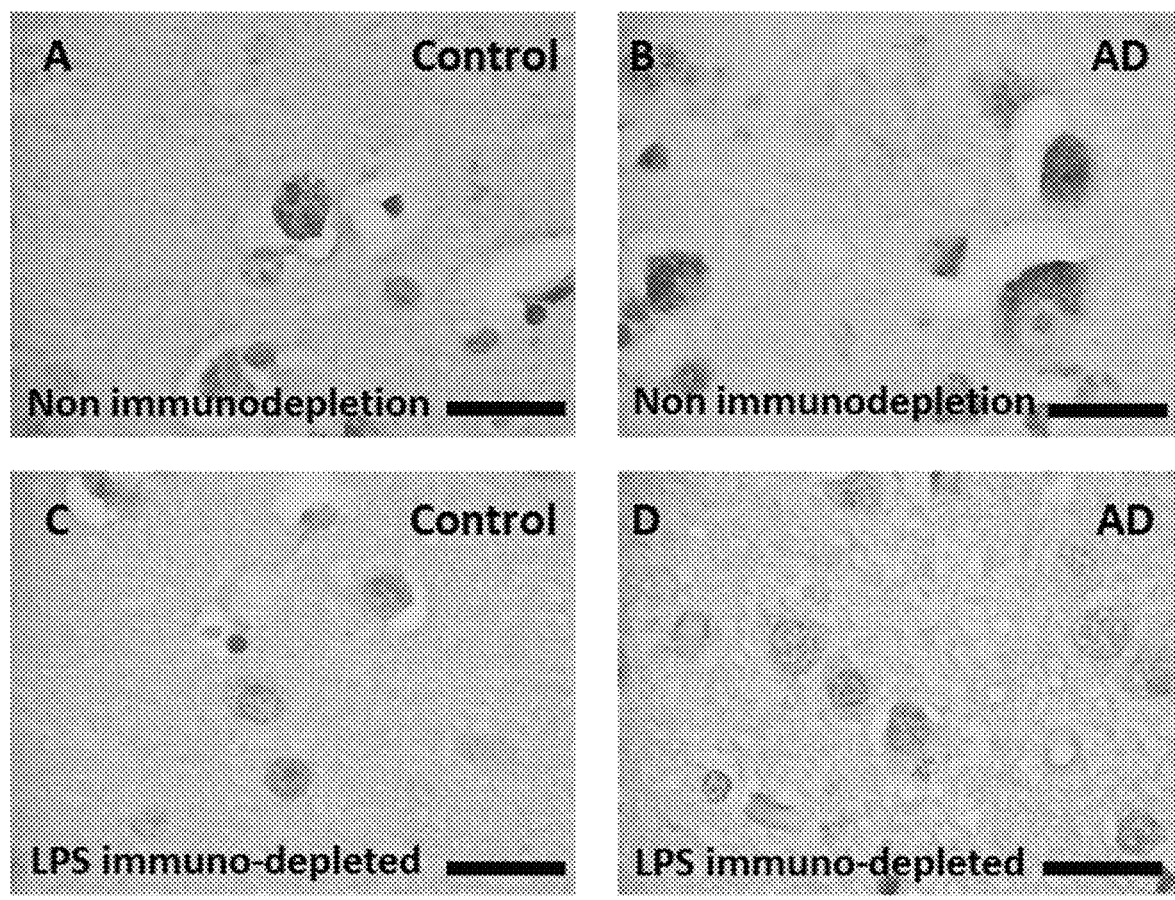
Fig. 5A-D

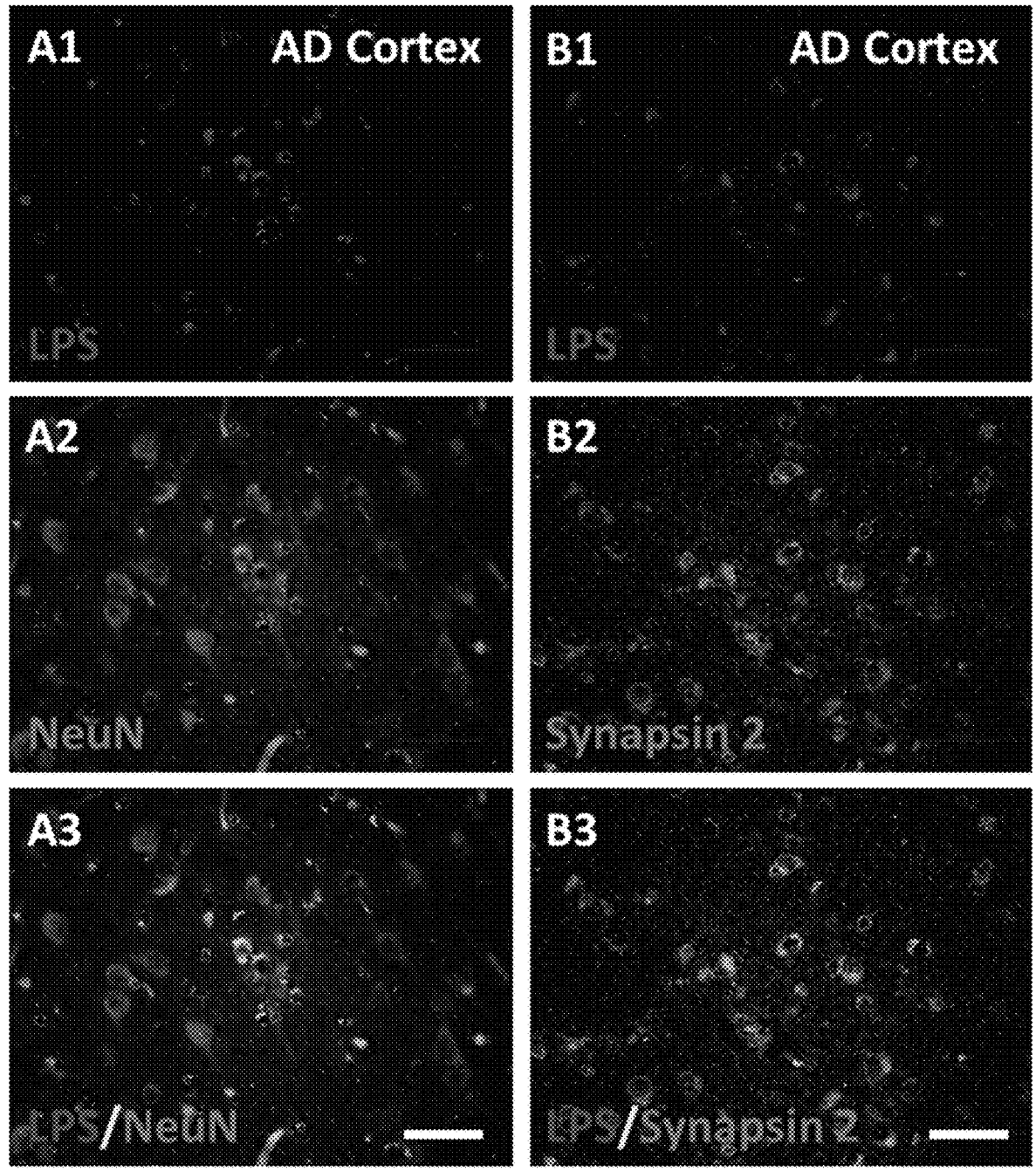
Fig. 6A1-B3

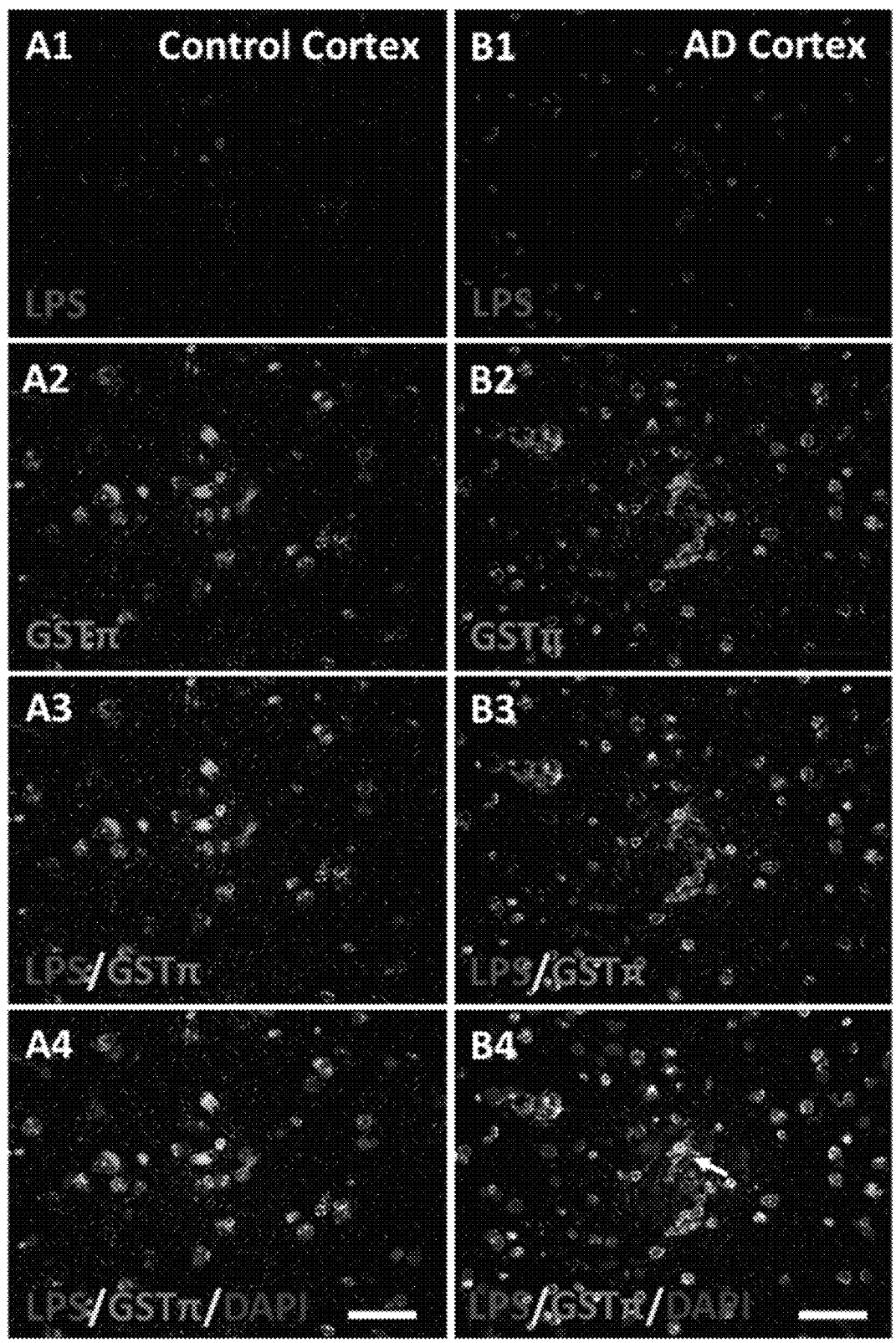
Fig. 7A1-B4

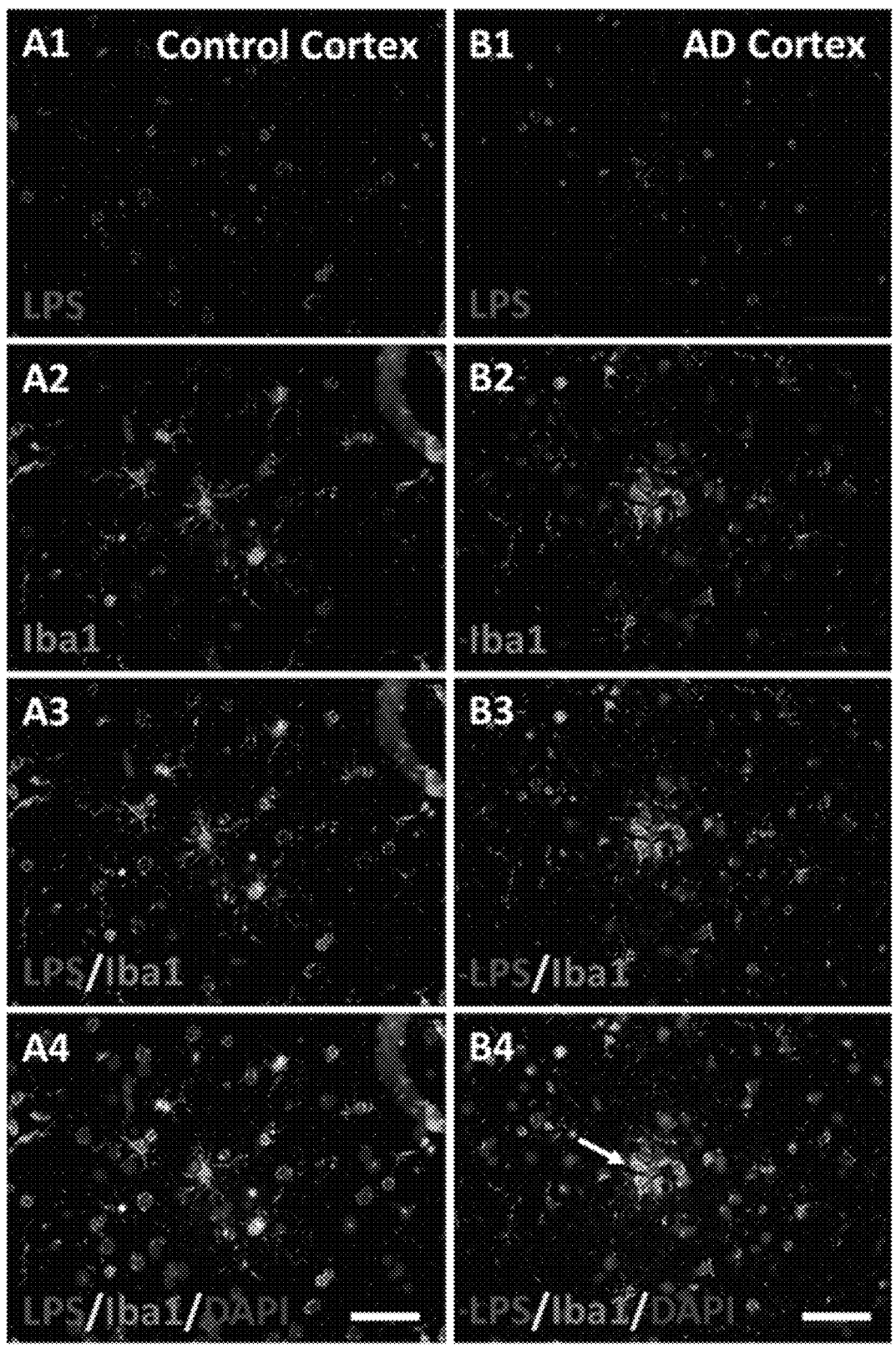
*Fig. 8A1-B4*

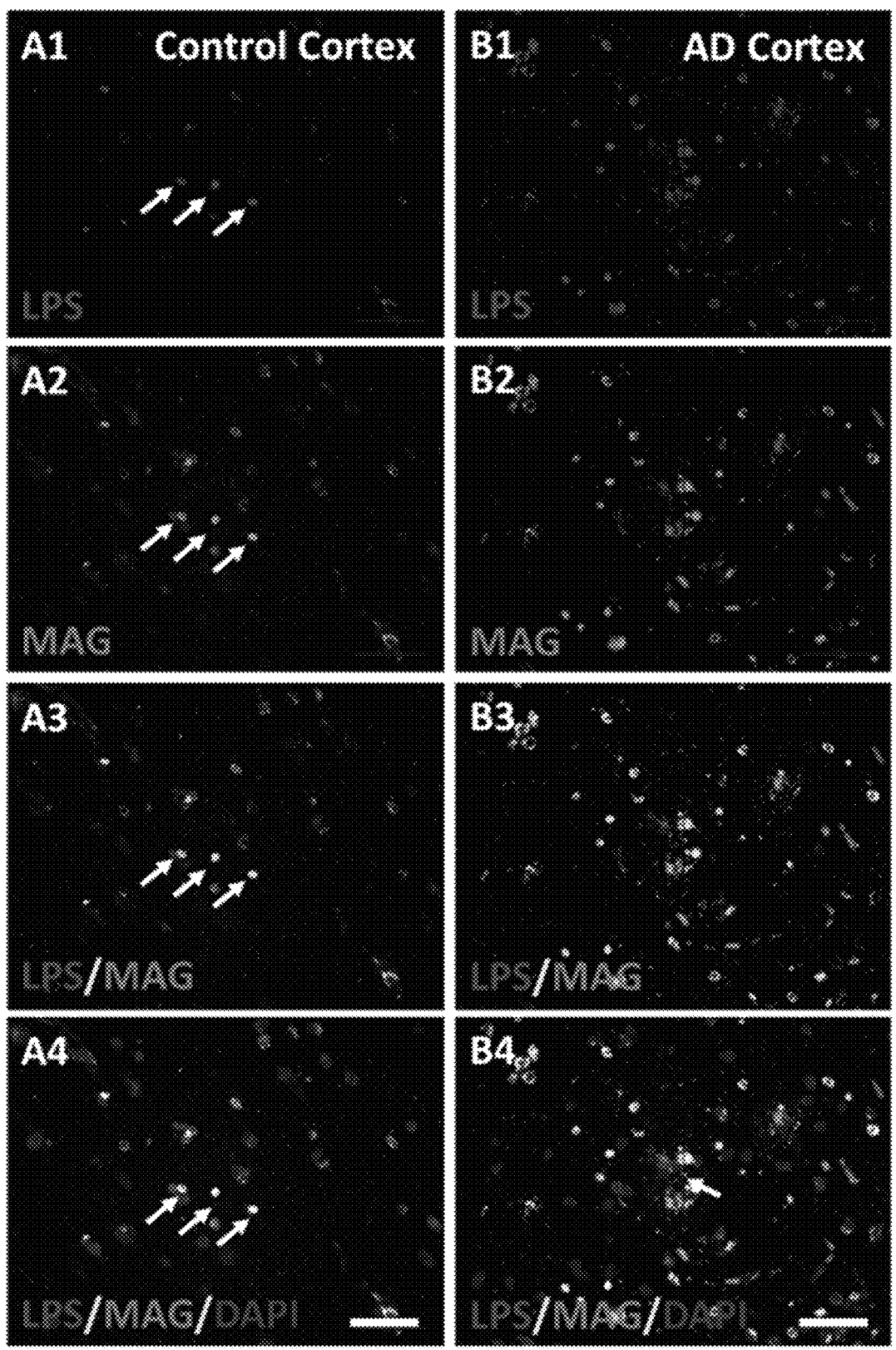
Fig. 9A1-B4

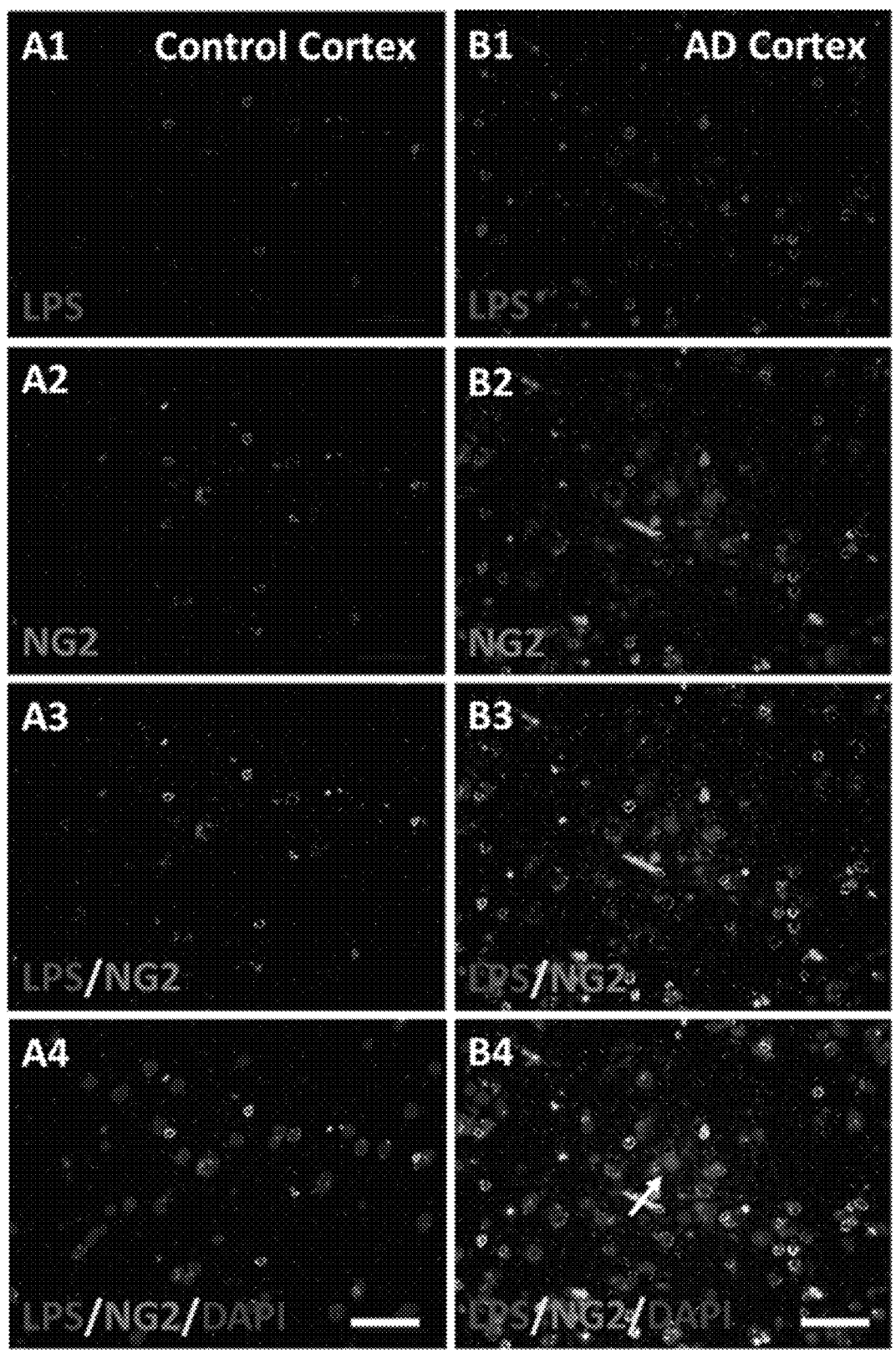
*Fig. 10A1-B4*

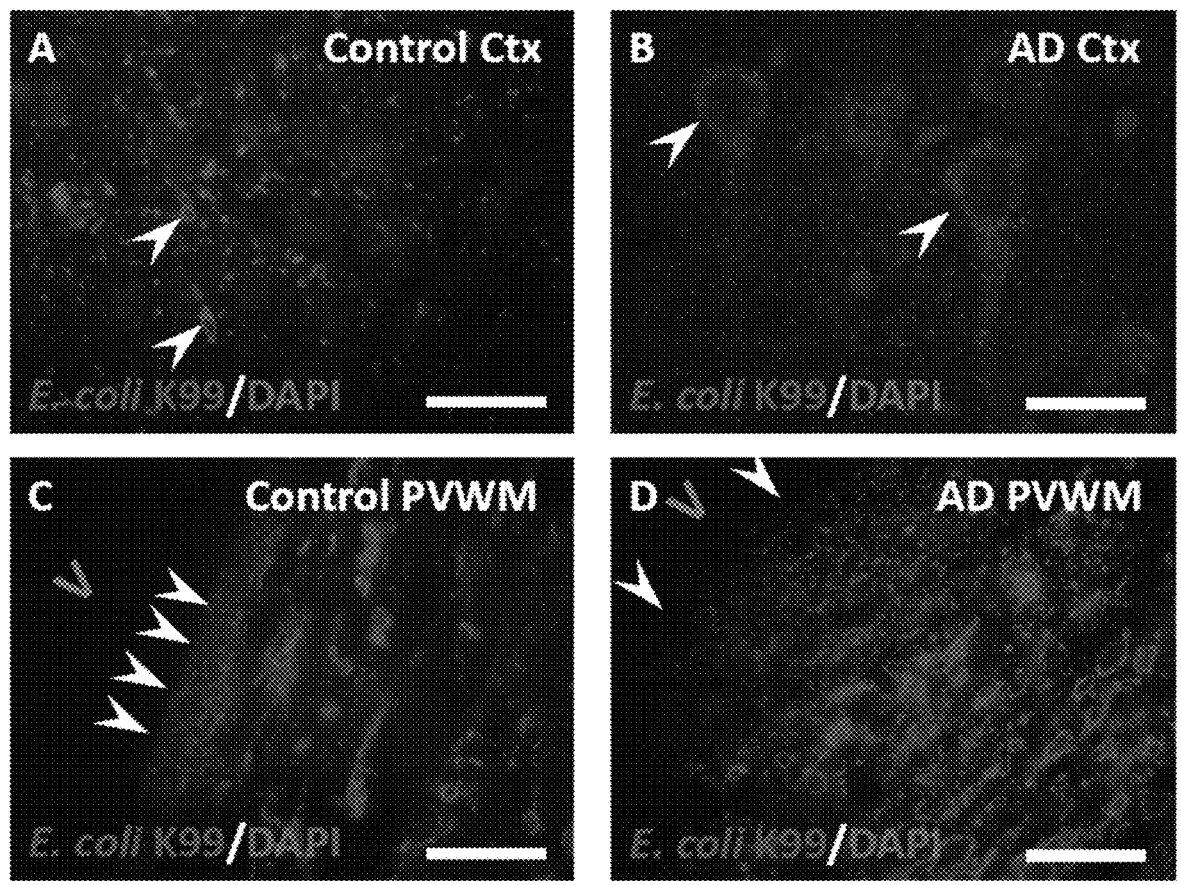
Fig. 11A-D

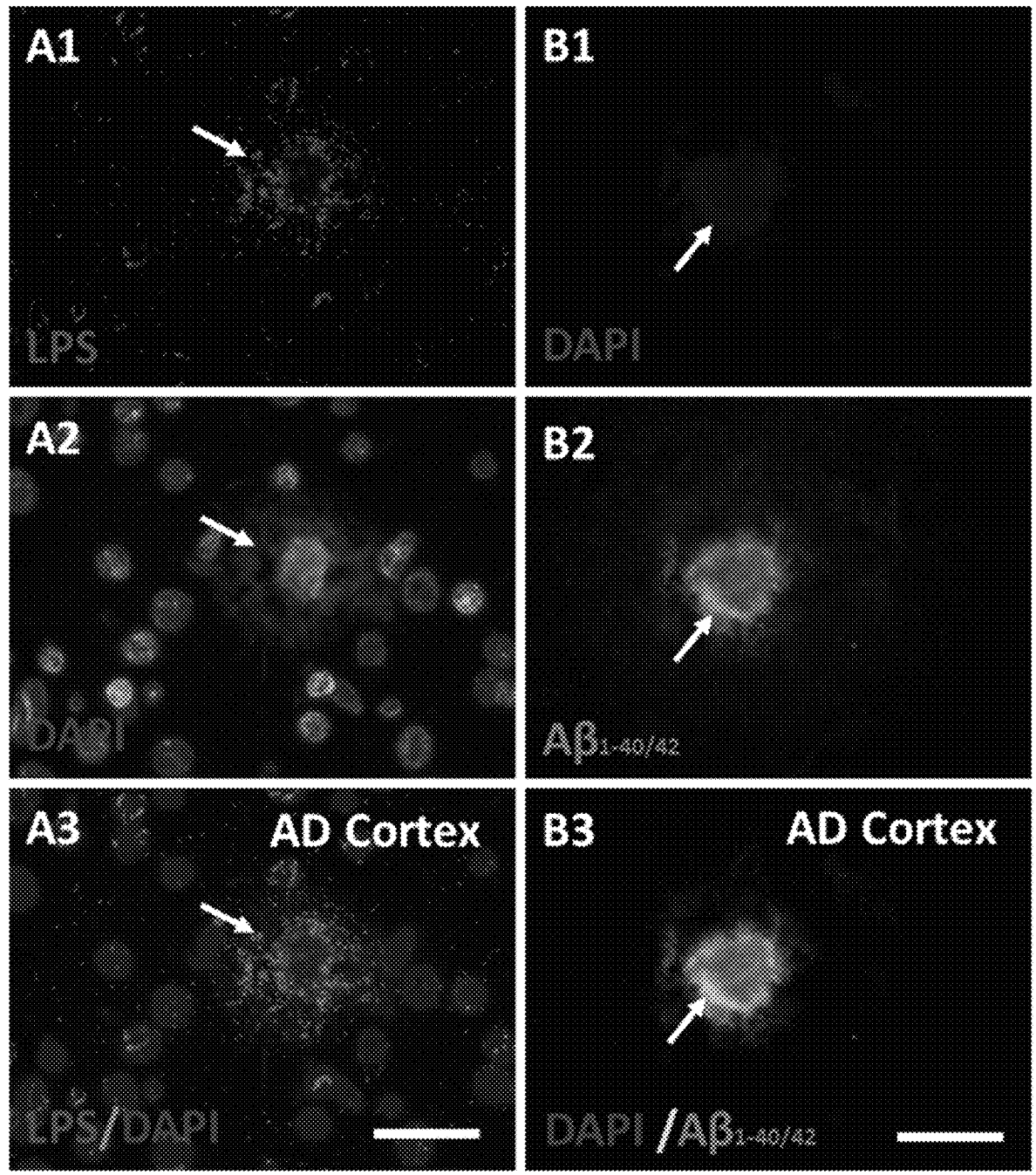
Fig. 12A1-B3

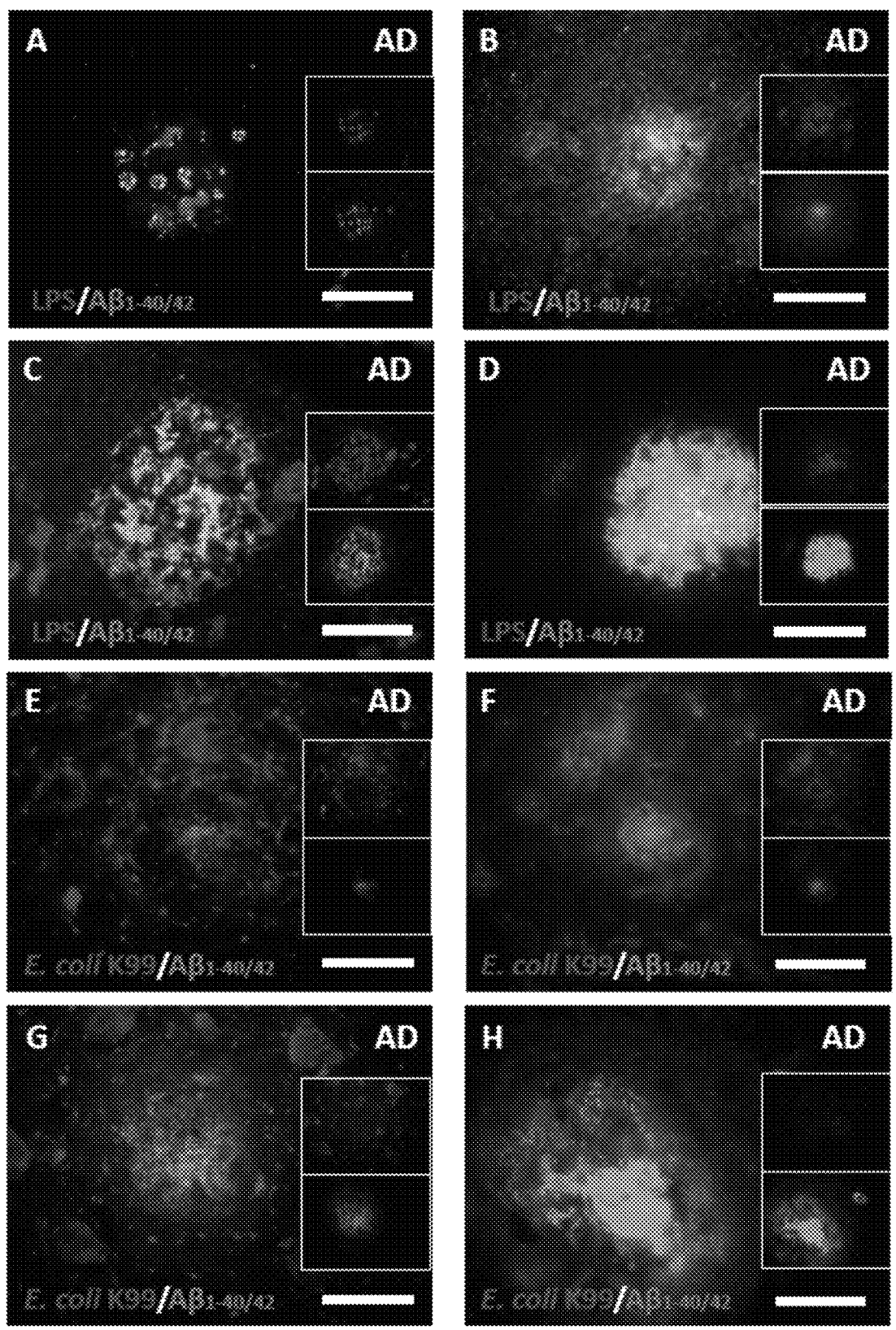
Fig. 13A-H

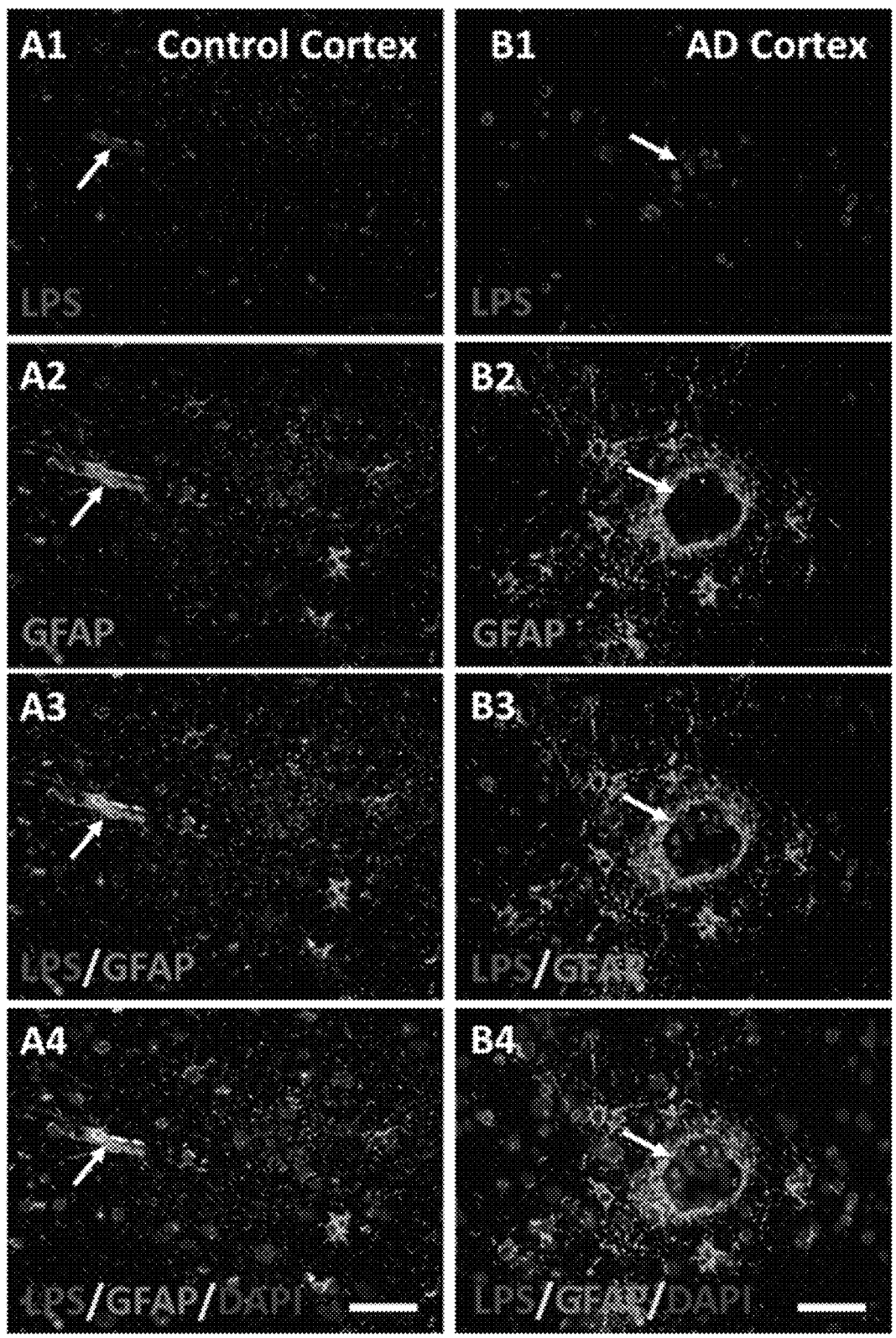
Fig. 14A1-B4

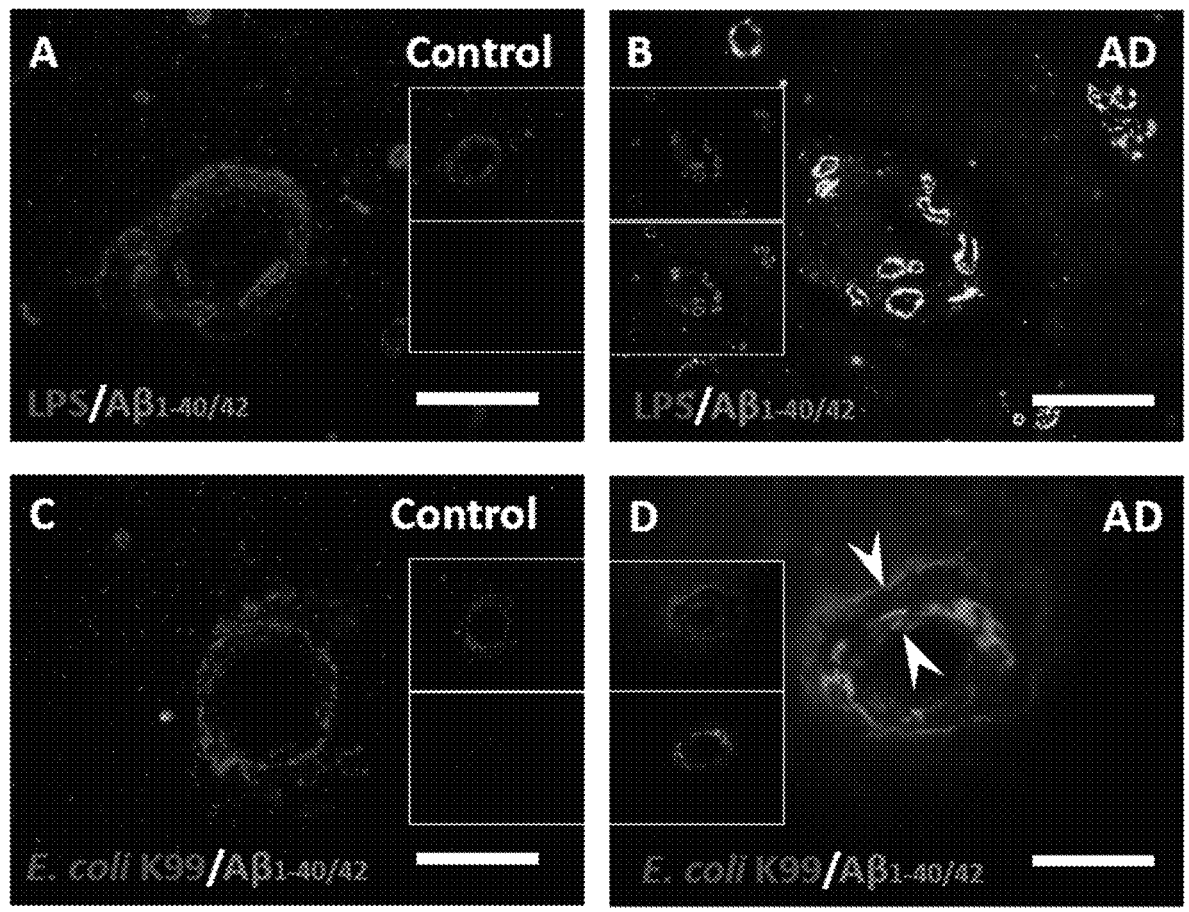
*Fig. 15A-D*

A
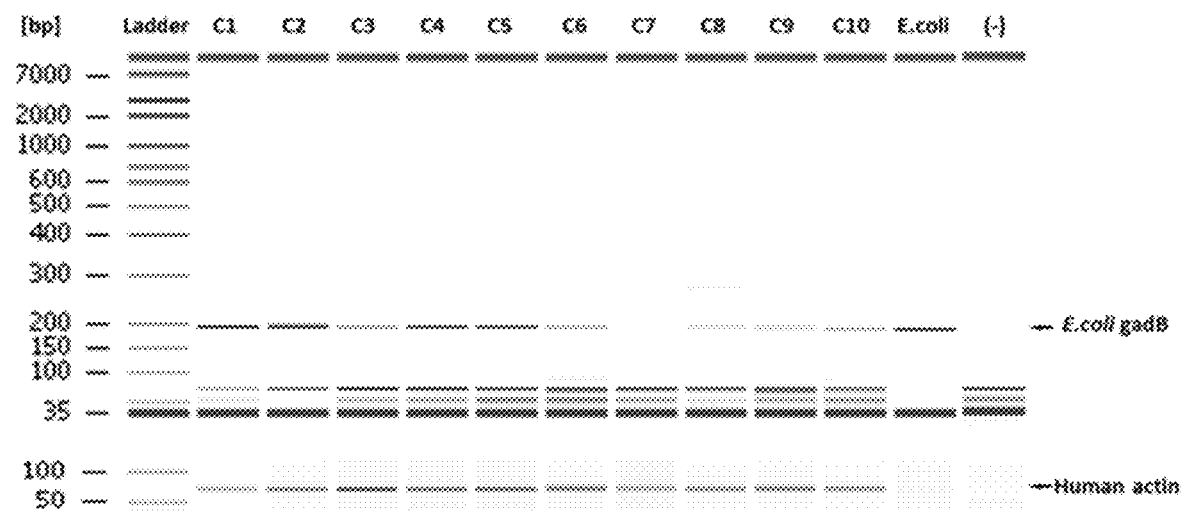
B
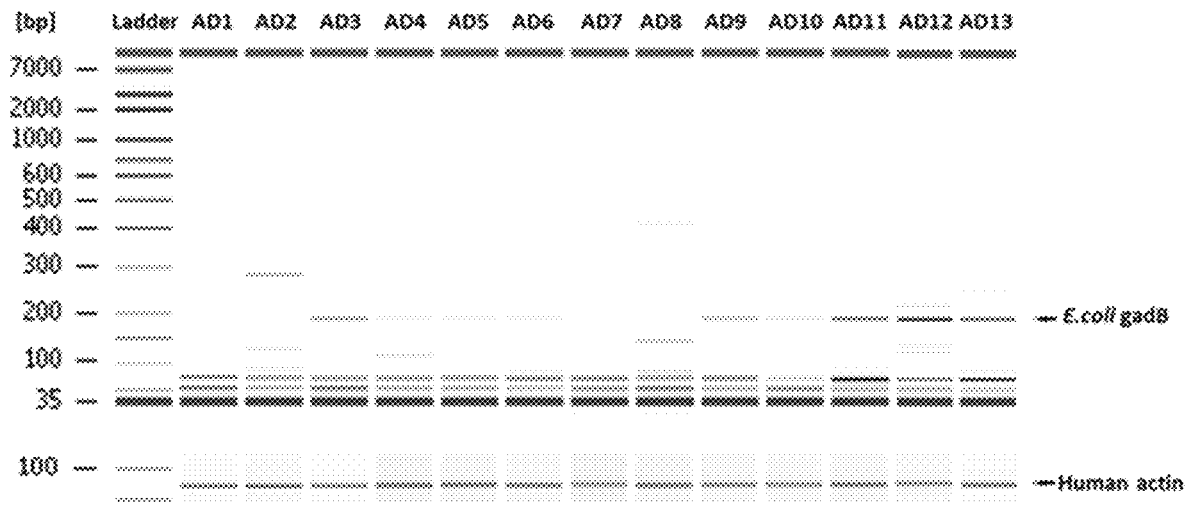
Fig. 16A-B

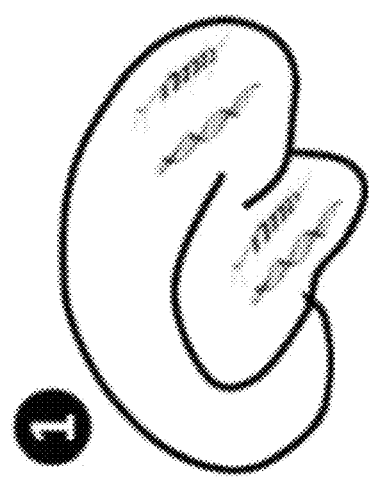
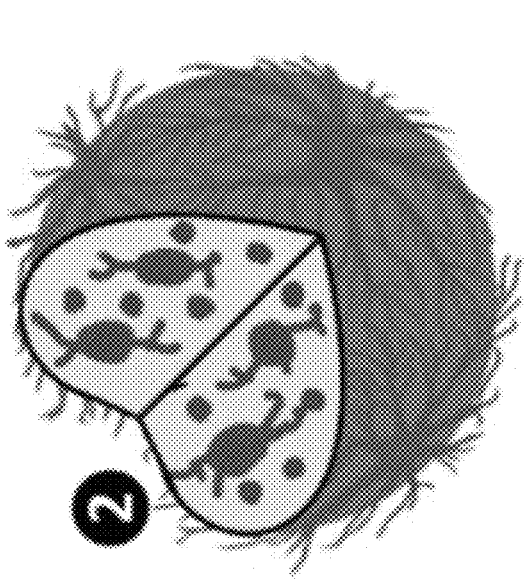
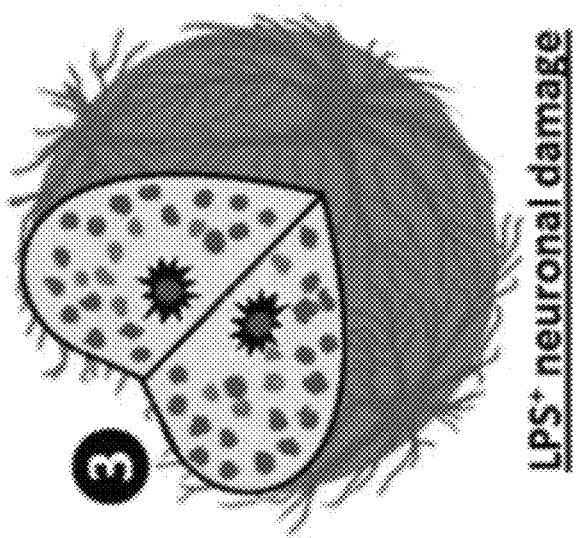
Fig. 23

SEQUENCE LISTING

```
<160> NUMBER OF SEQ ID NOS: 10

<210> SEQ ID NO 1
<211> LENGTH: 175
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
cacgttttgg tgcgaagtct atttccacta tcgcagaatc aaaacgtttt ccgctgcacg     60
aaatgcgcga cgatgtcgca ttccagatta tcaatgacga attatatctt gatggcaacg    120
ctcgtcagaa cctggccact ttctgccaga cttgggacga cgaaaatgtc cacaa          175

<210> SEQ ID NO 2
<211> LENGTH: 175
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2
cacgttttgg tgcgaagtct atttccacta tcgcagaatc aaaacgtttt ccgctgcacg     60
aaatgcgcga cgatgtcgca ttccagatta tcaatgacga attatatctt gatggcaacg    120
ctcgtcagaa cctggccact ttctgccaga cctgggacga cgaaaatgtc cacaa          175

<210> SEQ ID NO 3
<211> LENGTH: 175
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3
cacgttttgg tgcgaagtct atttccacta tcgcagaatc aaaacgtttt ccgctgcacg     60
aaatgcgcga cgatgtcgca ttccagatta tcaatgacga attatatctt gatggcaacg    120
ctcgtcagaa cctggccact ttctgccaga cctgggacga cgaaaatgtc cacaa          175

<210> SEQ ID NO 4
<211> LENGTH: 175
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4
cacgttttgg tgcgaagtct atttccacta tcgcagaatc aaaacgtttt ccgctgcacg     60
aaatgcgcga cgatgtcgca ttccagatta tcaatgacga attatatctt gatggcaacg    120
```
ctcgtcagaa cctggccact ttctgccaga cctgggacga cgaaaatgtc cacaa 175

<210> SEQ ID NO 5
<211> LENGTH: 175
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5
cacgttttgg tgcgaagtct atttccacta tcgcagaatc aaaacgtttt ccgctgcacg    60
aaatgcgcga cgatgtcgca ttccagatta tcaatgacga attatatctt gatggcaacg   120
ctcgtcagaa cctagccact ttctgccaga cttgggacga cgaaaatgtc cacaa        175

<210> SEQ ID NO 6
<211> LENGTH: 175
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6
cacgttttgg tgcgaagtct atttccacta tcgcagaatc aaaacgtttt ccgctgcacg    60
aaatgcgcga cgatgtcgca ttccagatta tcaatgacga attatatctt gatggcaacg   120
ttcgtcagaa cctggccact ttctgccaga cctgggacga cgaaaatgtc cacaa        175

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
cagaatccat tgcccggtga                                                 20

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ccatgtcaca cttttcgcat ct                                              22

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
cacgttttgg tgcgaagtct                                                 20

<210> SEQ ID NO 10
<211> LENGTH: 20
<212> TYPE: DNA

```
<213> ORGANISM: Artificial Sequence
<220> FEATURE:
<223> OTHER INFORMATION: Description of Artificial Sequence: Synthetic
      primer

<400> SEQUENCE: 10
ttgtggacat tttcgtcgtc                                                        20
```

METHODS OF DIAGNOSIS AND TREATMENT OF ALZHEIMER'S DISEASE

CROSS-REFERENCE TO RELATED APPLICATIONS

The present application is a continuation of International Patent Application No. PCT/US2017/058039, filed Oct. 24, 2017, which claims priority to U.S. Provisional Application No. 62/412,684 filed Oct. 25, 2016, the disclosures of which are herein incorporated by reference in their entirety for all purposes.

STATEMENT OF GOVERNMENTAL SUPPORT

This invention was made with Government support under Grant No. AG042292 awarded by the National Institutes of Health. The Government has certain rights in the invention.

REFERENCE TO A "SEQUENCE LISTING"

The Sequence Listing written in file SequenceListing_070772-226610US-1134856.txt created on Apr. 19, 2019, 3,564 bytes, machine format IBM-PC, MS-Windows operating system, is hereby incorporated by reference in its entirety for all purposes.

BACKGROUND

Though age is the number one risk factor for the late-onset sporadic form of Alzheimer's disease (AD), infection has also been implicated (1). Infection increases the odds of developing AD by two-fold over 5 years (2). DPT, polio, tetanus, or influenza vaccines reduce the risk of subsequent AD (3, 4). Inflammatory molecules including C-reactive protein and IL6 are elevated in blood years before dementia (5, 6). Though clinical trials show NSAIDs do not affect cognitive decline in AD (7), some studies suggest NSAIDs decrease the risk of developing AD (8). Indeed, recent studies have demonstrated that sporadic late-onset AD is associated with infections (9-12). However, a consistent link between these agents and AD neuropathology has not been demonstrated.

Gram-negative bacteria like *Escherichia coli* (*E. coli*) can deposit amyloid (13, 14). Moreover, we showed that administration of Gram-negative bacteria derived Lipopolysaccharide (LPS) followed by ischemia-hypoxia produced plaque-like aggregates of amyloid P in rat brains (15). Though Gram-negative bacteria have been reported as the predominant bacteria found in normal human brains (16), the study did not describe pathological correlates. Because of our finding that LPS promoted formation of amyloid-like plaques in rat brain (15), we determined whether Gram-negative bacterial molecules were associated with human AD neuropathology.

SUMMARY

In one aspect, provided are methods of mitigating, reversing or eliminating in a subject one or more symptoms associated with cognitive impairment associated with amyloid deposits in the brain. In some embodiments, the methods comprise delivering to the brain of the subject one or more compounds that prevent, reverse, delay, interfere with growth of or kill gram negative bacteria, in an amount sufficient to mitigate, reverse or eliminate the one or more symptoms of said cognitive impairment. In some embodiments, the compound is one or more antibiotics effective to prevent or delay or interfere with growth of or kill gram negative bacteria. In some embodiments, the antibiotic is selected from the group consisting of a quinolone antibiotic (e.g., nalidixic acid, ofloxacin, levofloxacin, ciprofloxacin, norfloxacin, enoxacin, lomefloxacin, grepafloxacin, trovafloxacin, sparfloxacin, temafloxacin, moxifloxacin, gatifloxacin, gemifloxacin), a beta-lactamase (e.g., penicillin, cloxacillin, dicloxacillin, flucloxacillin, methicillin, nafcillin, oxacillin, temocillin, amoxicillin, ampicillin, mecillinam, carbenicillin, ticarcillin, azlocillin, mezlocillin, piperacillin), an aminoglycoside (e.g., amikacin, gentamicin, kanamycin, neomycin, streptomycin, tobramycin), a cephalosporin (e.g., cefadroxil, cefazolin, cephalexin, cefaclor, cefoxitin, cefprozil, cefuroxime, loracarbef, cefixime, cefdinir, cefditoren, cefoperazone, cefotaxime, cefpodoxime, cefepime, ceftobiprole), a monobactam (e.g., aztreonam, tigemonam, nocardicin A, tabtoxinine β-lactam), a carbapenem (e.g., biapenem, doripenem, ertapenem, faropenem, imipenem, meropenem, panipenem, razupenem, tebipenem, thienamycin) and a tetracycline (e.g., tetracycline, chlortetracycline, oxytetracycline, demeclocycline, lymecycline, meclocycline, methacycline, minocycline, rolitetracycline, tigecycline). In some embodiments, the antibiotic is co-administered with lysozyme and EDTA. In some embodiments, the compound is an inhibitor of toll like receptor 4 (TLR4). In some embodiments, the TLR4 inhibitor is selected from the group consisting of TAK-242, amitriptyline, cyclobenzaprine, ketotifen, imipramine, mianserin, ibudilast, naloxone, (+)-naloxone, naltrexone, (+)-naltrexone, *Rhodobacter sphaeroides* Lipopolysaccharide (LPS-RS), propentofylline and tapentadol. In some embodiments, the compound is an antibody or fragment thereof that specifically binds to an antigen on a gram-negative bacteria. In some embodiments, the antigen is selected from the group consisting of Gram-negative lipopolysaccharide (LPS), LPS O antigen, *E. coli* K99 pill protein, *E. coli* J5 LPS, an LPS/Aβ1-40/42 aggregate, an admixture comprising LPS and Aβ1-40/42 peptide or fragments thereof, Gram-negative GrpE, Gram-negative CAT (Chloramphenicol Acetyltransferase), Gram-negative TetR (Tet Repressor Protein), Gram-negative ALK (Alkaline Phosphatase), Gram-negative β gal (β-Galactosidase), one or more *Porphyromonas gingivalis* gingipains (e.g., Arginine Gingipain A (RgpA) and/or Arginine Gingipain B (RgpB) and/or Lysine Gingipain (Kgp)), and fragments thereof. In some embodiments, the one or more compounds are administered orally, intravenously, intrathecally, intramuscularly, intranasally, subcutaneously. In some embodiments, the one or more compounds are administered to the cerebral spinal fluid. In some embodiments, the one or more compounds are co-administered with or encapsulated within an agent that facilitates delivery across the blood-brain-barrier. In varying embodiments, the one or more compounds are co-administered with or encapsulated within an exosome, a liposome or a nanoparticle.

In a further aspect, provided are methods of mitigating, reversing or eliminating in a subject one or more symptoms associated with cognitive impairment associated with amyloid deposits in the brain. In some embodiments, the methods comprise administering to the subject one or more immunogenic antigens sufficient to induce or enhance an immune response in the subject against gram negative bacteria in the brain, thereby reducing or eliminating the presence of gram negative bacteria in the brain in the subject, and mitigating, reversing or eliminating the one or more symptoms of said cognitive impairment. In some embodiments, the one or more immunogenic antigens are selected from the group consisting of selected from the group consisting of Gram-negative lipopolysaccharide (LPS), *E. coli* K99 pili protein, *E. coli* J5 LPS, an LPS/Aβ1-40/42 aggregate, an admixture comprising LPS and Aβ1-40/42 peptide or fragments thereof, Gram-negative GrpE, Gram-negative CAT (Chloramphenicol Acetyltransferase), Gram-negative TetR (Tet Repressor Protein), Gram-negative ALK (Alkaline Phosphatase), Gram-negative β gal (β-Galactosidase), one or more *Porphyromonas gingivalis* gingipains or fragments thereof (e.g., Arginine Gingipain A (RgpA) and/or Arginine Gingipain B (RgpB) and/or Lysine Gingipain (Kgp)), and fragments thereof. In some embodiments, the immunogenic antigen is linked to a carrier to form a conjugate. In some embodiments, the carrier is a heterologous polypeptide. In some embodiments, the carrier is a tetanus toxoid or a diphtheria toxoid. In some embodiments, the immunogenic antigen is administered with a pharmaceutical carrier as a pharmaceutical composition. In some embodiments, the immunogenic antigen is administered in combination with an adjuvant. In some embodiments, the adjuvant is pharmaceutically acceptable for human administration. In some embodiments, the adjuvant is selected from the group consisting of QS21, monophosphoryl lipid, alum, CpG, IL-12, IL 15, granulocyte-macrophage colony stimulating factor (GM-CSF) and macrophage colony stimulating factor (M-CSF). In some embodiments, the immunogenic antigen is administered at a dosage of 1-500 µg per injection. In some embodiments, the immunogenic antigen is administered in multiple dosages over at least six months. In some embodiments, the immunogenic antigen is administered intraperitoneally, subcutaneously, intradermally, intramuscularly, intranasally or intravenously.

With respect to embodiments applicable to the methods of treatment (e.g., by administration of an antibiotic effective against gram-negative bacteria, TLR4 inhibitor/antagonist, active or passive immunization against gram negative bacteria), in some embodiments, the methods further comprise, before delivering or administering the active agent or compound, the step of detecting in one or more biological samples from the subject an approximately 500 bp PCR product of bacterial galactose-1-phosphate uridylyltransferase (GalT)—UDP-galactose-4-epimerase (GalE)—molybdate ABC transporter ATP-binding protein (modF) DNA amplified using forward primer (5'→3') CAGAATCCATTGCCGGTGA and reverse sequence (5'→3') CCATGTCACACTTTTCGCATCT. In some embodiments, the methods further comprise, before delivering or administering the active agent or compound, the step of detecting in one or more biological samples from the subject *Escherichia coli* J5 strain truncated LPS. In varying embodiments, the one or more biological samples are selected from the group consisting of blood, serum, plasma, cerebral spinal fluid (CSF), tears, saliva, buccal swab, gum swab, throat culture, sputum, urine, fecal sample, and brain biopsy. In varying embodiments, the subject has mild cognitive impairment. In some embodiments, the subject has Alzheimer's Disease. In some embodiments, the subject is human. In some embodiments, the subject is a human and the mitigation comprises a perceived improvement in quality of life by the human. In some embodiments, the gram negative bacterium is *E. coli*. In some embodiments, administration of the compound or the immunogenic antigen delays or prevents the progression of MCI to Alzheimer's disease. In some embodiments, the subject is at risk of developing Alzheimer's disease. Such a subject can be asymptomatic for cognitive deficits or impairment. In some embodiments, the subject exhibits or has exhibited olfactory impairment or dysfunction, e.g., as determined in an olfactory challenge test. In some embodiments, the subject has a familial risk for having Alzheimer's disease. In some embodiments, the subject has a familial Alzheimer's disease (FAD) mutation. In some embodiments, the subject has the APOE ε4 allele. In some embodiments, the subject is free of and does not have genetic risk factors of Parkinson's disease or schizophrenia. In some embodiments, the subject is not diagnosed as having or at risk for Parkinson's disease or schizophrenia. In some embodiments, the subject does not have a neurological disease or disorder other than Alzheimer's disease. In some embodiments, the subject is not diagnosed as having or at risk for a neurological disease or disorder other than Alzheimer's disease. In some embodiments, the mitigation comprises a reduction in the cerebral spinal fluid (CSF) of levels of one or more components selected from the group consisting of total-Tau (tTau), phospho-Tau (pTau), APPneo, soluble Aβ40, pTau/Aβ42 ratio and tTau/Aβ42 ratio, and/or an increase in the CSF of levels of one or more components selected from the group consisting of Aβ42/Aβ40 ratio, Aβ42/Aβ38 ratio, sAPPα, sAPPα/sAPPβ ratio, sAPPα/Aβ40 ratio, and sAPPα/Aβ42 ratio. In some embodiments, the mitigation comprises a reduction of the plaque load in the brain of the subject. In some embodiments, the mitigation comprises a reduction in the rate of plaque formation in the brain of the subject. In some embodiments, the mitigation comprises an improvement in the cognitive abilities of the subject. In some embodiments, the mitigation comprises an improvement in, a stabilization of, or a reduction in the rate of decline of the clinical dementia rating (CDR) of the subject. In some embodiments, the methods further comprise prior to the administration or delivering step, the step of determining in a central nervous system (CNS) sample from the subject for the presence of gram negative bacteria (e.g., *E. coli*). In some embodiments, the central nervous system (CNS) sample is a cerebral spinal fluid (CSF) sample. In some embodiments, the central nervous system (CNS) sample is a brain tissue sample (e.g., superior temporal gyrus gray matter (GM) and/or frontal lobe white matter (WM)). In some embodiments, the presence of one or more gram negative bacteria biomarkers selected from the group consisting of Gram-negative lipopolysaccharide (LPS), *E. coli* K99 pili protein, *E. coli* J5 LPS, an LPS/Aβ1-40/42 aggregate, an admixture comprising LPS and Aβ1-40/42 peptide or fragments thereof, Gram-negative GrpE, Gram-negative CAT (Chloramphenicol Acetyltransferase), Gram-negative TetR (Tet Repressor Protein), Gram-negative ALK (Alkaline Phosphatase), Gram-negative β gal (β-Galactosidase), one or more *Porphyromonas gingivalis* gingipains (e.g., Arginine Gingipain A (RgpA) and/or Arginine Gingipain B (RgpB) and/or Lysine Gingipain (Kgp)) is determined.

In a further aspect, provided are methods of determining whether gram-negative bacteria molecules are associated with amyloid plaques in a subject exhibiting one or more symptoms associated with cognitive impairment associated with amyloid deposits in the brain, comprising determining in a central nervous system (CNS) sample from the subject for the presence of gram negative bacteria; and positively identifying the presence of gram negative bacteria in the CNS sample as indicative of gram-negative bacteria molecules associated with amyloid plaques in the subject. In some embodiments, the central nervous system (CNS) sample is a cerebral spinal fluid (CSF) sample. In some embodiments, the central nervous system (CNS) sample is a brain tissue sample (e.g., superior temporal gyrus gray matter (GM) and/or frontal lobe white matter (WM)). In some embodiments, the presence of one or more gram negative bacteria biomarkers selected from the group consisting of Gram-negative lipopolysaccharide (LPS), LPS O antigen, *E. coli* K99 pili protein, *E. coli* J5 LPS, an LPS/Aβ1-40/42 aggregate, an admixture comprising LPS and Aβ1-40/42 peptide or fragments thereof, Gram-negative GrpE, Gram-negative CAT (Chloramphenicol Acetyltransferase), Gram-negative TetR (Tet Repressor Protein), Gram-negative ALK (Alkaline Phosphatase), Gram-negative β gal (β-Galactosidase), one or more *Porphyromonas gingivalis* gingipains (e.g., Arginine Gingipain A (RgpA) and/or Arginine Gingipain B (RgpB) and/or Lysine Gingipain (Kgp)) is determined. In some embodiments, the gram negative bacterium is *E. coli*. In varying embodiments, the presence of one or more gram negative bacteria are identified by detecting in the CNS sample from the subject an approximately 500 bp PCR product of bacterial galactose-1-phosphate uridylyltransferase (GalT)—UDP-galactose-4-epimerase (GalE)—molybdate ABC transporter ATP-binding protein (modF) DNA amplified using forward primer (5'→3') CAGAATCCATTGCCCGGTGA and reverse sequence (5'→3') CCATGTCACACTTTTCGCATCT.

Definitions

As used herein, "administering" refers to local and systemic administration, e.g., including enteral, parenteral, pulmonary, and topical/transdermal administration. Routes of administration for compounds (e.g., one or more of antibiotics useful to treat gram-negative bacteria and/or TLR4 inhibitors and/or antibodies or fragments thereof against a gram-negative bacterial antigen) that find use in the methods described herein include, e.g., oral (per os (P.O.)) administration, nasal or inhalation administration, administration as a suppository, topical contact, transdermal delivery (e.g., via a transdermal patch), intrathecal (IT) administration, intravenous ("iv") administration, intraperitoneal ("ip") administration, intramuscular ("im") administration, intralesional administration, or subcutaneous ("sc") administration, or the implantation of a slow-release device e.g., a mini-osmotic pump, a depot formulation, etc., to a subject. Administration can be by any route including parenteral and transmucosal (e.g., oral, nasal, vaginal, rectal, or transdermal). Parenteral administration includes, e.g., intravenous, intramuscular, intra-arterial, intradermal, subcutaneous, intraperitoneal, intraventricular, ionophoretic and intracranial. Other modes of delivery include, but are not limited to, the use of liposomal formulations, intravenous infusion, transdermal patches, etc.

The terms "systemic administration" and "systemically administered" refer to a method of administering a compound or composition to a mammal so that the compound or composition is delivered to sites in the body, including the targeted site of pharmaceutical action, via the circulatory system. Systemic administration includes, but is not limited to, oral, intranasal, rectal and parenteral (e.g., other than through the alimentary tract, such as intramuscular, intravenous, intra-arterial, transdermal and subcutaneous) administration.

The terms "co-administering" or "concurrent administration", when used, for example with respect to the compounds (e.g., one or more of antibiotics useful to treat gram-negative bacteria and/or TLR4 inhibitors and/or antibodies or fragments thereof against a gram-negative bacterial antigen) and/or analogs thereof and another active agent (e.g., a cognition enhancer), refers to administration of the compound and/or analogs and the active agent such that both can simultaneously achieve a physiological effect. The two agents, however, need not be administered together. In certain embodiments, administration of one agent can precede administration of the other. Simultaneous physiological effect need not necessarily require presence of both agents in the circulation at the same time. However, in certain embodiments, co-administering typically results in both agents being simultaneously present in the body (e.g., in the plasma) at a significant fraction (e.g., 20% or greater, preferably 30% or 40% or greater, more preferably 50% or 60% or greater, most preferably 70% or 80% or 90% or greater) of their maximum serum concentration for any given dose.

The terms "effective amount" or "pharmaceutically effective amount" refer to the amount and/or dosage, and/or dosage regime of one or more compounds necessary to bring about the desired result e.g., an amount sufficient to mitigating in a mammal one or more symptoms associated with mild cognitive impairment (MCI), or an amount sufficient to lessen the severity or delay the progression of a disease characterized by amyloid deposits in the brain in a mammal (e.g., therapeutically effective amounts), an amount sufficient to reduce the risk or delaying the onset, and/or reduce the ultimate severity of a disease characterized by amyloid deposits in the brain in a mammal (e.g., prophylactically effective amounts).

The phrase "cause to be administered" refers to the actions taken by a medical professional (e.g., a physician), or a person controlling medical care of a subject, that control and/or permit the administration of the agent(s)/compound(s) at issue to the subject. Causing to be administered can involve diagnosis and/or determination of an appropriate therapeutic or prophylactic regimen, and/or prescribing particular agent(s)/compounds for a subject. Such prescribing can include, for example, drafting a prescription form, annotating a medical record, and the like.

The phrase "in conjunction with" when used in reference to the use of the active agent(s) described herein (e.g., one or more of antibiotics and/or TLR4 inhibitors; or an analogue thereof, an enantiomer, a mixture of enantiomers, a pharmaceutically acceptable salt, solvate, or hydrate of said compound(s) or analogue(s) and/or antibodies or fragments thereof against a gram-negative bacterial antigen and/or a gram-negative bacteria immunogenic antigen) in conjunction with one or more other drugs useful for ameliorating symptoms of cognitive impairment associated with amyloid plaques in the brain (e.g., an acetylcholinesterase inhibitor) the active agent(s) and the other drug(s) are administered so that there is at least some chronological overlap in their physiological activity on the organism. When they are not administered in conjunction with each other, there is no chronological overlap in physiological activity on the organism. In certain preferred embodiments, the "other drug(s)" are not administered at all (e.g., not co-administered) to the organism.

As used herein, the terms "treating" and "treatment" refer to delaying the onset of, retarding or reversing the progress of, reducing the severity of, or alleviating or preventing either the disease or condition to which the term applies, or one or more symptoms of such disease or condition.

The term "mitigating" refers to reduction or elimination of one or more symptoms of that pathology or disease, and/or a reduction in the rate or delay of onset or severity of one or more symptoms of that pathology or disease, and/or the prevention of that pathology or disease. In certain embodiments, the reduction or elimination of one or more symptoms of pathology or disease can include, but is not limited to, reduction or elimination of one or more markers that are characteristic of the pathology or disease (e.g., of total-Tau (tTau), phospho-Tau (pTau), APPneo, soluble Aβ40, pTau/Aβ42 ratio and tTau/Aβ42 ratio, and/or an increase in the CSF of levels of one or more components selected from the group consisting of Aβ42/Aβ40 ratio, Aβ42/Aβ38 ratio, sAPPα, sAPPα/sAPPβ ratio, sAPPα/Aβ40 ratio, sAPPα/Aβ42 ratio, etc.) and/or reduction, stabilization or reversal of one or more diagnostic criteria (e.g., clinical dementia rating (CDR)).

As used herein, the phrase "consisting essentially of" refers to the genera or species of active pharmaceutical agents recited in a method or composition, and further can include other agents that, on their own do not substantial activity for the recited indication or purpose. In some embodiments, the phrase "consisting essentially of" expressly excludes the inclusion of one or more additional agents that have neuropharmacological activity other than the recited compounds (e.g., other than one or more of antibiotics useful to treat gram-negative bacteria and/or TLR4 inhibitors and/or antibodies or fragments thereof against a gram-negative bacterial antigen and/or a gram-negative bacteria immunogenic antigen). In some embodiments, the phrase "consisting essentially of" expressly excludes the inclusion of one or more additional active agents other than the compounds (e.g., other than other than one or more of antibiotics useful to treat gram-negative bacteria and/or TLR4 inhibitors and/or antibodies or fragments thereof against a gram-negative bacterial antigen and/or a gram-negative bacteria immunogenic antigen). In some embodiments, the phrase "consisting essentially of" expressly excludes the inclusion of one or more acetylcholinesterase inhibitors.

The terms "subject," "individual," and "patient" interchangeably refer to a mammal, preferably a human or a non-human primate, but also domesticated mammals (e.g., canine or feline), laboratory mammals (e.g., mouse, rat, rabbit, hamster, guinea pig) and agricultural mammals (e.g., equine, bovine, porcine, ovine). In various embodiments, the subject can be a human (e.g., adult male, adult female, adolescent male, adolescent female, male child, female child) under the care of a physician or other health worker in a hospital, psychiatric care facility, as an outpatient, or other clinical context. In certain embodiments the subject may not be under the care or prescription of a physician or other health worker.

The term "nanoparticle" refers to a particle having a sub-micron (m) size. In various embodiments, microparticles have a characteristic size (e.g., diameter) less than about 1 μm, 800 nm, or 500 nm, preferably less than about 400 nm, 300 nm, or 200 nm, more preferably about 100 nm or less, about 50 nm or less or about 30 or 20 nm or less.

An "immunogen" refers to a compound or composition comprising a peptide, polypeptide or protein which is "immunogenic," i.e., capable of eliciting, augmenting or boosting a cellular and/or humoral immune response, either alone or in combination or linked or fused to another substance. An immunogenic composition can be a peptide of at least about 5 amino acids, a peptide of 10 amino acids in length, a fragment 15 amino acids in length, a fragment 20 amino acids in length or greater. The immunogen can comprise a "carrier" polypeptide and a hapten, e.g., a fusion protein or a carrier polypeptide fused or linked (chemically or otherwise) to another composition (described below). The immunogen can be recombinantly expressed in an immunization vector, which can be simply naked DNA comprising the immunogen's coding sequence operably linked to a promoter, e.g., a simple expression cassette. The immunogen includes antigenic determinants, or epitopes (described below), to which antibodies or TCRs bind, which are typically 3 to 10 amino acids in length.

The term "antibody" is used in the broadest sense and includes fully assembled antibodies, tetrameric antibodies, monoclonal antibodies, polyclonal antibodies, multispecific antibodies (e.g., bispecific antibodies), antibody fragments that can bind an antigen (e.g., Fab', F'(ab)2, Fv, single chain antibodies, diabodies), and recombinant peptides comprising the forgoing as long as they exhibit the desired biological activity. An "immunoglobulin" or "tetrameric antibody" is a tetrameric glycoprotein that consists of two heavy chains and two light chains, each comprising a variable region and a constant region. Antigen-binding portions may be produced by recombinant DNA techniques or by enzymatic or chemical cleavage of intact antibodies. Antibody fragments or antigen-binding portions include, inter alia, Fab, Fab', F(ab')2, Fv, domain antibody (dAb), complementarity determining region (CDR) fragments, CDR-grafted antibodies, single-chain antibodies (scFv), single chain antibody fragments, chimeric antibodies, diabodies, triabodies, tetrabodies, minibody, linear antibody; chelating recombinant antibody, a tribody or bibody, an intrabody, a nanobody, a small modular immunopharmaceutical (SMIP), an antigen-binding-domain immunoglobulin fusion protein, a camelized antibody, a VHH containing antibody, or a variant or a derivative thereof, and polypeptides that contain at least a portion of an immunoglobulin that is sufficient to confer specific antigen binding to the polypeptide, such as one, two, three, four, five or six CDR sequences, as long as the antibody retains the desired biological activity.

The phrase "specifically (or selectively) bind," when used in the context of describing the interaction between an antigen, e.g., a protein, to an antibody or antibody-derived binding agent, refers to a binding reaction that is determinative of the presence of the antigen in a heterogeneous population of proteins and other biologics, e.g., in one or more biological samples suspected of comprising gram negative bacteria, e.g., cerebral spinal fluid (CSF), blood, serum, plasma, brain tissue, tears, saliva, buccal swab, gum swab, throat culture, sputum, urine, fecal sample. Thus, under designated immunoassay conditions, the antibodies or binding agents with a particular binding specificity bind to a particular antigen at least two times the background and do not substantially bind in a significant amount to other antigens present in the sample. Specific binding to an antibody or binding agent under such conditions may require the antibody or agent to have been selected for its specificity for a particular protein. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Using Antibodies, A Laboratory Manual (1998), for a description of immunoassay formats and conditions that can be used to determine specific immunoreactivity). Typically a specific or selective binding reaction produces a signal at least twice over the background signal and more typically at least than 10 to 100 times over the background.

BRIEF DESCRIPTION OF THE DRAWINGS

FIGS. 3A-H illustrate immunofluorescence of Lipopolysaccharide (LPS) in human brains. Immunocytochemistry for LPS showed staining in both control (A, C) and AD brains (B, D) in gray matter (A, B) and in periventricular white matter (PVWM, C, D). LPS co-localized with 4',6-diamidino-2-phenylindole (DAPI)-stained nuclei in control gray matter (E) and white matter (G) including ependymal cells (G, arrow heads). The patterns of control LPS staining in the DAPI stained nuclei varied (E, yellow, green and white arrows). In AD gray matter there were large foci of LPS staining that appeared to be plaques in cortex (B, F—white arrow), and other LPS stained structures that appeared to be the size of nuclei in gray matter (B, F—yellow arrows). LPS staining was detected in control (C, G) and AD (D, H) white matter. DAPI staining of nuclei was decreased in AD cortex (F), and in white matter (H) including ventricular ependymal cells (H, white arrows)—likely indicating cell loss. LPS was detected in all 11 AD brains and all 7 control brains by immunofluorescence. Ctx=cortex, PVWM=periventricular white matter, AD=Alzheimer's disease. Bar=25 μm.

FIGS. 4A-D illustrate immunoabsorption specificity controls in AD and control brain. Immunofluorescence of AD and control brains using antibody against *E. coli* LPS (Abcam, ab35654) as well as *E. coli* LPS depleted antibody (LPS from VWR, 102946-492; antibody:LPS=1:10). The anti-*E. coli* LPS antibody detected nuclei in control (A) and AD (B) brains as well as plaques in AD brains (B), whereas *E. coli* LPS immune-depleted antibody completely eliminated all tissue staining in control brain (C) and AD brain (D). These data showed that LPS was being immunostained. AD=Alzheimer's disease. Bar=50 μm.

FIGS. 5A-D illustrate immunoabsorption specificity controls in AD and control brain. Immunohistochemistry of AD and control brains using antibody against Gram-negative LPS (RayBiotech, MD-05-0148) as well as *E. coli* LPS depleted antibody (LPS from VWR, 102946-492; antibody: LPS=1:10). The Gram-negative LPS antibody detected nuclei in control (A) and AD (B) brains as well as cytoplasm in AD brains (B), whereas *E. coli* LPS immune-depleted antibody completely eliminated all tissue staining in control brain (C) and AD brain (D). These data showed that LPS was being immunostained. AD=Alzheimer's disease. Bar=25 μm.

FIGS. 6 A1-B3 illustrate localization of LPS in neurons of AD brains. Immunofluorescence for LPS (A1, B1) showed staining in neurons using antibodies against NeuN (A2, A3) and Synapsin 2 (B2, B3). AD=Alzheimer's disease. Bar=50 m.

FIGS. 7 A1-B4 illustrate localization of LPS in the neurons of AD and control brains. In control brain, LPS (A1, red; A3, yellow; A4, cyan) was localized in the neuronal nuclei using a neuron marker, $GST_\pi$ (A2, green; A3, yellow, A4, cyan). In AD brains, LPS (B1, red) was also localized in neurons (B2, green; B3 yellow; B4, cyan) around coalesced DNA (B4, arrow). AD=Alzheimer's disease. Bar=50 μm.

FIGS. 8 A1-B4 illustrate localization of LPS in the microglia of AD and control brains. In control brain, LPS (A1, red; A3, orange; A4, purple) was localized in the microglial nuclei using a microglia marker, Iba1 (A2, green; A3, orange; A4, purple). In AD brains, LPS (B1, red) was also localized in microglia (B2, green; B3, orange; B4, purple) often around the coalesced DNA (B4, arrow). AD=Alzheimer's disease. Bar=50 μm.

FIGS. 9 A1-B4 illustrate localization of LPS in the oligodendrocytes of AD and control brains. In control brain, LPS (A1, A3, A4; arrow) was localized in the nuclei of oligodendrocytes using an oligodendrocyte marker, MAG (A2-4; arrow). In AD brains, LPS (B1, red) was also localized in oligodendrocytes (B2, green; B3, orange; B4, purple) often around coalesced DNA (84, arrow). Note many more LPS-MAG double stained oligodendrocytes in AD cortex compared to controls. AD=Alzheimer's disease. Bar=50 μm.

FIGS. 10 A1-B4 illustrate localization of LPS in the oligodendrocyte progenitor cells (OPCs) of AD and control brains. In control brain, LPS (A1, red; A3, orange; A4, purple) was localized in the nuclei of OPCs using an OPC marker, NG2 (A2, green; A3, orange, A4, purple). In AD brains, LPS (81, red) was also localized in the clustered OPCs (B2, green; B3, orange; B4, purple) around coalesced DNA (B4, arrow). Note many more LPS-NG2 double stained oligodendrocyte progenitors in AD cortex com oared to controls. AD=Alzheimer's disease. Bar=50 μm.

FIGS. 11A-D illustrate immunofluorescence of *E. coli* K99 pili protein in human brains. *E. coli* K99 staining in control cortex was punctate and not associated with DAPI stained nuclei (A). In control white matter K99 staining appeared to be associated with fiber tracts (C). In AD gray matter *E. coli* K99 pili protein was often found in pyramidal cells in the cytoplasm and not the nucleus (B, arrow heads). There was intense *E. coli* K99 pili protein staining in AD periventricular white matter (D) with loss of normal DAPI stained ependymal cells in AD brains (D, arrow heads) compared to controls (C, arrow heads). *E. coli* K99 pili protein was detected in all 11 AD brains and all 7 control brains by immunofluorescence. Ctx=cortex, PVWM=periventricular white matter, V=ventricle, AD=Alzheimer's disease. Bar=25 m.

FIGS. 12 A1-B3 illustrate co-localization of LPS and Aβ in coalesced DNA of AD brains. Immunofluorescence for LPS (A1, arrow) showed staining in DAPI+ stained cells which had lost their normal nuclear morphology (A2, A3; arrow). The coalesced DNA (B1, B3; arrow) was co-localized with an amyloid plaque marker, $Aβ_{1-40/42}$ antibody (B2, B3 arrow). AD=Alzheimer's disease. Bar=25 μm.

FIGS. 13A-H illustrate association of LPS and *E. coli* K99 pili protein with amyloid plaques in AD brains. There were several different patterns of co-localization of LPS and $A\beta_{1-40/42}$ in AD brains. There were clusters of predominantly LPS particles that co-localized with $A\beta_{1-40/42}$ (A). There were $A\beta_{1-40/42}$ deposits that co-localized with LPS and were surrounded by LPS (B, C). Finally, there were confluent $A\beta_{1-40/42}$ stained amyloid plaques that had scattered LPS particles within them (D). These LPS results contrasted with *E. coli* K99 pili protein which often surrounded small $A\beta_{1-40/42}$ stained amyloid plaques (E, F, G). For larger amyloid plaques (diameter >50 µm) *E. coli* K99 was usually absent (H). AD=Alzheimer's disease. Bar=25 µm.

FIGS. 14 A1-B4 illustrate association of LPS immunostaining with astrocytes of AD and control brains. In control brain, LPS (A1, A3, A4; arrow) was localized in a vessel using an astrocyte marker, GFAP (A2-4; arrow). In AD brains, LPS+ clusters (B1, arrow) were surrounded by GFAP+ astrocytes (B2-4, arrow). These astrocytes formed a round/spherical structure (B3, arrow). AD=Alzheimer's disease. Bar=50 µm.

FIGS. 15A-D illustrate association of LPS and *E. coli* K99 with blood vessels. LPS and *E. coli* K99 were also found in vessels of human brains. In control brains, both LPS (A) and *E. coli* K99 pili protein (C) were localized in blood vessels that did not stain for $A\beta_{1-40/42}$ (A, C). LPS, *E. coli* K99 pili protein and $A\beta_{1-40/42}$ were localized in vessels of AD brains (B, D). $A\beta_{1-40/42}$ co-localized (yellow staining) with LPS in vessels in AD brains (B). $A\beta_{1-40/42}$ was frequently sandwiched by but did not co-localize with *E. coli* K99 pili protein (D, arrow heads). AD=Alzheimer's disease. Bar=25 µm.

FIGS. 16A-B illustrate detection of *E. coli* DNA in human brains. PCR for the *E. coli* glutamate decarboxylase B gene (gadB) showed a 175 bps DNA fragment for the ATCC 8739 *E. coli* strain which was the same size in control and AD brains. 175 bps *E. coli* gadB DNA was detected in 9/10 normal control and 9/13 AD brains. Among these, 1/10 control and 4/13 AD brains had DNA fragments that were larger than 175 bps (A, B) which is of unknown significance. DNA fragments less than 175 bps likely represent primer interactions. C=control samples; AD=Alzheimer's Disease samples; (−)=negative control with no brain DNA. Human Actin DNA was used for a loading control.

FIG. 23 illustrates our central hypothesis that the *E. coli* molecules including LPS exists in AD brains (❶) and LPS aggregates cause inflammation in AD ❷ brain which activates neuroimmune defense units (❸) to protect against *E. coli* LPS (❹, red dots). The neuroimmune defense units consist of astrocytes (❺, red star-like cells), neuroimmune cells including microglia, (❻, purple cells) and LPS-microglia-associated cytokines (e.g. IL1, IL6, IL10, TNF, TGF). We propose that the neuroimmune defense unit is the site where LPS+ neurons are damaged (❼, black cells with red dot) and β amyloid (Aβ) accumulates (❽, green dots; red dots show LPS and yellow dots show Aβ overlaps with LPS).

DETAILED DESCRIPTION

1. Introduction

Figure 1A:
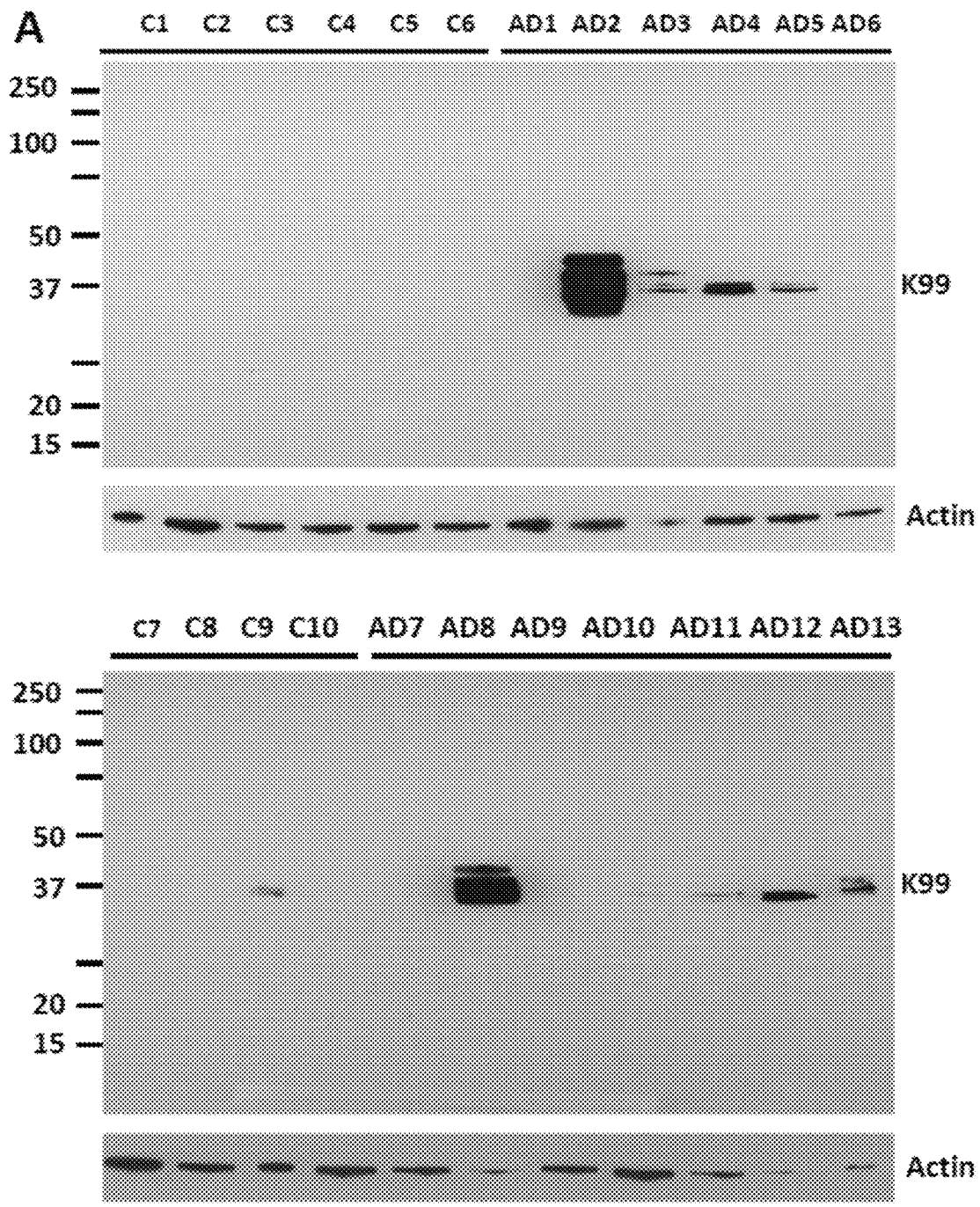
FIGS. 1A-D illustrate Western blot analysis of *E. coli* K99 pill protein and Gram-negative bacterial LPS in human brains. (A) Western blot analysis of *E. coli* K99 pill protein in gray matter. *E. coli* K99 was detected in 9 out of 13 AD cases and 1 out of 10 control cases. (B) Western blot analysis of *E. coli* K99 pill protein in white matter. *E. coli* K99 was detected in 10 out of 13 AD cases and 4 out of 10 control cases. (C) Quantification of *E. coli* K99 protein. *E. coli* K99 protein levels in AD brains were greater than in control aged brains in both gray matter (*$p<0.05$) and white matter (**$p<0.01$). (D) Western blot analysis of Gram-negative bacterial LPS. 3/3 AD gray matter, 3/3 AD white matter, and 0/3 control gray matter showed LPS. C=control, GM=gray matter, WM=white matter, LPS=Lipopolysaccharide. *$p<0.05$ and **$p<0.01$. Error bars are standard errors of the mean. β actin was used as a loading control.

OBJECTIVE: We determined whether Gram-negative bacterial molecules are associated with Alzheimer's disease (AD) neuropathology given that previous studies demonstrate Gram-negative *Escherichia coli* (*E. coli*) bacteria can form extracellular amyloid and Gram-negative bacteria have been reported as the predominant bacteria found in normal human brains.

METHODS: Brain samples from gray and white matter were studied from AD patients (n=24) and age-matched controls (n=18). LPS and *E. coli* K99 pill protein were evaluated by Western blots and immunocytochemistry. Human brain samples were assessed for *E. coli* DNA followed by DNA sequencing.

RESULTS: LPS and *E. coli* K99 were detected immunocytochemically in brain parenchyma and vessels in all AD and control brains. K99 levels measured using Western blots were greater in AD compared to control brains (p<0.01); and K99 was localized to neuron-like cells in AD but not control brains. LPS levels were also greater in AD compared to control brain. LPS co-localized with Aβ31-40/42 in amyloid plaques and with Aβ1-40/42 around vessels in AD brains. DNA sequencing confirmed *E. coli* DNA in human control and AD brains.

CONCLUSIONS: *E. coli* K99 and LPS levels were greater in AD compared to control brains. LPS co-localized with Aβ1-40/42 in amyloid plaques and around vessels in AD brain. The data show that Gram-negative bacterial molecules are associated with AD neuropathology. They are consistent with our LPS-ischemia-hypoxia rat model that produces myelin aggregates that co-localize with Aβ and which resemble amyloid-like plaques.

2. Subjects Who Can Benefit from the Present Methods

While the methods described herein are detailed primarily in the context of mild cognitive impairment (MCI) and Alzheimer's disease (AD) it is believed they can apply equally to other pathologies characterized by amyloidosis, and e.g., LPS/amyloid aggregates. Illustrative, but non-limiting list of conditions characterized by amyloid plaque formation are shown in Table 1.

TABLE 1

Illustrative pathologies characterized by amyloid formation/deposition.

| Disease | Characteristic Protein | Abbreviation |
|---|---|---|
| Alzheimer's disease | Beta amyloid | Aβ |
| Diabetes mellitus type 2 | Islet amyloid protein (Amylin) | IAPP |
| Parkinson's disease | Alpha-synuclein | SNCA |
| Transmissible spongiform encephalopathy e.g. Bovine spongiform encephalopathy | Prion | PrP |
| Huntington's Disease | Huntingtin | HTT |
| Medullary carcinoma of the thyroid | Calcitonin | ACal |
| Cardiac arrhythmias, Isolated atrial amyloidosis | Atrial natriuretic factor | AANF |
| Atherosclerosis | Apolipoprotein AI | AApoA1 |
| Rheumatoid arthritis | Serum amyloid A | AA |
| Aortic medial amyloid | Medin | AMed |
| Prolactinomas | Prolactin | APro |
| Familial amyloid polyneuropathy | Transthyretin | ATTR |
| Hereditary non-neuropathic systemic amyloidosis | Lysozyme | ALys |
| Dialysis related amyloidosis | Beta 2 microglobulin | Aβ2M |
| Finnish amyloidosis | Gelsolin | AGel |
| Lattice corneal dystrophy | Keratoepithelin | AKer |
| Cerebral amyloid angiopathy | Beta amyloid[15] | Aβ |
| Cerebral amyloid angiopathy (Icelandic type) | Cystatin | ACys |
| systemic AL amyloidosis | Immunoglobulin light chain AL | AL |
| Sporadic Inclusion Body Myositis | S-IBM | none |
| Age-related macular degeneration (AMD) | Beta amyloid | Aβ |
| Cerebrovascular dementia | Cerebrovascular amyloid | CVA |

Subjects/patients amenable to treatment using the methods described herein include individuals at risk of disease (e.g., a pathology characterized by amyloid plaque formation such as MCI) but not showing symptoms, as well as subjects presently showing symptoms. It is known that the risk of MCI and later Alzheimer's disease generally increases with age. Accordingly, in asymptomatic subjects with no other known risk factors, in certain embodiments, prophylactic application is contemplated for subjects over 50 years of age, or subjects over 55 years of age, or subjects over 60 years of age, or subjects over 65 years of age, or subjects over 70 years of age, or subjects over 75 years of age, or subjects over 80 years of age, in particular to prevent or slow the onset or ultimate severity of mild cognitive impairment (MCI), and/or to slow or prevent the progression from MCI to early stage Alzheimer's disease (AD).

In certain embodiments, the methods described herein present methods are especially useful for individuals who do have a known genetic risk of Alzheimer's disease (or other amyloidogenic pathologies), whether they are asymptomatic or showing symptoms of disease. Such individuals include those having relatives who have experienced MCI or AD (e.g., a parent, a grandparent, a sibling), and those whose risk is determined by analysis of genetic or biochemical markers. Genetic markers of risk toward Alzheimer's disease include, for example, olfactory impairment or dysfunction, mutations in the APP gene, particularly mutations at position 717 and positions 670 and 671 referred to as the Hardy and Swedish mutations respectively (see Hardy (1997) *Trends. Neurosci.* 20: 154-159). Other markers of risk include mutations in the presenilin genes (PS1 and PS2), family history of AD, having the familial Alzheimer's disease (FAD) mutation, the APOE ε4 allele, hypercholesterolemia or atherosclerosis. Further susceptibility genes for the development of Alzheimer's disease are reviewed, e.g., in Sleegers, et al. (2010) *Trends Genet.* 26(2): 84-93.

In some embodiments, the subject is asymptomatic but has familial and/or genetic risk factors for developing MCI or Alzheimer's disease. In asymptomatic patients, treatment can begin at any age (e.g., 20, 30, 40, 50 years of age). Usually, however, it is not necessary to begin treatment until a patient reaches at least about 40, 50, 60 or 70 years of age.

In some embodiments, the subject is asymptomatic for cognitive impairment but is exhibiting olfactory dysfunction. For example, the subject would fail or may have failed an olfactory challenge test. Numerous olfactory challenge tests are known in the art, and can be used to detect if an asymptomatic individual or an individual exhibiting symptoms of mild cognitive impairment (MCI) is at risk of developing Alzheimer's disease. Such olfactory challenge tests include without limitation the Alberta Smell Test (AST) (Heyanka, et al., *Appl Neuropsychol Adult*. (2014) 21(3): 176-82); so-called "Sniffin' Sticks" (Neumann, et al., Clin Otolaryngol. 2012 February; 37(1):23-7; available for purchase from USneurologicals.com); Short Smell Test (SST) (Streit et al. *BMC Geriatrics* (2015) 15:90); Cross-Cultural Smell Identification Test (CC-SIT) (Scalco, et al., *Int J Geriatr Psychiatry*. (2009) 24(4):376-81); University of Pennsylvania Smell Identification Test (UPSIT) (Schofield et al. *BMC Neurology* (2012) 12:24 and Velayudhan, et al., *Int Psychogeriatr*. (2013) 25(7):1157-66).

In some embodiments, the subject is exhibiting symptoms, for example, of mild cognitive impairment (MCI) or Alzheimer's disease (AD). Individuals presently suffering from Alzheimer's disease can be recognized from characteristic dementia, as well as the presence of risk factors described above. In addition, a number of diagnostic tests are available for identifying individuals who have AD. These include measurement of CSF Tau, phospho-tau (pTau), Aβ42 levels and C-terminally cleaved APP fragment (APPneo). Elevated total-Tau (tTau), phospho-Tau (pTau), APPneo, soluble Aβ40, pTau/Aβ42 ratio and tTau/Aβ42 ratio, and decreased Aβ42 levels, Aβ42/Aβ40 ratio, Aβ42/Aβ38 ratio, sAPPα levels, sAPPα/sAPPβ ratio, sAPPα/A (340 ratio, and sAPPα/Aβ42 ratio signify the presence of AD. In some embodiments, the subject or patient is diagnosed as having MCI. Increased levels of neural thread protein (NTP) in urine and/or increased levels of α2-macroglobulin (α2M) and/or complement factor H (CFH) in plasma are also biomarkers of MCI and/or AD. See, Anoop, et al., *Int J Alzheimers Dis*. (2010) Jun. 23, 2010. pii: 606802

(PMID 20721349). In some embodiments, the subject or patient is diagnosed as having Alzheimer's disease (e.g., early-stage, mid-stage or late-stage).

In certain embodiments, subjects amenable to treatment may have age-associated memory impairment (AAMI), or mild cognitive impairment (MCI). The methods described herein are particularly well-suited to the treatment of MCI. In such instances, the methods can reduce one or more symptoms characteristic of MCI and/or delay or prevent the progression from MCI to early-, mid- or late-stage Alzheimer's disease or reduce the ultimate severity of the disease.

Mild Cognitive Impairment (MCI)

Mild cognitive impairment (MCI, also known as incipient dementia, or isolated memory impairment) is a diagnosis given to individuals who have cognitive impairments beyond that expected for their age and education, but that typically do not interfere significantly with their daily activities (see, e.g., Petersen et al. (1999) Arch. Neurol. 56(3): 303-308). It is considered in many instances to be a boundary or transitional stage between normal aging and dementia. Although MCI can present with a variety of symptoms, when memory loss is the predominant symptom it is termed "amnestic MCI" and is frequently seen as a risk factor for Alzheimer's disease (see, e.g., Grundman et al. (2004) Arch. Neurol. 61(1): 59-66; and on the internet at en.wikipedia.org/wiki/Mild_cognitive_impairment—cite_note-Grundman-1). When individuals have impairments in domains other than memory it is often classified as non-amnestic single- or multiple-domain MCI and these individuals are believed to be more likely to convert to other dementias (e.g. dementia with Lewy bodies). There is evidence suggesting that while amnestic MCI patients may not meet neuropathologic criteria for Alzheimer's disease, patients may be in a transitional stage of evolving Alzheimer's disease; patients in this hypothesized transitional stage demonstrated diffuse amyloid in the neocortex and frequent neurofibrillary tangles in the medial temporal lobe (see, e.g., Petersen et al. (2006) Arch. Neurol. 63(5): 665-72).

The diagnosis of MCI typically involves a comprehensive clinical assessment including clinical observation, neuroimaging, blood tests and neuropsychological testing. A similar assessment is usually given for diagnosis of Alzheimer's disease. There is emerging evidence that magnetic resonance imaging can observe deterioration, including progressive loss of gray matter in the brain, from mild cognitive impairment to full-blown Alzheimer disease (see, e.g., Whitwell et al. (2008) Neurology 70(7): 512-520). A technique known as PiB PET imaging is used to clearly show the sites and shapes of beta amyloid deposits in living subjects using a C11 tracer that binds selectively to such deposits (see, e.g., Jack et al. (2008) Brain 131(Pt 3): 665-680).

Presently, MCI is typically diagnosed when there is 1) Evidence of memory impairment; 2) Preservation of general cognitive and functional abilities; and 3) Absence of diagnosed dementia.

MCI and stages of Alzheimer's disease can be identified/categorized, in part by Clinical Dementia Rating (CDR) scores. The CDR is a five point scale used to characterize six domains of cognitive and functional performance applicable to Alzheimer disease and related dementias: Memory, Orientation, Judgment & Problem Solving, Community Affairs, Home & Hobbies, and Personal Care. The necessary information to make each rating is obtained through a semi-structured interview of the patient and a reliable informant or collateral source (e.g., family member).

The CDR table provides descriptive anchors that guide the clinician in making appropriate ratings based on interview data and clinical judgment. In addition to ratings for each domain, an overall CDR score may be calculated through the use of an algorithm. This score is useful for characterizing and tracking a patient's level of impairment/dementia: 0=Normal; 0.5=Very Mild Dementia; 1=Mild Dementia; 2=Moderate Dementia; and 3=Severe Dementia. An illustrative CDR table is shown in Table 2.

TABLE 2

Illustrative clinical dementia rating (CDR) table.

| | Impairment: | | | | |
|---|---|---|---|---|---|
| | None | Questionable | Mild | Moderate | Severe |
| | | | CDR: | | |
| | 0 | 0.5 | 1 | 2 | 3 |
| Memory | No memory loss or slight inconsistent forgetfulness | Consistent slight forgetfulness; partial recollection of events' "benign" forgetfulness | Moderate memory loss; more marked for recent events; defect interferes with everyday activities | Severe memory loss; only highly learned material retained; new material rapidly lost | Severe memory loss; only fragments remain |
| Orientation | Fully oriented | Fully oriented except for slight difficulty with time relationships | Moderate difficulty with time relationships; oriented for place at examination; may have geographic disorientation elsewhere | Severe difficulty with time relationships; usually disoriented to time, often to place. | Oriented to person only |

TABLE 2-continued

Illustrative clinical dementia rating (CDR) table.

| | Impairment: | | | | |
|---|---|---|---|---|---|
| | None | Questionable | Mild | Moderate | Severe |
| | | | CDR: | | |
| | 0 | 0.5 | 1 | 2 | 3 |
| Judgment & Problem Solving | Solves everyday problems & handles business & financial affairs well; judgment good in relation to past performance | Slight impairment in solving problems, similarities, and differences | Moderate difficulty in handling problems, similarities and differences; social judgment usually maintained | Severely impaired in handling problems, similarities and differences; social judgment usually impaired | Unable to make judgments or solve problems |
| Community Affairs | Independent function at usual level in job, shopping, volunteer, and social groups | Slight impairment in these activities | Unable to function independently at these activities although may still be engaged in some; appears normal to casual inspection | No pretense of independent function outside of home | |
| | | | | Appears well enough to be taken to functions outside a family home | Appears too ill to be taken to functions outside a family home. |
| Home and Hobbies | Life at home, hobbies, and intellectual interests well maintained | Life at home, hobbies, and intellectual interests slightly impaired | Mild but definite impairment of function at home; more difficult chores abandoned; more complicated hobbies and interests abandoned | Only simple chores preserved; very restricted interests, poorly maintained | No significant function in home |
| Personal Care | Fully capable of self-care | | Needs prompting | Requires assistance in dressing, hygiene, keeping of personal effects | Requires much help with personal care; frequent incontinence |

A CDR rating of ~0.5 or ~0.5 to 1.0 is often considered clinically relevant MCI. Higher CDR ratings can be indicative of progression into Alzheimer's disease.

In various embodiments administration of one or more agents described herein (e.g., one or more of antibiotics useful to treat gram-negative bacteria and/or TLR4 inhibitors and/or antibodies or fragments thereof against a gram-negative bacterial antigen and/or a gram-negative bacteria immunogenic antigen) is deemed effective when there is a reduction in the CSF of levels of one or more components selected from the group consisting of Tau, phospho-Tau (pTau), APPneo, soluble Aβ40, soluble Aβ42, and/or Aβ42/Aβ40 ratio, and/or when there is a reduction of the plaque load in the brain of the subject, and/or when there is a reduction in the rate of plaque formation in the brain of the subject, and/or when there is an improvement in the cognitive abilities of the subject, and/or when there is a perceived improvement in quality of life by the subject, and/or when there is a significant reduction in clinical dementia rating (CDR), and/or when the rate of increase in clinical dementia rating is slowed or stopped and/or when the progression from MCI to early stage AD is slowed or stopped.

In some embodiments, a diagnosis of MCI can be determined by considering the results of several clinical tests. For example, Grundman, et al., Arch Neurol (2004) 61:59-66 report that a diagnosis of MCI can be established with clinical efficiency using a simple memory test (paragraph recall) to establish an objective memory deficit, a measure of general cognition (Mini-Mental State Exam (MMSE), discussed in greater detail below) to exclude a broader cognitive decline beyond memory, and a structured clinical interview (CDR) with patients and caregivers to verify the patient's memory complaint and memory loss and to ensure that the patient was not demented. Patients with MCI perform, on average, less than 1 standard deviation (SD) below normal on nonmemorycognitive measures included in the battery. Tests of learning, attention, perceptual speed, category fluency, and executive function may be impaired in patients with MCI, but these are far less prominent than the memory deficit.

Alzheimer's Disease (AD).

In certain embodiments, the methods described herein are useful in preventing or slowing the onset of Alzheimer's disease (AD), in reducing the severity of AD when the subject has transitioned to clinical AD diagnosis, and/or in mitigating one or more symptoms of Alzheimer's disease.

In particular, where the Alzheimer's disease is early stage, the methods can reduce or eliminate one or more symptoms characteristic of AD and/or delay or prevent the progression from MCI to early or later stage Alzheimer's disease.

Individuals presently suffering from Alzheimer's disease can be recognized from characteristic dementia, as well as the presence of risk factors described above. In addition, a number of diagnostic tests are available for identifying individuals who have AD. Individuals presently suffering from Alzheimer's disease can be recognized from characteristic dementia, as well as the presence of risk factors described above. In addition, a number of diagnostic tests are available for identifying individuals who have AD. These include measurement of CSF Tau, phospho-tau (pTau), sAPPα, sAPPβ, Aβ40, Aβ42 levels and/or C terminally cleaved APP fragment (APPneo). Elevated Tau, pTau, sAPPβ and/or APPneo, and/or decreased sAPPα, soluble Aβ40 and/or soluble Aβ42 levels, particularly in the context of a differential diagnosis, can signify the presence of AD.

In certain embodiments subjects amenable to treatment may have Alzheimer's disease. Individuals suffering from Alzheimer's disease can also be diagnosed by Alzheimer's disease and Related Disorders Association (ADRDA) criteria. The NINCDS-ADRDA Alzheimer's Criteria were proposed in 1984 by the National Institute of Neurological and Communicative Disorders and Stroke and the Alzheimer's Disease and Related Disorders Association (now known as the Alzheimer's Association) and are among the most used in the diagnosis of Alzheimer's disease (AD). McKhann, et al. (1984) *Neurology* 34(7): 939-44. According to these criteria, the presence of cognitive impairment and a suspected dementia syndrome should be confirmed by neuropsychological testing for a clinical diagnosis of possible or probable AD. The NINCDS-ADRDA Alzheimer's Criteria specify eight cognitive domains that may be impaired in AD: memory, language, perceptual skills, attention, constructive abilities, orientation, problem solving and functional abilities). These criteria have shown good reliability and validity.

Baseline evaluations of patient function can made using classic psychometric measures, such as the Mini-Mental State Exam (MMSE) (Folstein et al. (1975) *J. Psychiatric Research* 12 (3): 189-198), and the Alzheimer's Disease Assessment Scale (ADAS), which is a comprehensive scale for evaluating patients with Alzheimer's Disease status and function (see, e.g., Rosen, et al. (1984) *Am. J. Psychiatr.,* 141: 1356-1364). These psychometric scales provide a measure of progression of the Alzheimer's condition. Suitable qualitative life scales can also be used to monitor treatment. The extent of disease progression can be determined using a Mini-Mental State Exam (MMSE) (see, e.g., Folstein, et al. supra). Any score greater than or equal to 25 points (out of 30) is effectively normal (intact). Below this, scores can indicate severe (<9 points), moderate (10-20 points) or mild (21-24 points) Alzheimer's disease.

Alzheimer's disease can be broken down into various stages including: 1) Moderate cognitive decline (Mild or early-stage Alzheimer's disease), 2) Moderately severe cognitive decline (Moderate or mid-stage Alzheimer's disease), 3) Severe cognitive decline (Moderately severe or mid-stage Alzheimer's disease), and 4) Very severe cognitive decline (Severe or late-stage Alzheimer's disease) as shown in Table 3.

TABLE 3

Illustrative stages of Alzheimer's disease.

Moderate Cognitive Decline (Mild or early stage AD)

At this stage, a careful medical interview detects clear-cut deficiencies in the following areas:
Decreased knowledge of recent events.
Impaired ability to perform challenging mental arithmetic. For example, to count backward from 100 by 7s.
Decreased capacity to perform complex tasks, such as marketing, planning dinner for guests, or paying bills and managing finances.
Reduced memory of personal history.
The affected individual may seem subdued and withdrawn, especially in socially or mentally challenging situations.
Moderately severe cognitive decline
(Moderate or mid-stage Alzheimer's disease)

Major gaps in memory and deficits in cognitive function emerge. Some assistance with day-to-day activities becomes essential. At this stage, individuals may:
Be unable during a medical interview to recall such important details as their current address, their telephone number, or the name of the college or
high school from which they graduated.
Become confused about where they are or about the date, day of the week or season.
Have trouble with less challenging mental arithmetic; for example, counting backward from 40 by 4s or from 20 by 2s.
Need help choosing proper clothing for the season or the occasion.
Usually retain substantial knowledge about themselves and know their own name and the names of their spouse or children.
Usually require no assistance with eating or using the toilet.
Severe cognitive decline
(Moderately severe or mid-stage Alzheimer's disease)

Memory difficulties continue to worsen, significant personality changes may emerge, and affected individuals need extensive help with daily activities. At this stage, individuals may:
Lose most awareness of recent experiences and events as well as of their surroundings.
Recollect their personal history imperfectly, although they generally recall their own name.
Occasionally forget the name of their spouse or primary caregiver but generally can distinguish familiar from unfamiliar faces.
Need help getting dressed properly; without supervision, may make such errors as putting pajamas over daytime clothes or shoes on wrong feet.
Experience disruption of their normal sleep/waking cycle.
Need help with handling details of toileting (flushing toilet, wiping and disposing of tissue properly).
Have increasing episodes of urinary or fecal incontinence.
Experience significant personality changes and behavioral symptoms, including suspiciousness and delusions (for example, believing that their caregiver is an impostor); hallucinations (seeing or hearing things that are not really there); or compulsive, repetitive behaviors such as hand-wringing or tissue shredding.
Tend to wander and become lost.
Very severe cognitive decline
(Severe or late-stage Alzheimer's disease)

This is the final stage of the disease when individuals lose the ability to respond to their environment, the ability to speak, and, ultimately, the ability to control movement.
Frequently individuals lose their capacity for recognizable speech, although words or phrases may occasionally be uttered.
Individuals need help with eating and toileting and there is general incontinence.
Individuals lose the ability to walk without assistance, then the ability to sit without support, the ability to smile, and the ability to hold their head up.
Reflexes become abnormal and muscles grow rigid. Swallowing is impaired.

In various embodiments administration of one or more agents described herein to subjects diagnosed with Alzheimer's disease is deemed effective when the there is a reduction in the CSF of levels of one or more components selected from the group consisting of Tau, phospho-Tau (pTau), APPneo, soluble Aβ40, soluble Aβ42, and/or and Aβ42/

Aβ40 ratio, and/or when there is a reduction of the plaque load in the brain of the subject, and/or when there is a reduction in the rate of plaque formation in the brain of the subject, and/or when there is an improvement in the cognitive abilities of the subject, and/or when there is a perceived improvement in quality of life by the subject, and/or when there is a significant reduction in clinical dementia rating (CDR) of the subject, and/or when the rate of increase in clinical dementia rating is slowed or stopped and/or when the progression of AD is slowed or stopped (e.g., when the transition from one stage to another as listed in Table 3 is slowed or stopped).

In certain embodiments, subjects amenable to the present methods generally are free of a neurological disease or disorder other than Alzheimer's disease. For example, in certain embodiments, the subject does not have and is not at risk of developing a neurological disease or disorder such as Parkinson's disease, and/or schizophrenia, and/or psychosis.

In certain embodiments, subjects amenable to the present methods generally are free of a bacterial infection, including a gram negative bacterial infection, outside of the brain or outside of the central nervous system.

3. Methods of Detecting AD-Associated Gram Negative Bacteria

In certain embodiments, the subject has tested positive for the presence of AD-associated gram-negative bacteria in a CNS tissue, e.g., in a cerebral spinal fluid (CSF) sample or brain tissue sample. The subject may additionally test positive for the presence of the same gram-negative bacteria in a second non-CNS biological sample, e.g., tears, saliva, a buccal swab, a gum swab, sputum, urine, a fecal sample.

In some embodiments, the methods for identifying AD-associated gram-negative bacterial infection entail detecting in one or more biological samples from the subject an approximately 500 bp PCR product of bacterial galactose-1-phosphate uridylyltransferase (GalT)—UDP-galactose-4-epimerase (GalE)—molybdate ABC transporter ATP-binding protein (modF) DNA amplified using forward primer (5'→3') CAGAATCCATTGCCCGGTGA and reverse sequence (5'→3') CCATGTCACACTTTTCGCATCT. Further sequencing of the amplified PCR product can further direct to the source of Gram-negative bacteria, e.g., the original source of infection, e.g., *Porphyromonas gingivalis* from the gums; *E. coli/Salmonella/Shigella* from clinical gastrointestinal infections; or Gram-negative bacteria from infections in other organs In some embodiments, the methods for identifying AD-associated gram-negative bacterial infection entail detecting in one or more biological samples from the subject "rough" LPS, which lacks a side chain of O antigen.

4. Methods of Treatment

In some embodiments, the methods of mitigating, reversing or eliminating in a subject one or more symptoms associated with cognitive impairment associated with amyloid deposits in the brain comprise delivering to the brain of the subject one or more compounds that prevent or delay or interfere with growth of or kill gram negative bacteria, in an amount sufficient to mitigate, reverse or eliminate the one or more symptoms of said cognitive impairment. In varying embodiments, the one or more compounds include an antibiotic useful to treat a gram-negative bacterial infection, an inhibitor of a Toll-Like Receptor 4 (TLR4), and/or an antibody or fragment thereof that specifically binds to an immunogenic antigen of a gram negative bacterium.

a. Brain Targeted Compounds

In order to enhance delivery to the brain, the one or more compounds can be co-administered with, conjugated to or encapsulated within an agent that facilitate transport across the blood-brain-barrier. Strategies and agents useful for facilitating delivery across the blood-brain-barrier are known in the art and can be employed for delivering to the brain compounds targeting gram negative bacteria (e.g., *E. coli*). Current strategies for delivering active agents across the blood-brain barrier and that find use in the present methods include without limitation nanocarriers and nanoparticles (Tam, et al., *Int J Pharm*. (2016) 515(1-2):331-342; Zhao, et al., *Nanoscale Res Lett*. 2016 December; 11(1):451; Song, et al., *Mol Pharm*. (2016) Oct. 4; PMID: 27700119; Lalatsa, et al., *Int Rev Neurobiol*. 2016; 130:115-53; Kundo, et al., *ACS Chem Neurosci*. (2016) Oct. 3; PMID: 27642670); functionalized carbon nanotubes (Costa, et al., *J Control Release*. (2016) 241:200-219); nanowires (Sharma, et al., *CNS Neurol Disord Drug Targets*. 2016 Aug. 19; PMID: 27538949); viral vectors (Fu, et al., *Curr Opin Virol*. (2016) 21:87-92); liposomes and exosomes (Tremmel, et al., *Int J Pharm*. (2016) 512(1):87-95; Sánchez-Purrà, et al., *Int J Pharm*. (2016) 511(2):946-56; Bender, et al. *J Vis Exp*. (2016) Jul. 23; (113). doi: 10.3791/54106; Ha, et al., *Acta Pharm Sin B*. (2016) 6(4):287-96; Alvarez-Erviti, et al., *Nature Biotechnology* (2011) 29(4):341-345; Yellon and Davidson, *Circ Res*. (2014) 114:325-332; Xin, et al., *Front Cell Neurosci*. (2014) 8:377); dendrimers (Jiang, et al, *Colloids Surf B Biointerfaces* (2016) 147:242-9) and ultrasound (Park, et al., *J Control Release*. (2016) Oct. 11. pii: S0168-3659(16)30955-5; Airan, et al., *Mol Imaging Biol*. (2016) Aug. 1; PMID: 27481359). In varying embodiments, the one or more compounds can be conjugated to or administered in conjunction with a peptide that promotes transcytosis and traversal of the blood-brain barrier. Illustrative peptides include without limitation Angiopep-2 (Li, et al., *Oncotarget*. 2016 Oct. 17. doi: 10.18632; PMID: 27765902); Transferrin (Nanoscale. (2016) 8(37):16662-16669); penetratin (Spencer, et al., *Ann Clin Transl Neurol*. (2016) 3(8):588-606); and M36 fungalysin metalloprotease (WO 2013/036827).

i. Antibiotics Effective Against Gram-Negative Bacteria

In varying embodiments, the compound is an antibiotic effective to treat a gram-negative bacterial (e.g., *E. coli*) infection. Illustrative antibiotics effective against gram-negative bacterial infections include without limitation quinolone antibiotics (e.g., nalidixic acid, ofloxacin, levofloxacin, ciprofloxacin, norfloxacin, enoxacin, lomefloxacin, grepafloxacin, trovafloxacin, sparfloxacin, temafloxacin, moxifloxacin, gatifloxacin, gemifloxacin), beta-lactamases (e.g., penicillin, cloxacillin, dicloxacillin, flucloxacillin, methicillin, nafcillin, oxacillin, temocillin, amoxicillin, ampicillin, mecillinam, carbenicillin, ticarcillin, azlocillin, mezlocillin, piperacillin), aminoglycosides (e.g., amikacin, gentamicin, kanamycin, neomycin, streptomycin, tobramycin), cephalosporins (e.g., cefadroxil, cefazolin, cephalexin, cefaclor, cefoxitin, cefprozil, cefuroxime, loracarbef, cefixime, cefdinir, cefditoren, cefoperazone, cefotaxime, cefpodoxime, cefepime, ceftobiprole), monobactams (e.g., aztreonam, tigemonam, nocardicin A, tabtoxinine β-lactam), carbapenems (e.g., biapenem, doripenem, ertapenem, faropenem, imipenem, meropenem, panipenem, razupenem, tebipenem, thienamycin), tetracycline antibiotics (e.g., tetracycline, chlortetracycline, oxytetracycline, demeclocycline, lymecycline, meclocycline, methacycline, minocycline, rolitetracycline, tigecycline), chloramphenicol, and triamphenicol. Additional antibiotics may find use. Dosing and additional antibiotics effective against gram-negative bacterial infections are discussed, e.g., in 2017 Physicians' Desk Reference, 71st Edition, by PDR Staff, published by PDR Network. Macrolones, which are derived from macrolides and comprise macrocyclic moiety, linker, and either free or esterified quinolone 3-carboxylic group, can also be used in the present methods (Jelid, et al., *Antibiotics* (Basel). (2016) Sep. 1; 5(3). pii: E29).

In varying embodiments, the antibiotic is co-administered with lysozyme and EDTA. Further strategies for potentiation of the efficacy of antibiotics effective against gram-negative bacterial infections, and which can find use in the present methods, are reviewed in Zabawa, et al., *Curr Opin Microbiol.* (2016) October; 33:7-12. In varying embodiments, the antibiotic is conjugated to, encapsulated within or administered in conjunction with an agent that facilitates delivery across the blood-brain barrier, as described above.

ii. Toll-Like Receptor 4 (TLR4) Inhibitors/Antagonists

In varying embodiments, the compound is an inhibitor of Toll-Like Receptor 4 (TLR4) (e.g., "a TLR4 inhibitor). Illustrative TLR4 inhibitors are known in the art, and find use include without limitation:

- tricyclic antidepressants (e.g., Amitriptyline, Butriptyline, Clomipramine, Desipramine, Dosulepin, Doxepin, Imipramine, Iprindole, Lofepramine, Nortriptyline, Protriptyline, Trimipramine);
- tetracyclic antidepressants (e.g., Maprotiline, Mianserin, Mirtazapine, Pirlindole, Setiptiline, Aptazapine, Esmirtazapine, Metralindole, Oxaprotiline, Amoxapine, Ciclazindol, Losindole, Loxapine, Mazindol);
- TAK-242 (resatorvid) (described in Matsunaga, et al., *Molecular Pharmacology* (2011) 79(1):34-41; chemical name: ethyl (6R)-6-[(2-chloro-4-fluorophenyl)sulfamoyl]cyclohexene-1-carboxylate; CAS Number: 243984-11-4);
- cyclobenzaprine (CA Index Name: 1-Propanamine, 3-(5H-dibenzo[a,d]cyclohepten-5-ylidene)-N,N-dimethyl-; CAS Registry Number: 303-53-7);
- Hi histamine receptor antagonists (e.g., ketotifen (chemical name: 4-(1-Methylpiperidin-4-ylidene)-4,9-dihydro-10H-benzo[4,5]cyclohepta[1,2-b]thiophen-10-one; CAS Registry Number: 34580-14-8); Alcaftadine (chemical name: 2-(1-Methylpiperidin-4-ylidene)-4,7-diazatricyclo[8.4.0.0(3,7)]tetradeca-1(14),3,5,10,12-pentaene-6-carbaldehyde; CAS Registry Number: 147084-10-4); Etolotifen (chemical name: 4,9-Dihydro-4-(1-(2-(2-(2-hydroxyethoxy)ethoxy)ethyl)-4-piperidylidene)-10H-benzo(4,5)cyclohepta(1,2-b)thiophen-10-one; CAS Registry Number: 82140-22-5));
- Ibudilast (chemical name: 2-Methyl-1-(2-propan-2-ylpyrazolo[1,5-a]pyridin-3-yl)propan-1-one; CAS Registry No. 50847-11-5);
- naloxone, (+)-naloxone, naltrexone, (+)-naltrexone;
- tapentadol (chemical name: 3-[(1R,2R)-3-(dimethylamino)-1-ethyl-2-methylpropyl]phenol hydrochloride; CAS Registry Number: 175591-09-0);
- *Rhodobacter sphaeroides* Lipopolysaccharide (LPS-RS) and *Bartonella quintana* lipopolysaccharide (LPS) (Malgorzata-Miller, et al., *Sci Rep*. (2016) 6:34221);
- SAHA (a.k.a., suberoylanilide hydroxamic acid or suberanilohydroxamic acid; chemical name: N'-hydroxy-N-phenyloctanediamide; CAS Registry Number: 149647-78-9);
- Sparstolonin B (SsnB), isolated from Chinese herb *Scirpus yagara*, (Liang, et al., J Biol. Chem. (2011) 286 (30):26470-26479 and U.S. Patent Publ. No. US20140303242A1);
- eritoran tetrasodium (McDonald, et al., Mol Med. (2015) 20:639-48; chemical name: tetrasodium; [(2R,3R,4R,5 S,6R)-4-decoxy-5-hydroxy-6-[[(2R,3R,4R,5 S,6R)-4-[(3R)-3-methoxydecoxy]-6-(methoxymethyl)-3-[[(Z)-octadec-11-enoyl]amino]-5-phosphonatooxyoxan-2-yl]oxymethyl]-3-(3-oxotetradecanoylamino)oxan-2-yl] phosphate; CAS Registry Number: 185954-98-7);
- vaccinia virus A46 (Kim, et al., *Protein Sci.* (2014) 23(7):906-14);
- Zhankuic acid A isolated from *Taiwanofungus camphoratus* (Chen, et al., *J Immunol.* (2014) 192(6):2778-86);
- CRX-526 (Lin, et al, *Kidney Int.* (2013) 83(5):887-900; Fort, et al., *J. Immunol.* (2005) 174(10):6416-6423); and
- Propentofylline (chemical name: 3-methyl-1-(5-oxohexyl)-7-propyl-3,7-dihydro-1H-purine-2,6-dione; CAS Registry Number: CAS Number: 55242-55-2).

Additional synthetic and natural small molecule TLR4 antagonists that can find use in the present methods are described in, e.g., De Paola, et al., *Pharmacol Res.* (2016) 103:180-7; Hu, et al, *BMC Neurosci.* (2016) 17(1):22; Bajo, et al., *Alcohol and Alcoholism.* (2016) 51(5):541-8; Švajger, et al., *Eur J Med Chem.* (2013) 70:393-9; Neal, et al., PLoS One. (2013) 8(6):e65779. Dosing and additional TLR4 inhibitor/antagonists are discussed, e.g., in 2016 Physicians' Desk Reference, 70th Edition, by PDR Staff, published by PDR Network. In varying embodiments, the TLR4 inhibitor or antagonist is conjugated to, encapsulated within or administered in conjunction with an agent that facilitates delivery across the blood-brain barrier, as described above.

b. Formulation and Administration i. Formulation

The compounds (e.g., antibiotics effective against gram negative bacteria and/or TLR4 inhibitor/antagonists) and/or an analog thereof can be administered orally, parenterally, (intravenously (IV), intramuscularly (IM), depo-IM, subcutaneously (SQ), and depo-SQ), sublingually, intranasally (inhalation), intrathecally, transdermally (e.g., via transdermal patch), topically, ionophoretically or rectally. Typically the dosage form is selected to facilitate delivery to the brain (e.g., passage through the blood brain barrier). In this context, it is noted that the compounds described herein can be readily delivered to the brain, e.g., using blood-brain-barrier transdelivery strategies described herein and otherwise known in the art. Dosage forms known to those of skill in the art are suitable for delivery of the compound.

Compositions are provided that contain therapeutically effective amounts of the compound. The compounds are preferably formulated into suitable pharmaceutical preparations such as tablets, capsules, or elixirs for oral administration or in sterile solutions or suspensions for parenteral administration. Typically the compounds described above are formulated into pharmaceutical compositions using techniques and procedures well known in the art.

These active agents (e.g., antibiotics effective against gram negative bacteria and/or TLR4 inhibitor/antagonists and/or analogs thereof) can be administered in the "native" form or, if desired, in the form of salts, esters, amides, prodrugs, derivatives, and the like, provided the salt, ester, amide, prodrug or derivative is suitable pharmacologically effective, e.g., effective in the present method(s). Salts, esters, amides, prodrugs and other derivatives of the active agents can be prepared using standard procedures known to those skilled in the art of synthetic organic chemistry and described, for example, by March (1992) Advanced Organic Chemistry; Reactions, Mechanisms and Structure, 4th Ed. N.Y. Wiley-Interscience.

Methods of formulating such derivatives are known to those of skill in the art. For example, the disulfide salts of a number of delivery agents are described in PCT Publication WO 2000/059863 which is incorporated herein by reference. Similarly, acid salts of therapeutic peptides, peptoids, or other mimetics, and can be prepared from the free base using conventional methodology that typically involves reaction with a suitable acid. Generally, the base form of the drug is dissolved in a polar organic solvent such as methanol or ethanol and the acid is added thereto. The resulting salt either precipitates or can be brought out of solution by addition of a less polar solvent. Suitable acids for preparing acid addition salts include, but are not limited to both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, orotic acid, and the like, as well as inorganic acids, e.g., hydrochloric acid, hydrobromic acid, sulfuric acid, nitric acid, phosphoric acid, and the like. An acid addition salt can be reconverted to the free base by treatment with a suitable base. Certain particularly preferred acid addition salts of the active agents herein include halide salts, such as may be prepared using hydrochloric or hydrobromic acids. Conversely, preparation of basic salts of the active agents of this invention are prepared in a similar manner using a pharmaceutically acceptable base such as sodium hydroxide, potassium hydroxide, ammonium hydroxide, calcium hydroxide, trimethylamine, or the like. In certain embodiments basic salts include alkali metal salts, e.g., the sodium salt, and copper salts.

For the preparation of salt forms of basic drugs, the pKa of the counterion is preferably at least about 2 pH lower than the pKa of the drug. Similarly, for the preparation of salt forms of acidic drugs, the pKa of the counterion is preferably at least about 2 pH higher than the pKa of the drug. This permits the counterion to bring the solution's pH to a level lower than the pHmax to reach the salt plateau, at which the solubility of salt prevails over the solubility of free acid or base. The generalized rule of difference in pKa units of the ionizable group in the active pharmaceutical ingredient (API) and in the acid or base is meant to make the proton transfer energetically favorable. When the pKa of the API and counterion are not significantly different, a solid complex may form but may rapidly disproportionate (e.g., break down into the individual entities of drug and counterion) in an aqueous environment.

Preferably, the counterion is a pharmaceutically acceptable counterion. Suitable anionic salt forms include, but are not limited to acetate, benzoate, benzylate, bitartrate, bromide, carbonate, chloride, citrate, edetate, edisylate, estolate, fumarate, gluceptate, gluconate, hydrobromide, hydrochloride, iodide, lactate, lactobionate, malate, maleate, mandelate, mesylate, methyl bromide, methyl sulfate, mucate, napsylate, nitrate, pamoate (embonate), phosphate and diphosphate, salicylate and disalicylate, stearate, succinate, sulfate, tartrate, tosylate, triethiodide, valerate, and the like, while suitable cationic salt forms include, but are not limited to aluminum, benzathine, calcium, ethylene diamine, lysine, magnesium, meglumine, potassium, procaine, sodium, tromethamine, zinc, and the like.

In various embodiments preparation of esters typically involves functionalization of hydroxyl and/or carboxyl groups that are present within the molecular structure of the active agent. In certain embodiments, the esters are typically acyl-substituted derivatives of free alcohol groups, e.g., moieties that are derived from carboxylic acids of the formula RCOOH where R is alky, and preferably is lower alkyl. Esters can be reconverted to the free acids, if desired, by using conventional hydrogenolysis or hydrolysis procedures.

Amides can also be prepared using techniques known to those skilled in the art or described in the pertinent literature. For example, amides may be prepared from esters, using suitable amine reactants, or they may be prepared from an anhydride or an acid chloride by reaction with ammonia or a lower alkyl amine.

About 1 to 1000 mg of a compound or mixture of the compound (e.g., antibiotics effective against gram negative bacteria and/or TLR4 inhibitor/antagonists) or a physiologically acceptable salt or ester is compounded with a physiologically acceptable vehicle, carrier, excipient, binder, preservative, stabilizer, flavor, etc., in a unit dosage form as called for by accepted pharmaceutical practice. The amount of active substance in those compositions or preparations is such that a suitable dosage in the range indicated is obtained. The compositions are preferably formulated in a unit dosage form, each dosage containing from about 1-1000 mg, 2-800 mg, 5-500 mg, 10-400 mg, 50-200 mg, e.g., about 5 mg, 10 mg, 15 mg, 20 mg, 25 mg, 30 mg, 35 mg, 40 mg, 45 mg, 50 mg, 60 mg, 70 mg, 80 mg, 90 mg, 100 mg, 200 mg, 300 mg, 400 mg, 500 mg, 600 mg, 700 mg, 800 mg, 900 mg or 1000 mg of the active ingredient. The term "unit dosage from" refers to physically discrete units suitable as unitary dosages for human subjects and other mammals, each unit containing a predetermined quantity of active material calculated to produce the desired therapeutic effect, in association with a suitable pharmaceutical excipient.

To prepare compositions, the compound is mixed with a suitable pharmaceutically acceptable carrier. Upon mixing or addition of the compound(s), the resulting mixture may be a solution, suspension, emulsion, or the like. Liposomal suspensions may also be suitable as pharmaceutically acceptable carriers. These may be prepared according to methods known to those skilled in the art. The form of the resulting mixture depends upon a number of factors, including the intended mode of administration and the solubility of the compound in the selected carrier or vehicle. The effective concentration is sufficient for lessening or ameliorating at least one symptom of the disease, disorder, or condition treated and may be empirically determined.

Pharmaceutical carriers or vehicles suitable for administration of the compounds provided herein include any such carriers known to those skilled in the art to be suitable for the particular mode of administration. In addition, the active materials can also be mixed with other active materials that do not impair the desired action, or with materials that supplement the desired action, or have another action. The compounds may be formulated as the sole pharmaceutically active ingredient in the composition or may be combined with other active ingredients.

Where the compounds exhibit insufficient solubility, methods for solubilizing may be used. Such methods are known and include, but are not limited to, using cosolvents such as dimethylsulfoxide (DMSO), using surfactants such as Tween™ and dissolution in aqueous sodium bicarbonate. Derivatives of the compounds, such as salts or prodrugs may also be used in formulating effective pharmaceutical compositions.

The concentration of the compound is effective for delivery of an amount upon administration that lessens or ameliorates at least one symptom of the disorder for which the compound is administered and/or that is effective in a prophylactic context. Typically, the compositions are formulated for single dosage (e.g., daily) administration.

The compounds may be prepared with carriers that protect them against rapid elimination from the body, such as time-release formulations or coatings. Such carriers include controlled release formulations, such as, but not limited to, microencapsulated delivery systems. The active compound is included in the pharmaceutically acceptable carrier in an amount sufficient to exert a therapeutically useful effect in the absence of undesirable side effects on the patient treated. The therapeutically effective concentration may be determined empirically by testing the compounds in known in vitro and in vivo model systems for the treated disorder. A therapeutically or prophylactically effective dose can be determined by first administering a low dose, and then incrementally increasing until a dose is reached that achieves the desired effect with minimal or no undesired side effects.

In various embodiments, the compounds and/or analogs thereof can be enclosed in multiple or single dose containers. The enclosed compounds and compositions can be provided in kits, for example, including component parts that can be assembled for use. For example, a compound inhibitor in lyophilized form and a suitable diluent may be provided as separated components for combination prior to use. A kit may include a compound inhibitor and a second therapeutic agent for co-administration. The inhibitor and second therapeutic agent may be provided as separate component parts. A kit may include a plurality of containers, each container holding one or more unit dose of the compounds. The containers are preferably adapted for the desired mode of administration, including, but not limited to tablets, gel capsules, sustained-release capsules, and the like for oral administration; depot products, pre-filled syringes, ampules, vials, and the like for parenteral administration; and patches, medipads, creams, and the like for topical administration.

The concentration and/or amount of active compound in the drug composition will depend on absorption, inactivation, and excretion rates of the active compound, the dosage schedule, and amount administered as well as other factors known to those of skill in the art.

The active ingredient may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

If oral administration is desired, the compound can be provided in a formulation that protects it from the acidic environment of the stomach. For example, the composition can be formulated in an enteric coating that maintains its integrity in the stomach and releases the active compound in the intestine. The composition may also be formulated in combination with an antacid or other such ingredient.

Oral compositions will generally include an inert diluent or an edible carrier and may be compressed into tablets or enclosed in gelatin capsules. For the purpose of oral therapeutic administration, the active compound or compounds can be incorporated with excipients and used in the form of tablets, capsules, or troches. Pharmaceutically compatible binding agents and adjuvant materials can be included as part of the composition.

In various embodiments, the tablets, pills, capsules, troches, and the like can contain any of the following ingredients or compounds of a similar nature: a binder such as, but not limited to, gum tragacanth, acacia, corn starch, or gelatin; an excipient such as microcrystalline cellulose, starch, or lactose; a disintegrating agent such as, but not limited to, alginic acid and corn starch; a lubricant such as, but not limited to, magnesium stearate; a gildant, such as, but not limited to, colloidal silicon dioxide; a sweetening agent such as sucrose or saccharin; and a flavoring agent such as peppermint, methyl salicylate, or fruit flavoring.

When the dosage unit form is a capsule, it can contain, in addition to material of the above type, a liquid carrier such as a fatty oil. In addition, dosage unit forms can contain various other materials, which modify the physical form of the dosage unit, for example, coatings of sugar and other enteric agents. The compounds can also be administered as a component of an elixir, suspension, syrup, wafer, chewing gum or the like. A syrup may contain, in addition to the active compounds, sucrose as a sweetening agent and certain preservatives, dyes and colorings, and flavors.

The active materials can also be mixed with other active materials that do not impair the desired action, or with materials that supplement the desired action.

Solutions or suspensions used for parenteral, intradermal, subcutaneous, or topical application can include any of the following components: a sterile diluent such as water for injection, saline solution, fixed oil, a naturally occurring vegetable oil such as sesame oil, coconut oil, peanut oil, cottonseed oil, and the like, or a synthetic fatty vehicle such as ethyl oleate, and the like, polyethylene glycol, glycerine, propylene glycol, or other synthetic solvent; antimicrobial agents such as benzyl alcohol and methyl parabens; antioxidants such as ascorbic acid and sodium bisulfite; chelating agents such as ethylenediaminetetraacetic acid (EDTA); buffers such as acetates, citrates, and phosphates; and agents for the adjustment of tonicity such as sodium chloride and dextrose. Parenteral preparations can be enclosed in ampoules, disposable syringes, or multiple dose vials made of glass, plastic, or other suitable material. Buffers, preservatives, antioxidants, and the like can be incorporated as required.

Where administered intravenously, suitable carriers include physiological saline, phosphate buffered saline (PBS), and solutions containing thickening and solubilizing agents such as glucose, polyethylene glycol, polypropyleneglycol, and mixtures thereof. Liposomal suspensions including tissue-targeted liposomes may also be suitable as pharmaceutically acceptable carriers. These may be prepared according to methods known for example, as described in U.S. Pat. No. 4,522,811.

The active compounds may be prepared with carriers that protect the compound against rapid elimination from the body, such as time-release formulations or coatings. Such carriers include controlled release formulations, such as, but not limited to, implants and microencapsulated delivery systems, and biodegradable, biocompatible polymers such as collagen, ethylene vinyl acetate, polyanhydrides, polyglycolic acid, polyorthoesters, polylactic acid, and the like. Methods for preparation of such formulations are known to those skilled in the art.

ii. Routes of Administration and Dosing

In various embodiments, the compounds and/or analogs thereof can be administered orally, parenterally (IV, IM, depo-IM, SQ, and depo-SQ), sublingually, intranasally (inhalation), intrathecally, transdermally (e.g., via transdermal patch), topically, or rectally. Dosage forms known to those skilled in the art are suitable for delivery of the compounds and/or analogs thereof.

In various embodiments, the compounds and/or analogs thereof may be administered enterally or parenterally. When administered orally, the compounds can be administered in usual dosage forms for oral administration as is well known to those skilled in the art. These dosage forms include the usual solid unit dosage forms of tablets and capsules as well as liquid dosage forms such as solutions, suspensions, and elixirs. When the solid dosage forms are used, it is preferred that they be of the sustained release type so that the compound needs to be administered only once or twice daily.

The oral dosage forms can be administered to the patient 1, 2, 3, or 4 times daily. It is preferred that the compound be administered either three or fewer times, more preferably once or twice daily. Hence, it is preferred that the compound be administered in oral dosage form. It is preferred that whatever oral dosage form is used, that it be designed so as to protect the compound from the acidic environment of the stomach. Enteric coated tablets are well known to those skilled in the art. In addition, capsules filled with small spheres each coated to protect from the acidic stomach, are also well known to those skilled in the art.

When administered orally, an administered amount therapeutically effective to inhibit amyloidogenic processing of APP, promote non-amyloidogenic processing of APP, or to treat or prevent AD is from about 0.1 mg/day to about 200 mg/day, for example, from about 1 mg/day to about 100 mg/day, for example, from about 5 mg/day to about 50 mg/day. In some embodiments, the subject is administered the compound at a dose of about 0.05 to about 0.50 mg/kg, for example, about 0.05 mg/kg, 0.10 mg/kg, 0.20 mg/kg, 0.33 mg/kg, 0.50 mg/kg. It is understood that while a patient may be started at one dose, that dose may be varied (increased or decreased, as appropriate) over time as the patient's condition changes. Depending on outcome evaluations, higher doses may be used. For example, in certain embodiments, up to as much as 1000 mg/day can be administered, e.g., 5 mg/day, 10 mg/day, 25 mg/day, 50 mg/day, 100 mg/day, 200 mg/day, 300 mg/day, 400 mg/day, 500 mg/day, 600 mg/day, 700 mg/day, 800 mg/day, 900 mg/day or 1000 mg/day.

The compounds and/or analogs thereof may also be advantageously delivered in a nano crystal dispersion formulation. Preparation of such formulations is described, for example, in U.S. Pat. No. 5,145,684. Nano crystalline dispersions of HIV protease inhibitors and their method of use are described in U.S. Pat. No. 6,045,829. The nano crystalline formulations typically afford greater bioavailability of drug compounds.

In various embodiments, the compounds and/or analogs thereof can be administered parenterally, for example, by IV, IM, depo-IM, SC, or depo-SC. When administered parenterally, a therapeutically effective amount of about 0.5 to about 100 mg/day, preferably from about 5 to about 50 mg daily should be delivered. When a depot formulation is used for injection once a month or once every two weeks, the dose should be about 0.5 mg/day to about 50 mg/day, or a monthly dose of from about 15 mg to about 1,500 mg. In part because of the forgetfulness of the patients with Alzheimer's disease, it is preferred that the parenteral dosage form be a depo formulation.

In various embodiments, the compounds and/or analogs thereof can be administered sublingually. When given sublingually, the compounds and/or analogs thereof can be given one to four times daily in the amounts described above for IM administration.

In various embodiments, the compounds and/or analogs thereof can be administered intranasally. When given by this route, the appropriate dosage forms are a nasal spray or dry powder, as is known to those skilled in the art. The dosage of compound and/or analog thereof for intranasal administration is the amount described above for IM administration.

In various embodiments, compound and/or analogs thereof can be administered intrathecally. When given by this route the appropriate dosage form can be a parenteral dosage form as is known to those skilled in the art. The dosage of compound and/or analog thereof for intrathecal administration is the amount described above for IM administration.

In certain embodiments, the compound and/or analog thereof can be administered topically. When given by this route, the appropriate dosage form is a cream, ointment, or patch. When administered topically, the dosage is from about 1.0 mg/day to about 200 mg/day. Because the amount that can be delivered by a patch is limited, two or more patches may be used. The number and size of the patch is not important, what is important is that a therapeutically effective amount of compound be delivered as is known to those skilled in the art. The compound can be administered rectally by suppository as is known to those skilled in the art. When administered by suppository, the therapeutically effective amount is from about 1.0 mg to about 500 mg.

In various embodiments, the compound and/or analog thereof can be administered by implants as is known to those skilled in the art. When administering the compound by implant, the therapeutically effective amount is the amount described above for depot administration.

It should be apparent to one skilled in the art that the exact dosage and frequency of administration will depend on the particular condition being treated, the severity of the condition being treated, the age, weight, general physical condition of the particular patient, and other medication the individual may be taking as is well known to administering physicians who are skilled in this art.

c. Passive Immunization

Therapeutic agents for use in passive immunization against gram-negative bacteria in the brain include antibodies and fragments thereof that specifically bind to an immunogenic antigen of gram-negative bacteria. Accordingly, provided are methods of mitigating, reversing or eliminating in a subject one or more symptoms associated with cognitive impairment associated with amyloid deposits in the brain, the method comprising delivering to the brain of the subject one or more antibodies or fragments thereof that specifically bind to an immunogenic antigen of gram-negative bacteria, in an amount sufficient to mitigate, reverse or eliminate the one or more symptoms of said cognitive impairment. Illustrative immunogenic antigens of gram-negative bacteria include without limitation Gram-negative lipopolysaccharide (LPS), LPS O antigen, K antigen, *E. coli* K99 pili protein, *E. coli* J5 LPS, an LPS/Aβ1-40/42 aggregate, an admixture comprising LPS and Aβ1-40/42 peptide or fragments thereof, Gram-negative GrpE, Gram-negative CAT (Chloramphenicol Acetyltransferase), Gram-negative TetR (Tet Repressor Protein), Gram-negative ALK (Alkaline Phosphatase), Gram-negative 13 gal (β-Galactosidase) and one or more *Porphyromonas gingivalis* gingipains (e.g., Arginine Gingipain A (RgpA) and/or Arginine Gingipain B (RgpB) and/or Lysine Gingipain (Kgp)). Antibodies against LPS and *Escherichia coli* O and K antigens are known in the art, and may find use. See, Kaijser, et al., *Infect Immun.* (1977) 17(2):286-289; Dziarski, *J Clin Lab Immunol.* (1985) 16(2):93-109; and Ohl, et al., *Prog Clin Biol Res.* (1998) 397:227-34. Antibodies useful as an immunotherapeutic agent against gingipains are described, e.g., in Yokoyama, et al., *Oral Microbiol Immunol.* (2007) 22(5):352-5.

Such antibodies can be monoclonal or polyclonal. Antibodies of use for passive immunization against gram negative bacteria in the brain include all known forms of antibodies and other protein scaffolds with antibody-like properties. For example, the antibody can be a human antibody, a humanized antibody, a bispecific antibody, a chimeric antibody or a protein scaffold with antibody-like properties, such as fibronectin or Ankyrin repeats. The antibody also can be a Fab, Fab'2, ScFv, SMIP, affibody, nanobody, or a domain antibody. In various embodiments the antibody also can have any of the following isotypes: IgG1, IgG2, IgG3, IgG4, IgM, IgA1, IgA2, IgAsec, IgD, and IgE. In varying embodiments, antibodies used in therapeutic methods can have an intact constant region or at least sufficient of the constant region to interact with an Fc receptor. Human isotype IgG1 is of use because it has the highest affinity of human isotypes for the FcRI receptor on phagocytic cells. Bispecific Fab fragments can also be used, in which one arm of the antibody has specificity for a gram negative bacteria antigen, and the other for an Fc receptor. Some antibodies bind to the gram negative bacteria antigen, optionally in a denatured form, such as when treated with SDS, with a binding affinity greater than or equal to about $10^6$, $10^7$, $10^8$, $10^9$, $10^{10}$, $10^{11}$, $10^{12}$ $M^{-1}$. Production of antibodies is well known in the art, and described, e.g., in Howard and Kaser, Making and Using Antibodies: A Practical Handbook, Second Edition, 2013, CRC Press; Harlow and Lane, Using Antibodies: A Laboratory Manual, 1998, Cold Spring Harbor Laboratory Press; Greenfield, Antibodies A Laboratory Manual, Second edition, 2013, Cold Spring Harbor Laboratory Press, and U.S. Pat. No. 9,034,337, incorporated herein by reference in its entirety for all purposes. Antibodies which may be useful for targeting of gram negative bacteria antigens in the brain are commercially available and described herein, e.g., Abbiotec (GFAP, 250661; MAG, 250744), Abcam (*E. coli* LPS, ab35654), Life Span (*E. coli* K99, LS-C83195), Millipore (Aβ31-40/42, AB5076; NeuN, ABN2300A4; NG2, AB5320), RayBiotech (*E. coli* LPS, MD-05-0148), Santa Cruz (β-actin, sc-69879), ThermoFisher (GSTπ, PA529601; Synapsin 2, OSS00020W) and from Wako (Iba1, 019-19741), Lifespan (CAT, LS-C153970; GrpE, LS-C66627; TetR, LS-C49339; 3 gal, LS-C63430) and Millipore (ALK, MAB1012).

For passive immunization with an antibody, the dosage ranges from about 0.0001 to 100 mg/kg, and more usually 0.01 to 5 mg/kg, of the host body weight. For example dosages can be 1 mg/kg body weight or 10 mg/kg body weight or within the range of 1-10 mg/kg or, in other words, 70 mgs or 700 mgs or within the range of 70-700 mgs, respectively, for a 70 kg patient. An exemplary treatment regime entails administration once per every two weeks or once a month or once every 3 to 6 months. In some methods, two or more monoclonal antibodies with different binding specificities are administered simultaneously, in which case the dosage of each antibody administered falls within the ranges indicated. Antibody is usually administered on multiple occasions. Intervals between single dosages can be weekly, monthly or yearly. Intervals can also be irregular as indicated by measuring blood levels of antibody to gram negative bacterial immunogenic antigens in the patient. In some methods, dosage is adjusted to achieve a plasma antibody concentration of 1-1000 μg/ml and in some methods 25-300 μg/ml. Alternatively, antibody can be administered as a sustained release formulation, in which case less frequent administration is required. Dosage and frequency vary depending on the half-life of the antibody in the patient. In general, human antibodies show the longest half-life, followed by humanized antibodies, chimeric antibodies, and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patent can be administered a prophylactic regime.

Antibodies and fragments thereof can be administered by parenteral, topical, intravenous, oral, subcutaneous, intraarterial, intracranial, intrathecal, intraperitoneal, intranasal or intramuscular means for prophylactic and/or therapeutic treatment. The most typical route of administration of an immunogenic agent is subcutaneous although other routes can be equally effective. The next most common route is intramuscular injection. This type of injection is most typically performed in the arm or leg muscles. In some methods, agents are injected directly into a particular tissue where deposits have accumulated, for example intracranial injection. In some methods, particular therapeutic antibodies are injected directly into the cranium. In some methods, antibodies are administered as a sustained release composition or device. In varying embodiments, the antibodies or fragments thereof are conjugated to or encapsulated within an agent that facilitates delivery across the blood-brain-barrier, as described above and herein.

For parenteral administration, agents of the invention can be administered as injectable dosages of a solution or suspension of the substance in a physiologically acceptable diluent with a pharmaceutical carrier that can be a sterile liquid such as water oils, saline, glycerol, or ethanol. Additionally, auxiliary substances, such as wetting or emulsifying agents, surfactants, pH buffering substances and the like can be present in compositions. Other components of pharmaceutical compositions are those of petroleum, animal, vegetable, or synthetic origin, for example, peanut oil, soybean oil, and mineral oil. In general, glycols such as propylene glycol or polyethylene glycol are preferred liquid carriers, particularly for injectable solutions. Antibodies can be administered in the form of a depot injection or implant preparation which can be formulated in such a manner as to permit a sustained release of the active ingredient. An exemplary composition comprises monoclonal antibody at 5 mg/mL, formulated in aqueous buffer consisting of 50 mM L-histidine, 150 mM NaCl, adjusted to pH 6.0 with HCl. Compositions for parenteral administration are typically substantially sterile, substantially isotonic and manufactured under GMP conditions of the FDA or similar body. For example, compositions containing biologics are typically sterilized by filter sterilization. Compositions can be formulated for single dose administration.

Typically, compositions are prepared as injectables, either as liquid solutions or suspensions; solid forms suitable for solution in, or suspension in, liquid vehicles prior to injection can also be prepared. The preparation also can be emulsified or encapsulated in liposomes or micro particles such as polylactide, polyglycolide, or copolymer for enhanced adjuvant effect, as discussed above (see Langer, Science 249, 1527 (1990) and Hanes, Advanced Drug Delivery Reviews 28, 97-119 (1997). The agents of this invention can be administered in the form of a depot injection or implant preparation which can be formulated in such a manner as to permit a sustained or pulsatile release of the active ingredient. Compositions can be formulated in unit dosage form (i.e., the formulation contains sufficient of the active ingredient for one dosage to one patient).

d. Active Immunization

In some embodiments, the methods of mitigating, reversing or eliminating in a subject one or more symptoms associated with cognitive impairment associated with amyloid deposits in the brain comprise administering to the subject one or more immunogenic antigens sufficient to induce or enhance an immune response in the subject against gram negative bacteria in the brain, thereby reducing or eliminating the presence of gram negative bacteria in the brain in the subject, and mitigating, reversing or eliminating the one or more symptoms of said cognitive impairment. In varying embodiments, the one or more immunogenic antigens are selected from the group consisting of selected from the group consisting of Gram-negative lipopolysaccharide (LPS), LPS O antigen, *E. coli* K99 pili protein, *E. coli* J5 LPS, an LPS/Aβ1-40/42 aggregate, an admixture comprising LPS and Aβ1-40/42 peptide or fragments thereof, Gram-negative GrpE, Gram-negative CAT (Chloramphenicol Acetyltransferase), Gram-negative TetR (Tet Repressor Protein), Gram-negative ALK (Alkaline Phosphatase), Gram-negative β gal (β-Galactosidase), one or more *Porphyromonas gingivalis* gingipains (e.g., Arginine Gingipain A (RgpA) and/or Arginine Gingipain B (RgpB) and/or Lysine Gingipain (Kgp)), and fragments thereof.

In varying embodiments, the gram negative bacteria immunogenic antigen is linked to a carrier to form a conjugate. Some agents for inducing an immune response contain the appropriate epitope for inducing an immune response but are too small to be immunogenic. In this situation, a peptide immunogen can be linked to a suitable carrier molecule to form a conjugate which helps elicit an immune response. Suitable carriers include serum albumins, keyhole limpet hemocyanin, immunoglobulin molecules, thyroglobulin, ovalbumin, tetanus toxoid, or a toxoid from other pathogenic bacteria, such as diphtheria, *E. coli*, cholera, or *H. pylori*, or an attenuated toxin derivative. T cell epitopes are also suitable carrier molecules. Some conjugates can be formed by linking agents of the invention to an immunostimulatory polymer molecule (e.g., tripalmitoyl-S-glycerine cysteine (Pam$_3$Cys), mannan (a manose polymer), or glucan (a beta 1→2 polymer)), cytokines (e.g., IL-1, IL-1 alpha and beta peptides, IL-2, gamma-INF, IL-10, GM-CSF), and chemokines (e.g., MIP1alpha and beta, and RANTES). Immunogenic agents can also be linked to peptides that enhance transport across tissues, as described in O'Mahony, WO 97/17613 and WO 97/17614. Immunogens may be linked to the carries with or without spacers amino acids (e.g., gly-gly).

Some conjugates can be formed by linking agents of the invention to at least one T cell epitope. Some T cell epitopes are promiscuous while other T cell epitopes are universal. Promiscuous T cell epitopes are capable of enhancing the induction of T cell immunity in a wide variety of subjects displaying various HLA types. In contrast to promiscuous T cell epitopes, universal T cell epitopes are capable of enhancing the induction of T cell immunity in a large percentage, e.g., at least 75%, of subjects displaying various HLA molecules encoded by different HLA-DR alleles.

A large number of naturally occurring T-cell epitopes exist, such as, tetanus toxoid (e.g., the P2 and P30 epitopes), Hepatitis B surface antigen, pertussis, toxoid, measles virus F protein, *Chlamydia trachomitis* major outer membrane protein, diphtheria toxoid, *Plasmodium falciparum* circumsporozite T, *Plasmodium falciparum* CS antigen, *Schistosoma mansoni* triose phosphate isomersae, *Escherichia coli* TraT, and Influenza virus hemagluttinin (HA). The immunogenic peptides of the invention can also be conjugated to the T-cell epitopes described in Sinigaglia F. et al., Nature, 336:778-780 (1988); Chicz R. M. et al., J. Exp. Med., 178:27-47 (1993); Hammer J. et al., Cell 74:197-203 (1993); Falk K. et al., Immunogenetics, 39:230-242 (1994); WO 98/23635; and, Southwood S. et al. J. Immunology, 160: 3363-3373 (1998) (each of which is incorporated herein by reference for all purposes).

Alternatively, the conjugates can be formed by linking agents of the invention to at least one artificial T-cell epitope capable of binding a large proportion of MHC Class II molecules, such as the pan DR epitope ("PADRE"). PADRE is described in U.S. Pat. No. 5,736,142, WO 95/07707, and Alexander J et al., Immunity, 1:751-761 (1994) (each of which is incorporated herein by reference for all purposes).

Immunogenic agents can be linked to carriers by chemical crosslinking. Techniques for linking an immunogen to a carrier include the formation of disulfide linkages using N-succinimidyl-3-(2-pyridyl-thio)propionate (SPDP) and succinimidyl 4-(N-maleimidomethyl)cyclohexane-1-carboxylate (SMCC) (if the peptide lacks a sulfhydryl group, this can be provided by addition of a cysteine residue). These reagents create a disulfide linkage between themselves and peptide cysteine resides on one protein and an amide linkage through the epsilon-amino on a lysine, or other free amino group in other amino acids. A variety of such disulfide/amide-forming agents are described by Immun. Rev. 62, 185 (1982). Other bifunctional coupling agents form a thioether rather than a disulfide linkage. Many of these thio-ether-forming agents are commercially available and include reactive esters of 6-maleimidocaproic acid, 2-bromoacetic acid, and 2-iodoacetic acid, 4-(N-maleimido-methyl)cyclohexane-1-carboxylic acid. The carboxyl groups can be activated by combining them with succinimide or 1-hydroxyl-2-nitro-4-sulfonic acid, sodium salt.

Immunogenicity can be improved through the addition of spacer residues (e.g., Gly-Gly) between the Th epitope and the peptide immunogen of the invention. In addition to physically separating the Th epitope from the B cell epitope (i.e., the peptide immunogen), the glycine residues can disrupt any artificial secondary structures created by the joining of the Th epitope with the peptide immunogen, and thereby eliminate interference between the T and/or B cell responses. The conformational separation between the helper epitope and the antibody eliciting domain thus permits more efficient interactions between the presented immunogen and the appropriate Th and B cells.

To enhance the induction of T cell immunity in a large percentage of subjects displaying various HLA types to an agent of the present invention, a mixture of conjugates with different Th cell epitopes can be prepared. The mixture may contain a mixture of at least two conjugates with different Th cell epitopes, a mixture of at least three conjugates with different Th cell epitopes, or a mixture of at least four conjugates with different T.sub.h cell epitopes. The mixture may be administered with an adjuvant.

Immunogenic peptides can also be expressed as fusion proteins with carriers (i.e., heterologous peptides). The immunogenic peptide can be linked at its amino terminus, its carboxyl terminus, or both to a carrier. Optionally, multiple repeats of the immunogenic peptide can be present in the fusion protein. Optionally, an immunogenic peptide can be linked to multiple copies of a heterologous peptide, for example, at both the N and C termini of the peptide. Some carrier peptides serve to induce a helper T-cell response against the carrier peptide. The induced helper T-cells in turn induce a B-cell response against the immunogenic peptide linked to the carrier peptide.

Some agents of the invention comprise a fusion protein in which an N-terminus of the gram negative bacteria immunogenic antigen is linked at its C-terminus to a carrier peptide. In such agents, the N-terminal residue of the gram negative bacteria immunogenic antigen constitutes the N-terminal residue of the fusion protein. Accordingly, such fusion proteins are effective in inducing antibodies that bind to an epitope that requires the N-terminal residue of the gram negative bacteria immunogenic antigen to be in free form. Some agents of the invention comprise a fusion protein in which a C-terminal fragment of the gram negative bacteria immunogenic antigen is linked at its N-terminus to a carrier peptide. In such agents, the C-terminal residue of the fragment of the gram negative bacteria immunogenic antigen constitutes the C-terminal residue of the fusion protein. Accordingly, such fusion proteins are effective in inducing antibodies that bind to an epitope that requires the C-terminal residue of the gram negative bacteria immunogenic antigen to be in free form.

Some examples of fusion proteins suitable for use in the invention are shown below. Some of these fusion proteins comprise segments of gram negative bacteria immunogenic antigens (including any of the fragments described above) linked to tetanus toxoid epitopes such as described in U.S. Pat. No. 5,196,512, EP 378,881 and EP 427,347. Some fusion proteins comprise segments of one or more gram negative bacteria immunogenic antigens linked to at least one PADRE. Some heterologous peptides are promiscuous T-cell epitopes, while other heterologous peptides are universal T-cell epitopes. In some methods, the agent for administration is simply a single fusion protein with an gram negative bacteria immunogenic antigen segment linked to a heterologous segment in linear configuration. The therapeutic agents of the invention may be represented using a formula. For example, in some methods, the agent is multimer of fusion proteins represented by the formula $2^x$, in which x is an integer from 1-5. Preferably x is 1, 2, or 3, with 2 being most preferred. When x is two, such a multimer has four fusion proteins linked in a preferred configuration referred to as MAP4 (see U.S. Pat. No. 5,229,490).

Gram negative bacteria immunogenic antigens are sometimes administered in combination with an adjuvant. A variety of adjuvants can be used in combination with a gram negative bacteria immunogenic antigens, to elicit an immune response. Preferred adjuvants augment the intrinsic response to an immunogen without causing conformational changes in the immunogen that affect the qualitative form of the response. Preferred adjuvants include aluminum hydroxide and aluminum phosphate, 3 De-O-acylated monophosphoryl lipid A (MPL™) (Enzo Life Sciences). QS-21 is a triterpene glycoside or saponin isolated from the bark of the Quillaja Saponaria Molina tree found in South America (see Kensil et al., in Vaccine Design: The Subunit and Adjuvant Approach (eds. Powell & Newman, Plenum Press, N Y, 1995); U.S. Pat. No. 5,057,540), (Aquila BioPharmaceuticals, Framingham, Mass.). Other adjuvants are oil in water emulsions (such as squalene or peanut oil), optionally in combination with immune stimulants, such as monophosphoryl lipid A (see Stoute et al., N. Engl. J. Med. 336, 86-91 (1997)), pluronic polymers, and killed mycobacteria. Another adjuvant is CpG (WO 98/40100). Alternatively, Gram negative bacteria immunogenic antigens can be coupled to an adjuvant. However, such coupling should not substantially change the conformation of the gram negative bacteria immunogenic antigen so as to affect the nature of the immune response thereto. Adjuvants can be administered as a component of a therapeutic composition with an active agent or can be administered separately, before, concurrently with, or after administration of the therapeutic agent.

One class of adjuvants is aluminum salts (alum), such as alum hydroxide, alum phosphate, alum sulfate. Such adjuvants can be used with or without other specific immunostimulating agents such as MPL or 3-DMP, QS-21, polymeric or monomeric amino acids such as polyglutamic acid or polylysine. Another class of adjuvants is oil-in-water emulsion formulations. Such adjuvants can be used with or without other specific immunostimulating agents such as muramyl peptides (e.g., N-acetylmuramyl-L-threonyl-D-isoglutamine (thr-MDP), N-acetyl-normuramyl-L-alanyl-D-isoglutamine (nor-MDP), N-acetylmuramyl-L-alanyl-D-isoglutaminyl-L-alanine-2-(1'-2'dipalmitoyl-sn-glycero-3-hydroxyphosphoryloxy)-ethylamine (MTP-PE), N-acetylglucsaminyl-N-acetylmuramyl-L-Al-D-isoglu-L-Ala-dipalmitoxy propylamide (DTP-DPP) Theramide™), or other bacterial cell wall components. Oil-in-water emulsions include (a) MF59 (WO 90/14837), containing 5% Squalene, 0.5% Tween 80, and 0.5% Span 85 (optionally containing various amounts of MTP-PE) formulated into submicron particles using a microfluidizer such as Model 110Y microfluidizer (Microfluidics, Newton Mass.), (b) SAF, containing 10% Squalene, 0.4% Tween 80, 5% pluronic-blocked polymer L121, and thr-MDP, either microfluidized into a submicron emulsion or vortexed to generate a larger particle size emulsion, and (c) Ribi™ adjuvant system (RAS), containing 2% squalene, 0.2% Tween 80, and one or more bacterial cell wall components from the group consisting of monophosphoryllipid A (MPL), trehalose dimycolate (TDM), and cell wall skeleton (CWS), preferably MPL+CWS (Detox™).

Another class of adjuvants is saponin adjuvants, such as QS-21 or particles generated therefrom such as ISCOMs (immunostimulating complexes) and ISCOMATRIX. Other adjuvants include RC-529, GM-CSF and Complete Freund's Adjuvant (CFA) and Incomplete Freund's Adjuvant (IFA). Other adjuvants include cytokines, such as interleukins (e.g., IL-1, IL-2, IL-4, IL-6, IL-12, IL-13, and IL-15), macrophage colony stimulating factor (M-CSF), granulocyte-macrophage colony stimulating factor (GM-CSF), and tumor necrosis factor (TNF). Another class of adjuvants is glycolipid analogues including N-glycosylamides, N-glycosylureas and N-glycosylcarbamates, each of which is substituted in the sugar residue by an amino acid, as immunomodulators or adjuvants (see U.S. Pat. No. 4,855,283). Heat shock proteins, e.g., HSP70 and HSP90, may also be used as adjuvants.

An adjuvant can be administered with an immunogen as a single composition, or can be administered before, concurrent with or after administration of the immunogen. Immunogen and adjuvant can be packaged and supplied in the same vial or can be packaged in separate vials and mixed before use. Immunogen and adjuvant are typically packaged with a label indicating the intended therapeutic application.

If immunogen and adjuvant are packaged separately, the packaging typically includes instructions for mixing before use. The choice of an adjuvant and/or carrier depends on the stability of the immunogenic formulation containing the adjuvant, the route of administration, the dosing schedule, the efficacy of the adjuvant for the species being vaccinated, and, in humans, a pharmaceutically acceptable adjuvant is one that has been approved or is approvable for human administration by pertinent regulatory bodies. For example, Complete Freund's adjuvant is not suitable for human administration. Alum, MPL and QS-21 find use. Optionally, two or more different adjuvants can be used simultaneously. Preferred combinations include alum with MPL, alum with QS-21, MPL with QS-21, MPL or RC-529 with GM-CSF, and alum, QS-21 and MPL together. Also, Incomplete Freund's adjuvant can be used (Chang et al., Advanced Drug Delivery Reviews 32, 173-186 (1998)), optionally in combination with any of alum, QS-21, and MPL and all combinations thereof.

Effective doses of gram negative bacteria immunogenic antigens sufficient to induce an immunogenic response against gram negative bacteria in the brain may vary depending upon many different factors, including means of administration, target site, physiological state of the patient, whether the patient is human or an animal, other medications administered, and whether treatment is prophylactic or therapeutic. Usually, the patient is a human but nonhuman mammals including transgenic mammals can also be treated. Treatment dosages need to be titrated to optimize safety and efficacy. The amount of immunogen depends on whether adjuvant is also administered, with higher dosages being required in the absence of adjuvant. The amount of an immunogen for administration sometimes varies from 1-500 µg per patient and more usually from 5-500 µg per injection for human administration. Occasionally, a higher dose of 1-2 mg per injection is used. Typically about 10, 20, 50 or 100 µg is used for each human injection. The mass of immunogen also depends on the mass ratio of immunogenic epitope within the immunogen to the mass of immunogen as a whole. Typically, $10^{-3}$ to $10^{-5}$ micromoles of immunogenic epitope are used for microgram of immunogen. The timing of injections can vary significantly from once a day, to once a year, to once a decade. On any given day that a dosage of immunogen is given, the dosage is greater than 1 µg/patient and usually greater than 10 µg/patient if adjuvant is also administered, and greater than 10 µg/patient and usually greater than 100 µg/patient in the absence of adjuvant. A typical regimen consists of an immunization followed by booster injections at time intervals, such as 6 week intervals. Another regimen consists of an immunization followed by booster injections 1, 2 and 12 months later. Another regimen entails an injection every two months for life. Alternatively, booster injections can be on an irregular basis as indicated by monitoring of immune response.

Doses for nucleic acids encoding immunogens range from about 10 ng to 1 g, 100 ng to 100 mg, 1 µg to 10 mg, or 30-300 µg DNA per patient. Doses for infectious viral vectors vary from 10-100, or more, virions per dose.

Agents for inducing an immune response can be administered by parenteral, topical, intravenous, oral, subcutaneous, intraarterial, intracranial, intrathecal, intraperitoneal, intranasal or intramuscular means for prophylactic and/or therapeutic treatment. The most typical route of administration of an immunogenic agent is intradermal or subcutaneous although other routes can be equally effective. The next most common route is intramuscular injection.

e. Combination Therapies

In certain embodiments, the present treatment methods (e.g., delivery to the brain of antibiotics against gram-negative bacteria and/or TLR4 inhibitors/antagonists; passive and/or active immunization against gram negative bacteria) can be used in combination with other therapeutic agents or approaches used to treat or prevent diseases characterized by amyloid deposits in the brain, including MCI and/or AD. Such agents or approaches include: acetylcholinesterase inhibitors (including without limitation, e.g., (−)-phenserine enantiomer, tacrine, ipidacrine, galantamine, donepezil, icopezil, zanapezil, rivastigmine, huperzine A, phenserine, physostigmine, neostigmine, pyridostigmine, ambenonium, demarcarium, edrophonium, ladostigil and ungeremine); NMDA receptor antagonist (including without limitations e.g., Memantine); muscarinic receptor agonists (including without limitation, e.g., Talsaclidine, AF-102B, AF-267B (NGX-267)); nicotinic receptor agonists (including without limitation, e.g., Ispronicline (AZD-3480)); beta-secretase inhibitors (including without limitations e.g., thiazolidinediones, including rosiglitazone and pioglitazone); gamma-secretase inhibitors (including without limitation, e.g., MK-0752, E-2012, BMS-708163, PF-3084014, begacestat (GSI-953), and NIC5-15); agents which inhibit activity of *Porphyromonas gingivalis* gingipains (e.g., Olsen, et al., *J Oral Microbiol*. (2014) Aug. 18; 6 (PMID 25206939); US 2017/0014468), inhibitors of Aβ aggregation (including without limitation, e.g., Clioquinol (PBT1), PBT2, tramiprosate (homotaurine), Scyllo-inositol (a.k.a., scyllo-cyclohexanehexol, AZD-103 and ELND-005), passive immunotherapy with Aβ fragments (including without limitations e.g., Bapineuzemab) and Epigallocatechin-3-gallate (EGCg)); anti-inflammatory agents such as cyclooxygenase II inhibitors; anti-oxidants such as Vitamin E and ginkolides; immunological approaches, such as, for example, immunization with Aβ peptide or administration of anti-Aβ peptide antibodies; statins; and direct or indirect neurotrophic agents such as Cerebrolysin™, AIT-082 (Emilieu, 2000, *Arch. Neurol*. 57:454), Netrin (Luorenco, 2009, *Cell Death Differ* 16, 655-663), Netrin mimetics, NGF, NGF mimetics, BDNF and other neurotrophic agents, agents that promote neurogenesis e.g. stem cell therapy and/or gene therapy. Further pharmacologic agents useful in combination with the present treatment methods (e.g., delivery to the brain of antibiotics against gram-negative bacteria and/or TLR4 inhibitors/antagonists; passive and/or active immunization against gram negative bacteria) to treat or prevent diseases characterized by amyloid deposits in the brain, including MCI and/or AD, are described, e.g., in Mangialasche, et al., *Lancet Neurol* (2010) 9:702-16; Liu, et al., *Drugs Aging*. (2016) 33(10):685-697; Bhatti, et al., *J Clin Diagn Res*. (2016) 10(8):OE07-11; and Cummings, et al., *Alzheimers Res Ther*. (2016) 8:39).

5. Methods of Monitoring Clinical Efficacy

In various embodiments, the effectiveness of treatment can be determined by comparing a baseline measure of a parameter of disease before administration of the one or more active agents (e.g., one or more of antibiotics useful to treat gram-negative bacteria and/or TLR4 inhibitors and/or antibodies or fragments thereof against a gram-negative bacterial antigen and/or a gram-negative bacteria immunogenic antigen) and/or analogs thereof is commenced to the same parameter one or more timepoints after the compound or analog has been administered. One illustrative parameter that can be measured is a biomarker (e.g., a peptide oligomer) of APP processing. Such biomarkers include, but are not limited to increased levels of sAPPα, p3 (Aβ17-42 or Aβ17-40), sAPPβ, soluble Aβ40, and/or soluble Aβ42 in the blood, plasma, serum, urine, mucous or cerebrospinal fluid (CSF). Detection of increased levels of sAPPα and/or p3, and decreased levels of sAPPβ and/or APPneo is an indicator that the treatment is effective. Conversely, detection of decreased levels of sAPPα and/or p3, and/or increased levels of sAPPβ, APPneo, Tau or phospho-Tau (pTau) is an indicator that the treatment is not effective.

Another parameter to determine effectiveness of treatment is the level of amyloid plaque deposits in the brain. Amyloid plaques can be determined using any method known in the art, e.g., as determined by CT, PET, PIB-PET and/or MRI. Administration of the one or more active agents (e.g., one or more of antibiotics useful to treat gram-negative bacteria and/or TLR4 inhibitors and/or antibodies or fragments thereof against a gram-negative bacterial antigen and/or a gram-negative bacteria immunogenic antigen) can result in a reduction in the rate of plaque formation, and even a retraction or reduction of plaque deposits in the brain. Effectiveness of treatment can also be determined by observing a stabilization and/or improvement of cognitive abilities of the subject. Cognitive abilities can be evaluated using any art-accepted method, including for example, Clinical Dementia Rating (CDR), the mini-mental state examination (MMSE) or Folstein test, evaluative criteria listed in the DSM-IV (Diagnostic and Statistical Manual of Mental Disorders, Fourth Edition) or DSM-V, and the like.

Clinical efficacy can be monitored using any method known in the art. Measurable biomarkers to monitor efficacy include, but are not limited to, monitoring blood, plasma, serum, urine, mucous or cerebrospinal fluid (CSF) levels of sAPPα, sAPPβ, Aβ42, Aβ40, APPneo and p3 (e.g., Aβ17-42 or Aβ17-40). Detection of increased levels of sAPPα and/or p3, and decreased levels of sAPPβ and/or APPneo are indicators that the treatment or prevention regime is efficacious. Conversely, detection of decreased levels of sAPPα and/or p3, and increased levels of sAPPβ and/or APPneo are indicators that the treatment or prevention regime is not efficacious. Other biomarkers include Tau and phospho-Tau (pTau). Detection of decreased levels of Tau and pTau are indicators that the treatment or prevention regime is efficacious.

Efficacy can also be determined by measuring amyloid plaque load in the brain. The treatment or prevention regime is considered efficacious when the amyloid plaque load in the brain does not increase or is reduced. Conversely, the treatment or prevention regime is considered inefficacious when the amyloid plaque load in the brain increases. Amyloid plaque load can be determined using any method known in the art, e.g., including CT, PET, PIB-PET and/or MRI.

Efficacy can also be determined by measuring the cognitive abilities of the subject. Cognitive abilities can be measured using any method known in the art. Illustrative tests include assigning a Clinical Dementia Rating (CDR) score or applying the mini mental state examination (MMSE) (Folstein, et al., *Journal of Psychiatric Research* 12 (3): 189-98). Subjects who maintain the same score or who achieve an improved score, e.g., when applying the CDR or MMSE, indicate that the treatment or prevention regime is efficacious. Conversely, subjects who receive a score indicating diminished cognitive abilities, e.g., when applying the CDR or MMSE, indicate that the treatment or prevention regime has not been efficacious.

In certain embodiments, the monitoring methods can entail determining a baseline value of a measurable biomarker or parameter (e.g., amyloid plaque load or cognitive abilities) in a subject before administering a dosage of the compound, and comparing this with a value for the same measurable biomarker or parameter after treatment.

In other methods, a control value (e.g., a mean and standard deviation) of the measurable biomarker or parameter is determined for a control population. In certain embodiments, the individuals in the control population have not received prior treatment and do not have AD, MCI, nor are at risk of developing AD or MCI. In such cases, if the value of the measurable biomarker or clinical parameter approaches the control value, then treatment is considered efficacious. In other embodiments, the individuals in the control population have not received prior treatment and have been diagnosed with AD or MCI. In such cases, if the value of the measurable biomarker or clinical parameter approaches the control value, then treatment is considered inefficacious.

In other methods, a subject who is not presently receiving treatment but has undergone a previous course of treatment is monitored for one or more of the biomarkers or clinical parameters to determine whether a resumption of treatment is required. The measured value of one or more of the biomarkers or clinical parameters in the subject can be compared with a value previously achieved in the subject after a previous course of treatment. Alternatively, the value measured in the subject can be compared with a control value (mean plus standard deviation/ANOVA) determined in population of subjects after undergoing a course of treatment. Alternatively, the measured value in the subject can be compared with a control value in populations of prophylactically treated subjects who remain free of symptoms of disease, or populations of therapeutically treated subjects who show amelioration of disease characteristics. In such cases, if the value of the measurable biomarker or clinical parameter approaches the control value, then treatment is considered efficacious and need not be resumed. In all of these cases, a significant difference relative to the control level (e.g., more than a standard deviation) is an indicator that treatment should be resumed in the subject.

The tissue sample for analysis is typically blood, plasma, serum, urine, mucous or cerebrospinal fluid from the subject.

6. Methods of Diagnosis

Provided are methods of determining whether gram-negative bacteria molecules are associated with amyloid plaques in a subject exhibiting one or more symptoms associated with cognitive impairment associated with amyloid deposits in the brain. In some embodiments, the methods comprise determining in a central nervous system (CNS) sample from the subject for the presence of gram negative bacteria; and positively identifying the presence of gram negative bacteria in the CNS sample as indicative of gram-negative bacteria molecules associated with amyloid plaques in the subject. In some embodiments, the central nervous system (CNS) sample is a cerebral spinal fluid (CSF) sample. In some embodiments, the central nervous system (CNS) sample is a brain tissue sample (e.g., superior temporal gyrus gray matter (GM) and/or frontal lobe white matter (WM)). In some embodiments, the presence of one or more gram negative bacteria biomarkers selected from the group consisting of Gram-negative lipopolysaccharide (LPS), LPS O antigen, K antigen, *E. coli* K99 pili protein, *E. coli* J5 LPS, an LPS/Aβ1-40/42 aggregate, an admixture comprising LPS and Aβ1-40/42 peptide or fragments thereof, Gram-negative GrpE, Gram-negative CAT (Chloramphenicol Acetyltransferase), Gram-negative TetR (Tet Repressor Protein), Gram-negative ALK (Alkaline Phosphatase), Gram-negative β gal (β-Galactosidase), one or more *Porphyromonas gingivalis* gingipains (e.g., Arginine Gingipain A (RgpA) and/or Arginine Gingipain B (RgpB) and/or Lysine Gingipain (Kgp)) is determined. In some embodiments, the gram negative bacterium is *E. coli*. Detection of the gram negative bacteria biomarkers can be achieved at the protein level, carbohydrate level or polynucleotide level. Antibodies useful for the detection of gram negative bacteria antigens are commercially available and described herein, e.g., Abbiotec (GFAP, 250661; MAG, 250744), Abcam (*E. coli* LPS, ab35654), Life Span (*E. coli* K99, LS-C83195), Millipore (Aβ1-40/42, AB5076; NeuN, ABN2300A4; NG2, AB5320), RayBiotech (*E. coli* LPS, MD-05-0148), Santa Cruz (β-actin, sc-69879), ThermoFisher (GSTπ, PA529601; Synapsin 2, OSS00020W) and from Wako (Iba1, 019-19741), Lifespan (CAT, LS-C153970; GrpE, LS-C66627; TetR, LS-C49339; 3 gal, LS-C63430) and Millipore (ALK, MAB1012). Antibodies against *Porphyromonas gingivalis* gingipain R1 are also commercially available, e.g., from EpiGentek.com, biorbyt-.com and mybiosource.com.

EXAMPLES

The following examples are offered to illustrate, but not to limit the claimed invention.

Example 1

Gram-Negative Bacterial Molecules Associate with Alzheimer's Disease Pathology

Methods

Standard Protocol Approvals, Registrations, and Patient Consents.

The Institutional Review Board approved this study. Informed consent was obtained from all participants who were enrolled in studies at the University of California at Davis Alzheimer's Disease Center.

Brain Samples.

AD was rated using CERAD criteria and Braak stage on 24 AD and 18 age-matched controls. Brain tissue was provided by the Alzheimer's disease Center at the University of California Davis. Superior temporal gyms gray matter (GM) was studied since it is commonly involved in AD; and frontal lobe white matter (WM) was studied because it shows abnormalities in AD brains (17). Controls were age-matched individuals without cognitive deficits. Formalin-fixed brains used for immunostaining included 11 AD and 7 age-matched controls. Frozen brains used for Western blot analysis and PCR for *E. coli* DNA included 13 AD and 11 age-matched controls.

Frozen tissue (~1 cm3) from the superior temporal gyms GM or frontal lobe WM was removed with sterile technique and frozen at −70° C. The tissue surface was treated with 75% ethanol and removed with a sterile scalpel blade. Frozen tissue was cored with autoclaved trephines and placed in sterile, endotoxin-free tubes at −70° C. Formalin-fixed (4%) brains were blocked, embedded in paraffin and sectioned for immunostaining.

Immunofluorescence.

Detailed methods are described in our previous studies (15, 17, 18). Briefly, after removing paraffin with xylene and rehydrating through graded alcohols, sections were treated with antigen retrieval buffer and Autofluorescence Eliminator Reagent (Millipore). Primary antibodies were used in 1:200 concentrations unless stated otherwise. Secondary antibodies included either goat anti-mouse or goat anti-rabbit Alexa Fluor® 488 or 594 (Invitrogen). Slide mounting medium included DAPI to stain nuclei (Vector Labs). For controls, primary antibody was deleted or immuno-depleted with the target antigen of the antibody.

Western Blot Analysis.

Tissue was homogenized in cold RIPA buffer containing a protease inhibitor mixture. After centrifuging homogenates for 30 min at 4° C. (14,000 g), the pellet was discarded and proteins in the supernatant separated on 10% SDS polyacrylamide gels. They were then transferred to nitrocellulose membranes and hybridized overnight at 4° C. with primary antibodies listed below. Antibodies were stained using horseradish peroxidase-conjugated anti-rabbit or anti-mouse IgG (Bio-Rad) combined with ECL chemiluminescent detection (PIERS). β-actin staining served as the control. We used NIH Image J software to quantify band intensities.

Primary antibodies were obtained from Abbiotec (GFAP, 250661; MAG, 250744), Abcam (*E. coli* LPS, ab35654), Life Span (*E. coli* K99, LS-C83195), Millipore (Aβ31-40/42, AB5076; NeuN, ABN2300A4; NG2, AB5320), RayBiotech (*E. coli* LPS, MD-05-0148), Santa Cruz (β-actin, sc-69879), ThermoFisher (GSTπ, PA529601; Synapsin 2, OSS00020W) and from Wako (Iba1, 019-19741).

Polymerase Chain Reaction for DNA and DNA Sequencing.

*E. coli* DNA was detected using Polymerase Chain Reaction (PCR) amplification of an *E. coli* glutamate decarboxylase B (gadB) DNA fragment (19). This DNA fragment was selected because it detects all *E. coli* strains, and does not detect the human gene (19). All reagents used for PCR were first tested for *E. coli* DNA contamination which was indicated by detection of *E. coli* DNA in endotoxin free water. Only those reagents which were free of *E. coli* DNA were used for PCR amplification in human brains. Brain genomic DNA samples were isolated and purified using PureLink® Genomic DNA Kits (K1820-01, Life Technologies). About 20 mg of minced brain tissue from superior temporal gyms was digested and DNA was eluted and frozen. *E. coli* DNA from the ATCC 8739 strain (ATCC) was used as a positive control. PCR amplification was performed in a 50 μl reaction mixture, containing 10 ng of DNA, 25 μl of 2× GoTaq® Colorless Master Mix (Promega) and 0.5 M primer mix. The reaction mixtures were placed in a Gene Amp PCR System 9700 (Applied Biosystems) with the following settings: 5 min at 94° C., followed by 38 cycles of 40 sec at 94° C., 45 sec at 57° C., 30 sec at 72° C., and a final extension time of 7 min at 72° C. Amplified products were analyzed in an Agilent 2100 Bioanalyzer. Identification of the gadB gene was confirmed by a 3' and 5' Sanger DNA sequencing assay on 3 control and 3 AD samples at the UC Davis DNA Sequencing Facility. PCR products were sequenced with BigDye® Terminator v. 3.1 Cycle Sequencing Kit with Gel Company Better Buffer and post-cycle sequencing purification was achieved at a Beckman Coulter Biomek NXp Laboratory Automation Workstation with Beckman-Coulter CleanSEQ Magnetic Bead Purification. Data was analyzed with ABI Prism® 3730 Genetic Analyzer, ABI Prism® 3730 Data Collection Software v. 3.0, and ABI Prism® DNA Sequencing Analysis Software v. 5.2. DNA primers used in this study for PCR amplification and DNA sequencing were forward sequence (5'→3') CACGTTTTGGTGCG¬AAGTCT and reverse sequence (5'→3') TTGTGGACATTTTC¬GTCGTC (Eurofins MWG). Amplicons were 175 bps with Amplicon Accession number as M84025.1 (19).

Statistical Analysis.

Differences between groups were analyzed using a Student t-test (continuous), Wilcoxon-Mann Whitney test (ordinal) or Fisher Exact test (categorical). Differences between multiple groups were analyzed using one-way ANOVA with Student-Newman-Keuls post-hoc test. A $p<0.05$ was considered significant.

Results

Patient Characteristics.

There were no significant differences in age and sex between AD and controls (Table 4). The differences in median Braak and Braak stage (20) and CERAD plaque scores between AD and control brains were significant (Table 4).

TABLE 4

Demographic data and neuropathologic assessment of Alzheimer's disease patients and controls

|  | Controls (n = 18) | Alzheimer's disease (n = 24) |
| --- | --- | --- |
| Age (years ± SE ) | 80.9 ± 1.1 | 76.9 ± 1.9 |
| Gender Male: n (%) | 10 (55.6) | 9 (37.5) |
| PMI (hour ± SE) | 19.7 ± 5.6 | 15.7 ± 5.6 |
| Braak stage: Median | 2 | 6*** |
| CERAD score: |  |  |
| C0: n (%) | 10 (55.6) | 0 (0)*** |
| C1: n (%) | 8 (44.4) | 0 (0)*** |
| C2: n (%) | 0 (0) | 2 (8.3) |
| C3: n (%) | 0 (0) | 22 (91.7)*** |

Differences between groups were analyzed suing a Student t-test (continuous), Wilcoxon-Mann Whitney test (ordinal) or Fisher Exact test (categorical).
***$p < 0.001$ vs controls.
PMI: post mortem interval.

Detection of *E. coli* K99 and Gram-Negative Bacterial LPS in AD and Control Brains.

Figure 1B:
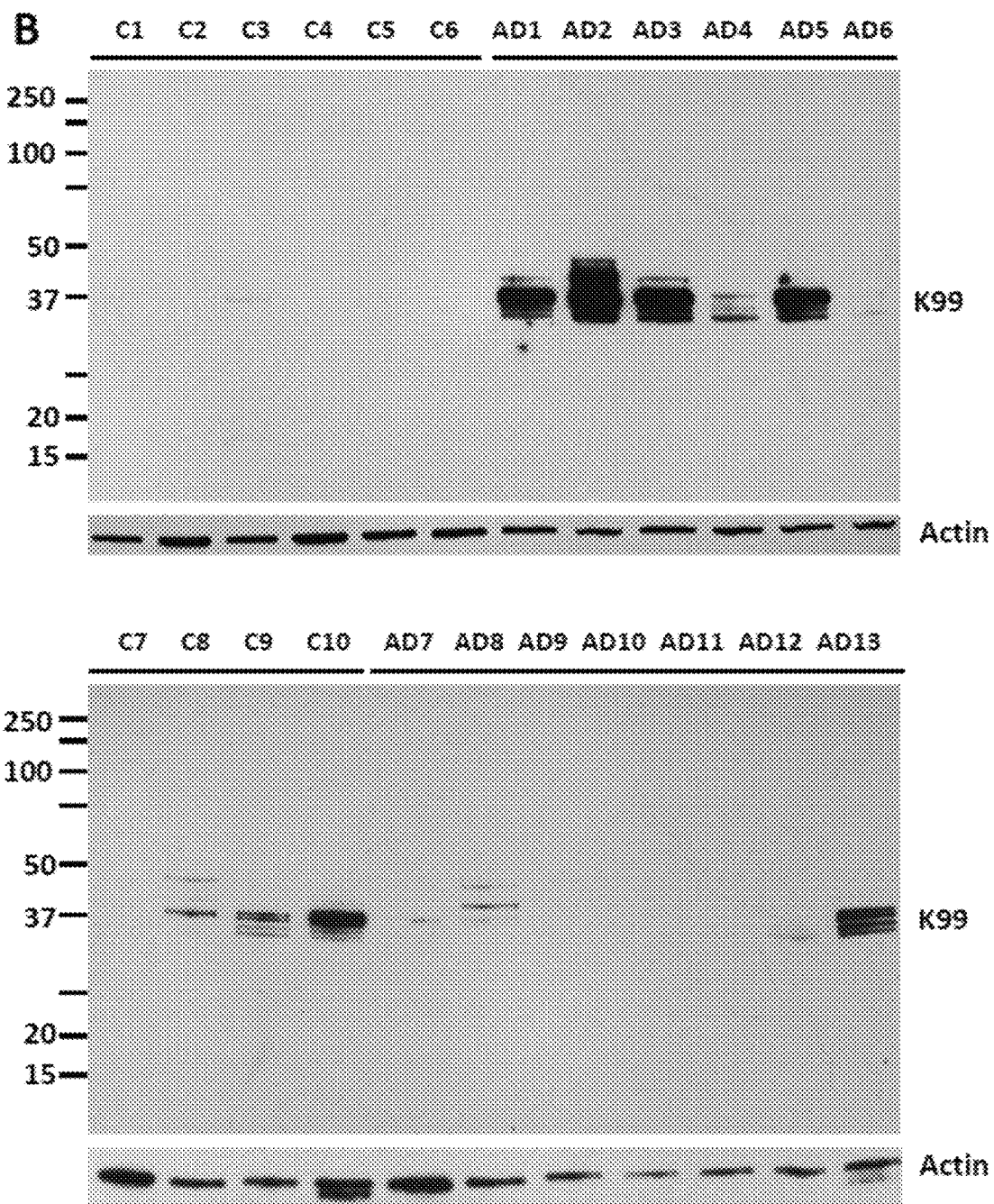
Figure 1C:
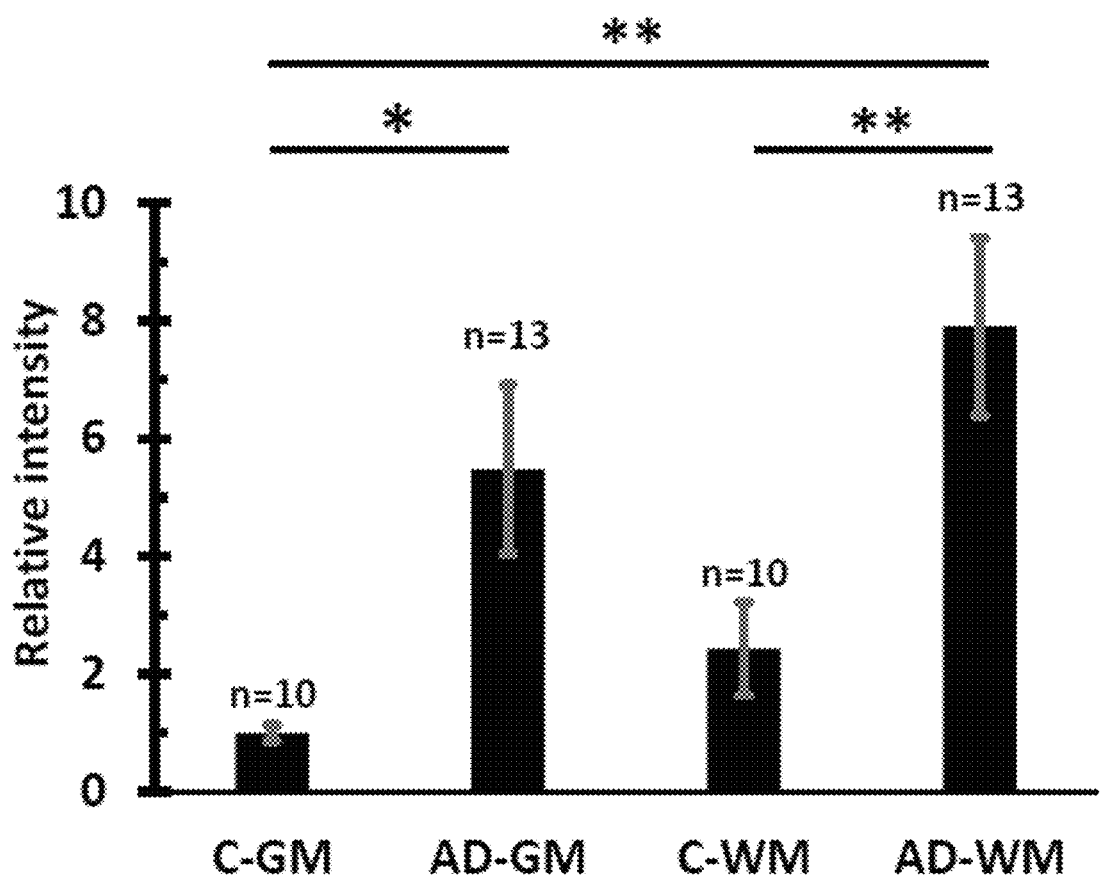

Control samples (n=10) and AD samples (n=13) including gray matter (GM) (FIG. 1A) and white matter (WM) (FIG. 1B) were assessed for *E. coli* K99 pili protein (21). K99 was present in 9/13 AD GM compared to 1/10 control GM samples (p=0.006) and in 10/13 AD WM compared to 4/10 control WM samples (p=0.09). Quantification showed significantly greater amounts of *E. coli* K99 protein in AD GM compared to controls and significantly more K99 in AD WM compared to controls (FIG. 1C).

Figure 1D:
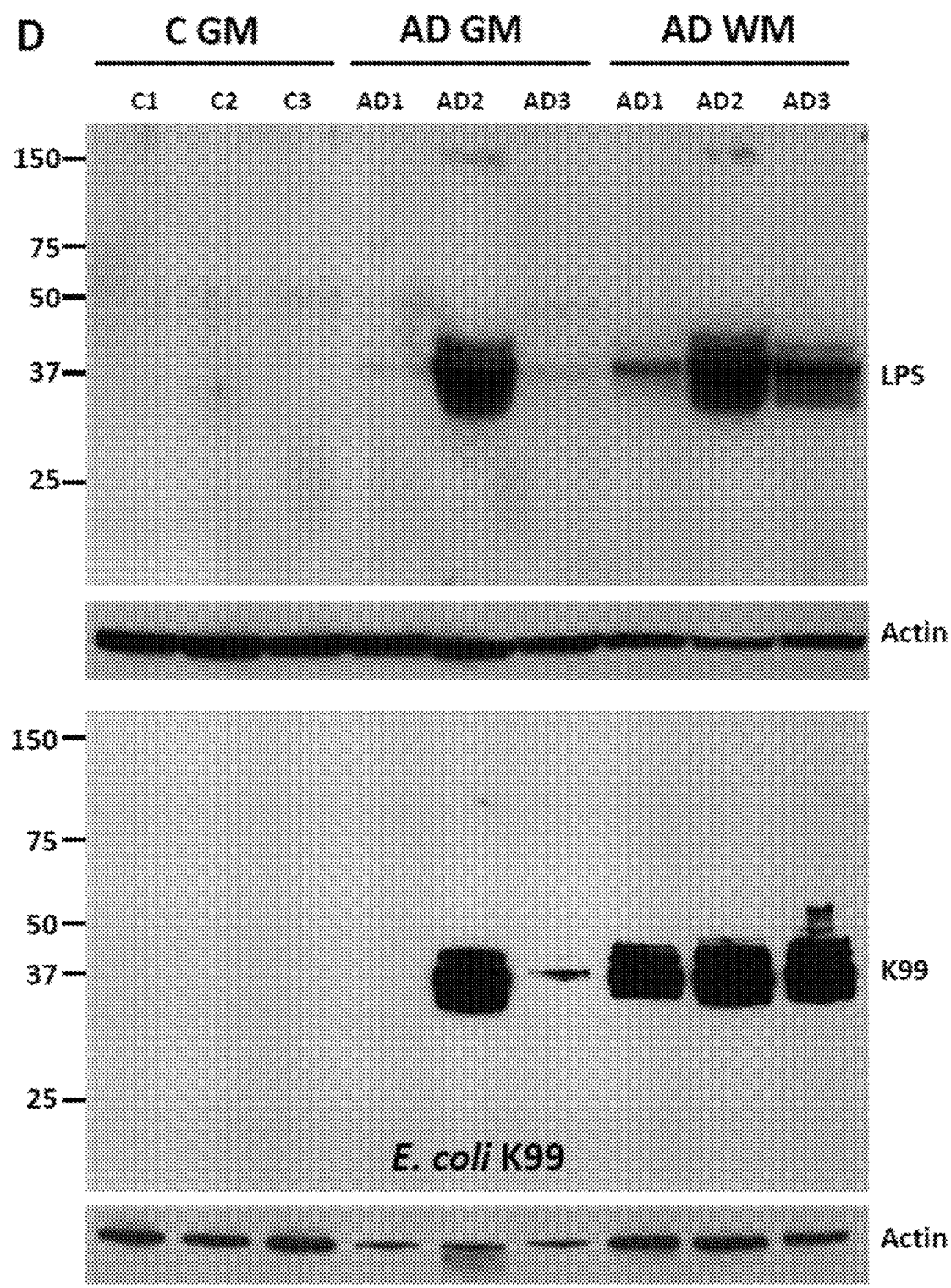
Figure 2:
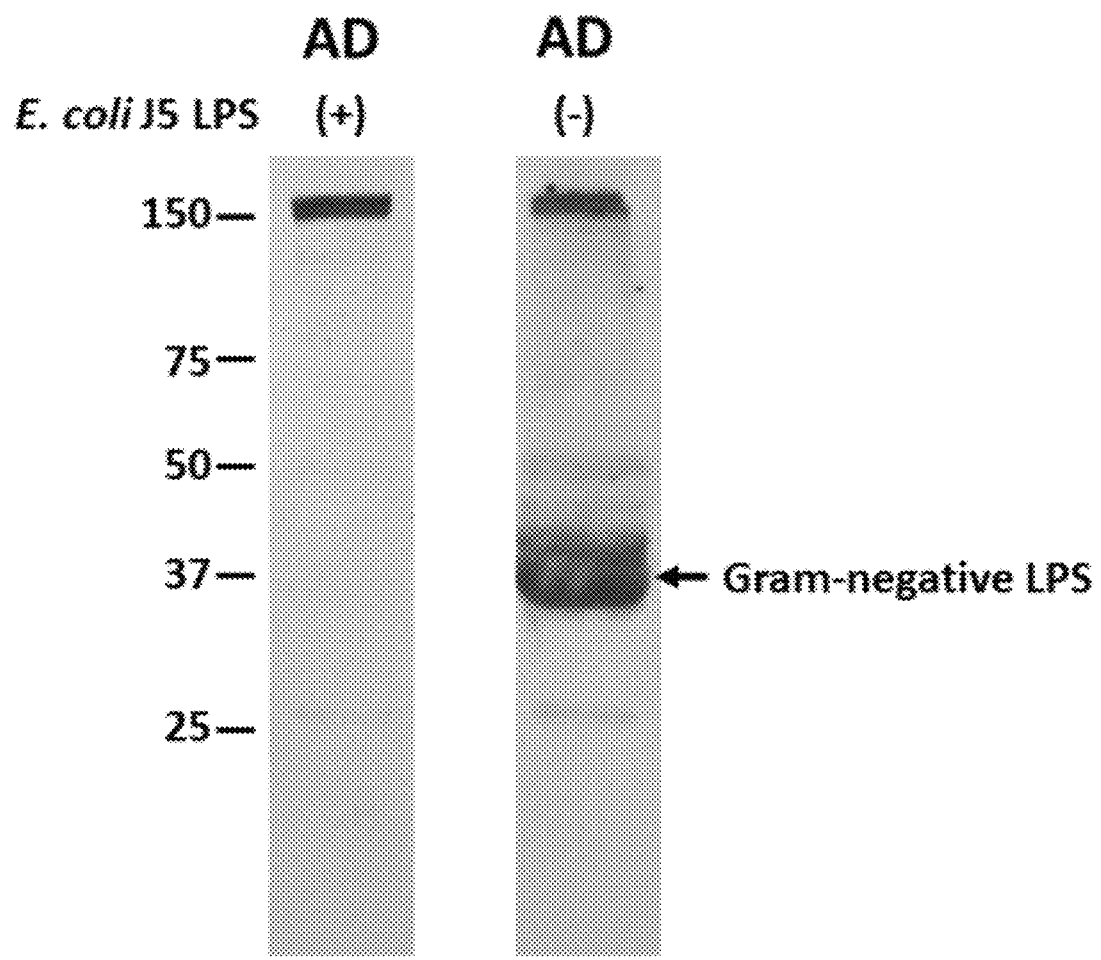
FIG. 2 illustrates immunoabsorption specificity controls in AD brain. Western blot of AD brain using antibody against Gram-negative LPS (RayBiotech, MD-05-0148) as well as a blot after immunoprecipitating the antibody with *E. coli* LPS (VWR, 102946-492, antibody:LPS=1:1 0). This anti-Gram-negative LPS antibody detected a large band at 37 kD (arrow, right panel) and a smaller band at 150 kD, whereas *E. coli* LPS immune-depleted antibody showed the 150 kD band only with complete loss of the 37 kD band (left panel). This is strong evidence the antibody detects LPS in the 37 kD band, and this is the same molecular weight as 37 kD large band seen in FIG. 1D with the Abcam anti-LPS antibody (lower panel). AD=Alzheimer's disease.

In addition, we used Western blots to test the specificity of Gram-negative LPS antibody which is used for the immunocytochemistry studies described below. The LPS Western blots using the Abcam antibody (FIG. 1D, upper panel) showed a similar pattern of expression as that seen for the K99 Western blots (FIG. 1D, lower panel). LPS (Abcam antibody) was detected by Western blots in 3/3 AD GM, 3/3 AD WM and 0/3 control GM (FIG. 1D). As a control, we repeated the Western blots of AD brain using another antibody to LPS (RayBiotech) as well as doing a blot after immunoprecipitating the antibody with LPS. The RayBiotech anti-LPS antibody detected a large band at 37 kD and a smaller band at 150 kD (FIG. 2), whereas the LPS immuno-depleted antibody showed the 150 kD band only with complete loss of the 37 kD band (FIG. 2). This is strong evidence the antibody detects LPS in the 37 kD band, and this is the same molecular weight as 37 kD large band seen in FIG. 1D with the Abcam anti-LPS antibody (upper panel).

Localization of LPS and K99 Pili Protein in Cells in AD and Control Brains.

*E. coli* LPS (Abcam antibody) and K99 pili protein were detected immunocytochemically in all 11 AD and 7 control brains. LPS was detected in control (FIG. 3A, 3C) and AD brains (FIG. 3B, 3D) in GM (FIG. 3A, 3B) and in periventricular WM (PVWM, FIG. 3C, 3D). For a control, co-immunoprecipitation of the anti-LPS antibody with LPS completely eliminated all tissue staining by immunofluorescence (FIG. 4) or by immunohistochemistry (FIG. 5), showing that LPS was being immunostained.

LPS was localized in neurons (FIGS. 6, 7), microglia (FIG. 8), oligodendrocytes and oligodendrocyte progenitor cells (FIGS. 9, 10). LPS co-localized with a nuclear marker, DAPI, in control GM (FIG. 3E) and WM (FIG. 3G) including ependymal cells (FIG. 3G, arrow heads). In AD GM there was LPS staining in what appeared to be amyloid plaques in cortex (FIG. 3B, 3F—white arrow). Smaller LPS stained structures appeared to be nuclei in GM (FIG. 3B, 3F—yellow arrows) and WM (FIG. 3D, 3H). Note that ependymal cells were missing in AD brain (FIG. 3H arrow heads) and DAPI was absent in many nuclei that were stained with LPS in WM (FIG. 3H).

K99 pili protein was associated with neuron-like cells in AD cortex (FIG. 11B) but not in controls (FIG. 11A). K99 pili protein was localized to control ependymal cells (FIG. 11C) that were lost in AD brains (FIG. 11D, arrow heads). K99 pili protein immunostaining of fiber tracts in AD WM (FIG. 11D) was greater than in controls (FIG. 11C).

Association of LPS with Amyloid Plaques in AD Brains.

LPS positively stained clusters were frequently observed in AD brains (FIG. 12, A1, arrow). Within these clusters DNA stained with DAPI from coalesced cells and was indistinct (FIG. 12, A2 and A3, arrows). Moreover, the coalesced DNA co-localized with Aβ1-40/42 (FIG. 12, B1-3, arrows).

LPS and Aβ1-40/42 co-localized in three different patterns in AD brains. (1) Clusters composed mainly of LPS particles co-localized with Aβ31-40/42 (FIG. 13A). (2) Aβ31-40/42 deposits that co-localized with LPS were surrounded by LPS (FIG. 13B, 4C). (3) The most common pattern showed confluent Aβ31-40/42 stained amyloid plaques with scattered LPS particles in them (FIG. 13D).

LPS stained plaques were surrounded by astrocytes (FIG. 14B1-B4, arrows). In AD cortex, LPS was localized in neurons, microglia, oligodendrocytes, and oligodendrocyte progenitor cells (FIG. 14 B1-B4, FIGS. 6-10).

In contrast, K99 pili protein surrounded small Aβ1-40/42 stained amyloid plaques (FIG. 13E, 13F, 13G), but was absent around larger amyloid plaques (diameter >50 μm) (FIG. 13H).

Association of LPS and K99 Pili Protein with Blood Vessels.

In control brains, both LPS (FIG. 15A) and *E. coli* K99 (FIG. 15C) localized to blood vessels that did not stain for Aβ1-40/42 (FIG. 15A, 15C). In contrast, LPS and Aβ1-40/42 co-localized in vessel walls of AD brains (yellow staining, FIG. 15B). Aβ1-40/42 was sandwiched by but did not co-localize with K99 pili protein in vessels in AD brains (FIG. 15D, arrow heads).

*E. coli* DNA in AD and Control Brains.

PCR with primers for the *E. coli* glutamate decarboxylase B gene (gadB) (19) showed the predicted 175 bps DNA fragment which was the same size in control and AD gray matter, as well as in the positive control ATCC 8739 *E. coli* strain (FIG. 16). The 175 bps amplicon was detected in 9/10 normal control (FIG. 16A) and 9/13 AD brains (FIG. 16B). Of these, 1/10 control and 4/13 AD samples showed bands of different sizes (FIG. 16) of unknown significance. All samples showed low molecular weight bands that likely represented primer interactions. A Megablast (optimized for highly similar sequences; NCBI non-redundant nucleotide database) of the DNA sequences (Table 5) of the amplicons from the qPCR reactions showed that DNA from the three human controls (Table 5) was 100% identical to 115 *E. coli* strains/substrains/entries in the database, and to 5 *Shigella* strains. The DNA sequence from one of the AD samples (Table 5) was 100% identical to 7 strains/substrains/entries of *E. coli*, while the DNA from the other AD sample (Table 5) had one nucleotide mismatch from 116 *E. coli* strains/substrains/entries, and one mismatch (99.4% identity) from the same 5 *Shigella* strains as the other AD sample. One AD sample (AD1), negative on quantitative PCR, was also negative upon sequencing.

TABLE 5

Sequencing of PCR products in Alzheimer's disease and control gray matter with primers for the *E. coli* glutamate decarboxylase B gene (gadB)

8739D-5 *E. coli* control (SEQ ID NO: 1)
5'-CACGTTTTGGTGCGAAGTCTATTTCCACTATCGCAGAATCAAAACGT
TTTCCGCTGCACGAAATGCGCGACGATGTCGCATTCCAGATTATCAATGA
CGAATTATATCTTGATGGCAACGCTCGTCAGAACCTGGCCACTTTCTGCC
AGACTTGGGACGACGAAAATGTCCACAA-3'

Human Control 1 (SEQ ID NO: 2)
5'-CACGTTTTGGTGCGAAGTCTATTTCCACTATCGCAGAATCAAAACGT
TTTCCGCTGCACGAAATGCGCGACGATGTCGCATTCCAGATTATCAATGA
CGAATTATATCTTGATGGCAACGCTCGTCAGAACCTGGCCACTTTCTGCC
AGACCTGGGACGACGAAAATGTCCACAA-3'

Human Control 2 (SEQ ID NO: 3)
5'-CACGTTTTGGTGCGAAGTCTATTTCCACTATCGCAGAATCAAAACGT
TTTCCGCTGCACGAAATGCGCGACGATGTCGCATTCCAGATTATCAATGA
CGAATTATATCTTGATGGCAACGCTCGTCAGAACCTGGCCACTTTCTGCC
AGACCTGGGACGACGAAAATGTCCACAA-3'

Human Control 3 (SEQ ID NO: 4)
5'-CACGTTTTGGTGCGAAGTCTATTTCCACTATCGCAGAATCAAAACGT
TTTCCGCTGCACGAAATGCGCGACGATGTCGCATTCCAGATTATCAATGA
CGAATTATATCTTGATGGCAACGCTCGTCAGAACCTGGCCACTTTCTGCC
AGACCTGGGACGACGAAAATGTCCACAA-3'

Human AD2 (SEQ ID NO: 5)
5'-CACGTTTTGGTGCGAAGTCTATTTCCACTATCGCAGAATCAAAACGT
TTTCCGCTGCACGAAATGCGCGACGATGTCGCATTCCAGATTATCAATGA
CGAATTATATCTTGATGGCAACGCTCGTCAGAACCTAGCCACTTTCTGCC
AGACTTGGGACGACGAAAATGTCCACAA-3'

Human AD3 (SEQ ID NO: 6)
5'-CACGTTTTGGTGCGAAGTCTATTTCCACTATCGCAGAATCAAAACGT
TTTCCGCTGCACGAAATGCGCGACGATGTCGCATTCCAGATTATCAATGA
CGAATTATATCTTGATGGCAACGTTCGTCAGAACCTGGCCACTTTCTGCC
AGACCTGGGACGACGAAAATGTCCACAA-3'

DISCUSSION

We demonstrate Gram-negative bacterial LPS, *E. coli* K99 pili protein and DNA in control and AD brain. K99 and LPS levels were greater in AD compared to control brains. Moreover, LPS co-localized with Aβ31-40/42 in amyloid plaques and with A11-40/42 around blood vessels in AD brains. These data are consistent with the conclusion that Gram-negative bacterial molecules are associated with AD pathology.

Though the monoclonal antibodies were raised to *E. coli* molecules, they may not be specific for *E. coli*. PCR showed appropriate size bands for *E. coli* DNA in the majority of AD and control brains. Sequencing the bands showed that though most 100% identical hits were for *E. coli*, there were 100% identical hits for a related Gram-negative family member, *Shigella*, which is due to the sequence homology between the two species. Thus, the data support the presence of proteins and DNA from *E. coli* or Gram negative bacteria related to *E. coli*.

Our findings complement a recent RNAseq study that showed bacterially-encoded 16s RNA sequences in all human brains with Gram negative alpha-Proteobacteria representing over 70% of bacterial sequences (16). The other 30% of bacterial classes varied widely with gamma-Proteobacteria which include *E. coli* being present at <5% of total bacterial transcripts found (16). Thus, our data support this previous study.

A major question arises as to how Gram-negative bacterial LPS, proteins and DNA in this study, and how alpha-Proteobacteria molecules (16) or Gram-positive bacterial peptidoglycan (22, 23) in other studies enter brain? In our LPS/ischemia/hypoxia animal model we showed that LPS increased in rat brain over a period of 3 months after a single intraperitoneal injection that was associated with a parallel increase in IL1β and granzyme B in brain (15). We postulated that IL113 producing monocytes and granzyme B producing cytotoxic T cells and/or Natural Killer cells phagocytized the LPS in the periphery via Toll 4 receptors and carried LPS into brain (15). Gamma Proteobacteria Enterobacteriaceae like *E. coli*, and related family members like *Salmonella* and *Shigella*, cause diarrheal illness in humans (24), and some strains of *E. coli* are resident in the gastrointestinal tract. The virulence of Enterotoxigenic *E. coli* that cause diarrhea are dependent on production of adhesins and enterotoxins, and the *E. coli* K99 pili protein found in control and AD brains is one of the surface antigens in Enterotoxigenic (diarrhea) *E. coli* adhesive pili (25). It is tempting to speculate that this study provides another example of a gut-to-brain connection (26) with gut being one possible source of brain *E. coli* supporting the concept of AD being a systemic disease (27). *E. coli* from urinary tract and other infections could also be a source for brain bacterial molecules. Finally, since LPS derived from Gram-negative bacteria injures the blood brain barrier (28), this could promote entry of LPS and other bacterial molecules into brain.

Previous studies show sporadic late-onset AD can be associated with infection (9-12). Infectious agents previously associated with AD include Spirochetes, *P. gingivalis*, *Borrelia burgdorferi*, *Chlamydophila pneumonia*, *Helicobacter pylori*, *C. glabrata*, various fungi, Herpes viruses and cytomegalovirus (9-12). A major difference between previous studies and this one is that LPS co-localized with amyloid plaque and with peri-vascular amyloid in every AD brain.

LPS is the major component of the outer membrane of Gram-negative bacteria. Gram-negative bacteria include alpha-Proteobacteria found in human brain 16 and include gamma-Proteobacteria like *E. coli*, molecules of which were found in brain in this study. LPS was co-localized with Aβ1-40/42 in amyloid plaques and with peri-vascular Aβ1-40/42 in all AD brains. In our recent animal study, systemic LPS combined with cerebral ischemia/hypoxia produced aggregates of myelin that co-localized with Aβ1-40/42 in adult rat brains and the aggregates had features of amyloid plaques (15). These animal data, combined with the current human brain data, s that LPS in combination with other factors could cause AD neuropathology.

LPS and *E. coli* K99 pili protein in vessels and ependymal cells could contribute to vessel injury (29) and ependymal injury (17) and WM injury observed in AD brains. There was more K99 pili protein in GM and WM of AD brains, and both white and gray matter are consistently damaged in AD (17, 30). However, the current human data cannot determine if the bacterial molecules are a cause or consequence of the injury to AD brain.

There are limitations of this study. *E. coli* could contaminate tissue samples. We used sterile techniques, sterile solutions and sampled the core of frozen tissue blocks to reduce contamination. Evidence against *E. coli* contamination includes the finding that LPS and *E. coli* K99 staining patterns in control and AD brains were different, the staining patterns were consistent in all brains, and levels of K99 and LPS were higher in AD compared to control brains. Studies of brain biopsies obtained during life would help address the possibility of contamination during autopsy, however.

The current study did not test whether there are live bacteria in human brain. However, a recent study found evidence for live bacteria in brain and supports the idea that every organ, including brain, has its own microbiome (16). Since this study focused on *E. coli* proteins and DNA, future studies are needed to address the potential for other bacteria in AD pathogenesis.

REFERENCES

1. Holmes C, Butchart J. Systemic inflammation and Alzheimer's disease. Biochem Soc Trans 2011; 39:898-901.
2. Dunn N, Mullee M, Perry V H, Holmes C. Association between dementia and infectious disease: evidence from a case-control study. Alzheimer Dis Assoc Disord 2005; 19:91-94.
3. Tyas S L, Manfreda J, Strain L A, Montgomery P R. Risk factors for Alzheimer's disease: a population-based, longitudinal study in Manitoba, Canada. Int J Epidemiol 2001; 30:590-597.
4. Verreault R, Laurin D, Lindsay J, De Serres G. Past exposure to vaccines and subsequent risk of Alzheimer's disease. CMAJ 2001; 165:1495-1498.
5. Engelhart M J, Geerlings M I, Meijer J, et al. Inflammatory proteins in plasma and the risk of dementia: the Rotterdam study. Arch Neurol 2004; 61:668-672.
6. Schmidt R, Schmidt H, Curb J D, Masaki K, White L R, Launer L J. Early inflammation and dementia: a 25-year follow-up of the Honolulu-Asia Aging Study. Ann Neurol 2002; 52:168-174.
7. Imbimbo B P. An update on the efficacy of non-steroidal anti-inflammatory drugs in Alzheimer's disease. Expert Opin Investig Drugs 2009; 18:1147-1168.
8. Vlad S C, Miller D R, Kowall N W, Felson D T. Protective effects of NSAIDs on the development of Alzheimer disease. Neurology 2008; 70:1672-1677.
9. Bibi F, Yasir M, Sohrab S S, et al. Link between chronic bacterial inflammation and Alzheimer disease. CNS Neurol Disord Drug Targets 2014; 13:1140-1147.
10. Singhrao S K, Harding A, Poole S, Kesavalu L, Crean S. *Porphyromonas gingivalis* Periodontal Infection and Its Putative Links with Alzheimer's Disease. Mediators of inflammation 2015; 2015:137357.
11. Noble J M, Scarmeas N, Celenti R S, et al. Serum IgG antibody levels to periodontal microbiota are associated with incident Alzheimer disease. PLoS One 2014; 9:e114959.
12. Civitelli L, Marcocci M E, Celestino I, et al. Herpes simplex virus type 1 infection in neurons leads to production and nuclear localization of APP intracellular domain (AICD): implications for Alzheimer's disease pathogenesis. J Neurovirol 2015.
13. Chapman M R, Robinson L S, Pinkner J S, et al. Role of *Escherichia coli* curli operons in directing amyloid fiber formation. Science 2002; 295:851-855.
14. Fowler D M, Koulov A V, Balch W E, Kelly J W. Functional amyloid—from bacteria to humans. Trends Biochem Sci 2007; 32:217-224.
15. Zhan X, Cox C, Ander B P, et al. Inflammation Combined with Ischemia Produces Myelin Injury and Plaque-Like Aggregates of Myelin, Amyloid-beta and AbetaPP in Adult Rat Brain. J Alzheimers Dis 2015; 46:507-523.
16. Branton W G, Ellestad K K, Maingat F, et al. Brain microbial populations in HIV/AIDS: alpha-proteobacteria predominate independent of host immune status. PLoS One 2013; 8:e54673.
17. Zhan X, Jickling G C, Ander B P, et al. Myelin injury and degraded myelin vesicles in Alzheimer's disease. Curr Alzheimer Res 2014; 11:232-238.
18. Zhan X, Jickling G C, Ander B P, et al. Myelin basic protein associates with AbetaPP, Abeta1-42, and amyloid plaques in cortex of Alzheimer's disease brain. J Alzheimers Dis 2015; 44:1213-1229.
19. Quinones B, Swimley M S, Narm K E, Patel R N, Cooley M B, Mandrell R E. O-antigen and virulence profiling of shiga toxin-producing *Escherichia coli* by a rapid and cost-effective DNA microarray colorimetric method. Frontiers in cellular and infection microbiology 2012; 2:61.
20. Braak H, Braak E. Frequency of stages of Alzheimer-related lesions in different age categories. Neurobiol Aging 1997; 18:351-357.
21. Klemm P, Schembri M A. Bacterial adhesins: function and structure. International journal of medical microbiology: IJMM 2000; 290:27-35.
22. Schrijver I A, van Meurs M, Melief M J, et al. Bacterial peptidoglycan and immune reactivity in the central nervous system in multiple sclerosis. Brain 2001; 124:1544-1554.
23. Visser L, Melief M J, van Riel D, et al. Phagocytes containing a disease-promoting Toll-like receptor/Nod ligand are present in the brain during demyelinating disease in primates. Am J Pathol 2006; 169:1671-1685.
24. Fischer Walker C L, Sack D, Black R E. Etiology of diarrhea in older children, adolescents and adults: a systematic review. PLoS neglected tropical diseases 2010; 4:e768.
25. Nagy B, Fekete P Z. Enterotoxigenic *Escherichia coli* (ETEC) in farm animals. Vet Res 1999; 30:259-284.
26. Schmidt C. Mental health: thinking from the gut. Nature 2015; 518:S12-15.
27. Khan T K, Alkon D L. Peripheral biomarkers of Alzheimer's disease. J Alzheimers Dis 2015; 44:729-744.
28. Erickson M A, Hartvigson P E, Morofuji Y, Owen J B, Butterfield D A, Banks W A. Lipopolysaccharide impairs amyloid beta efflux from brain: altered vascular sequestration, cerebrospinal fluid reabsorption, peripheral clearance and transporter function at the blood-brain barrier. J Neuroinflammation 2012; 9:150.
29. Janota C, Lemere C A, Brito M A. Dissecting the Contribution of Vascular Alterations and Aging to Alzheimer's Disease. Mol Neurobiol 2015.
30. Bartzokis G, Sultzer D, Lu P H, Nuechterlein K H, Mintz J, Cummings J L. Heterogeneous age-related breakdown of white matter structural integrity: implications for cortical "disconnection" in aging and Alzheimer's disease. Neurobiol Aging 2004; 25:843-851.

Example 2

Detection of Additional Gram-Negative Bacteria Biomarkers in Control and AD Human Brains Methods Western Blot Analysis.

Tissue was homogenized in cold RIPA buffer containing a protease inhibitor mixture. After centrifuging homogenates for 30 min at 4° C. (14,000 g), the pellet was discarded and proteins in the supernatant separated on 10% SDS polyacrylamide gels. They were then transferred to nitrocellulose membranes and hybridized overnight at 4° C. with primary antibodies listed below. Antibodies were stained using horseradish peroxidase-conjugated anti-rabbit or anti-mouse IgG (Bio-Rad) combined with ECL chemiluminescent detection (PIERS). Primary antibodies were obtained from Lifespan (CAT, LS-C153970; GrpE, LS-C66627; TetR, LS-C49339; 3 gal, LS-C63430) and Millipore (ALK, MAB1012).

Results

Control samples (n=3) and AD samples (n=3) including gray matter (GM) and white matter (WM) were assessed for E. coli GrpE, CAT (Chloramphenicol Acetyltransferase), TetR (Tet Repressor Protein), ALK (Alkaline Phosphatase), and 1 gal (β-Galactosidase) using Western blot analysis.

Detection of E. coli GrpE in AD and Control Brains.

Figure 17:
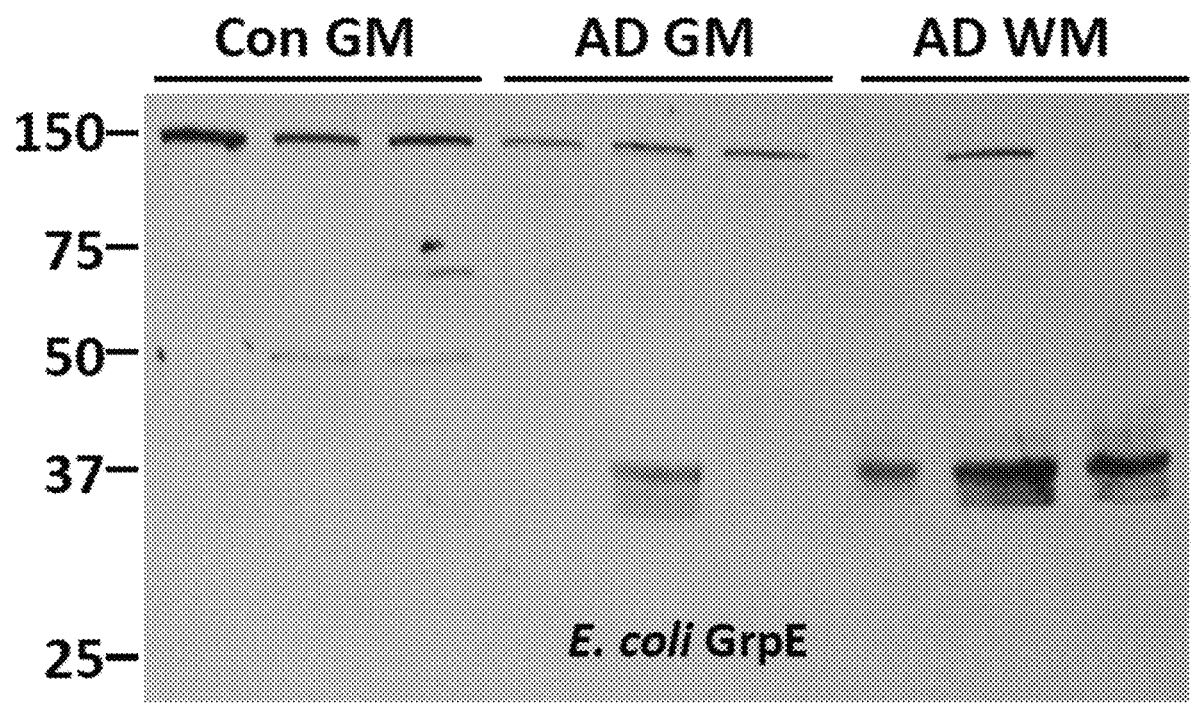
FIG. 17 illustrates Western blot analysis of *E. coli* GrpE in human brains. Anti-GrpE antibody detected a large band at 150 kDa, two medium bands at 70 kDa and 50 kDa respectively, and a small band at 37 kDa. Large band of 150 kDa was common in control (3/3 control GM) and AD (3/3 AD GM, 2/3 AD WM). Medium bands at 70 kDa (1/3 control GM) and 50 kDa (2/3 control GM) were specific to control and small band at 37 kDa was specific to AD (1/3 AD GM, 3/3 AD WM). Con=control, GM=gray matter, WM=white matter, AD=Alzheimer's disease.

Anti-GrpE antibody detected a large band at 150 kDa, two medium bands at 70 kDa and 50 kDa respectively, and a small band at 37 kDa (FIG. 17). Large band of 150 kDa was common in control (3/3 control GM) and AD (3/3 AD GM, 2/3 AD WM). Medium bands at 70 kDa (1/3 control GM) and 50 kDa (2/3 control GM) were specific to control and small band at 37 kDa was specific to AD (1/3 AD GM, 3/3 AD WM) (FIG. 17).

Detection of E. coli CAT in AD and Control Brains.

Figure 18:
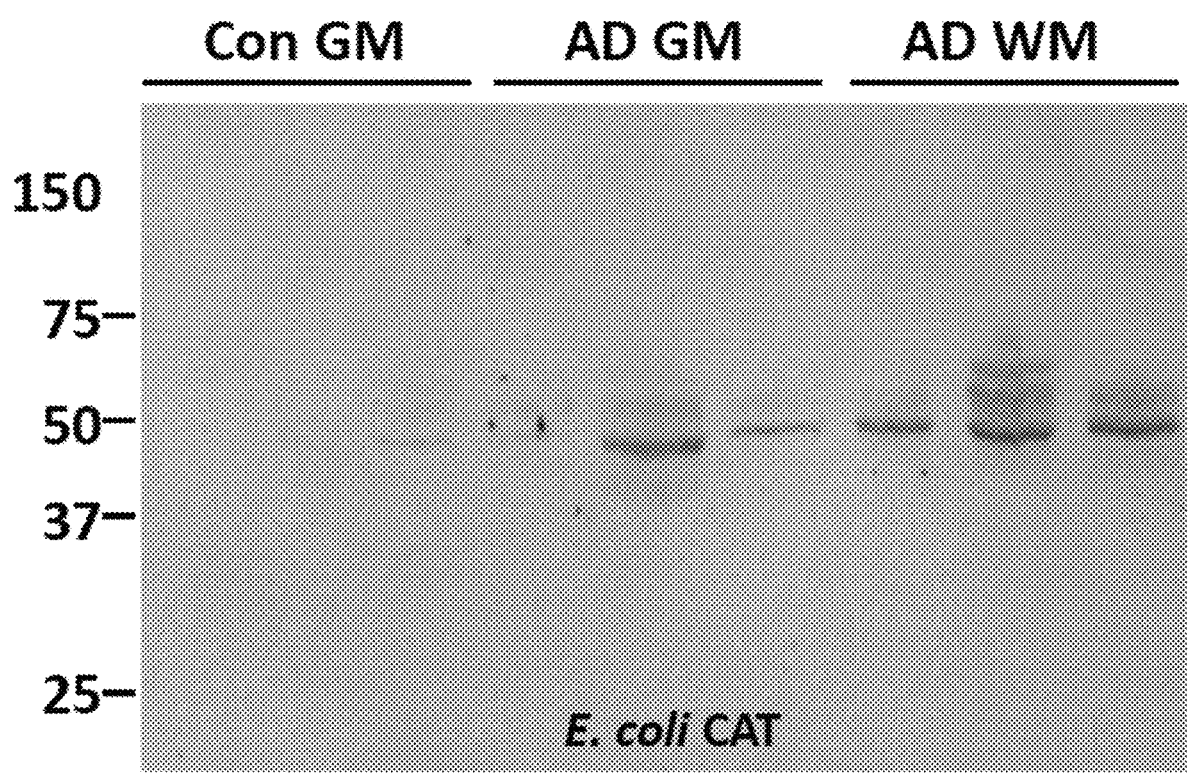
FIG. 18 illustrates Western blot analysis of *E. coli* CAT in human brains. Anti-CAT antibody detected a ladder pattern of bands around 50 kDa. These bands were detected in 3/3 AD GM, 3/3 AD WM and 1/3 control GM. CAT=Chloramphenicol Acetyltransferase, Con=control, GM=gray matter, WM=white matter, AD=Alzheimer's disease.

Anti-CAT antibody detected a ladder pattern of bands around 50 kDa (FIG. 18). These bands were detected in 3/3 AD GM, 3/3 AD WM and 1/3 control GM (FIG. 18).

Detection of E. coli TetR in AD and Control Brains.

Figure 19:
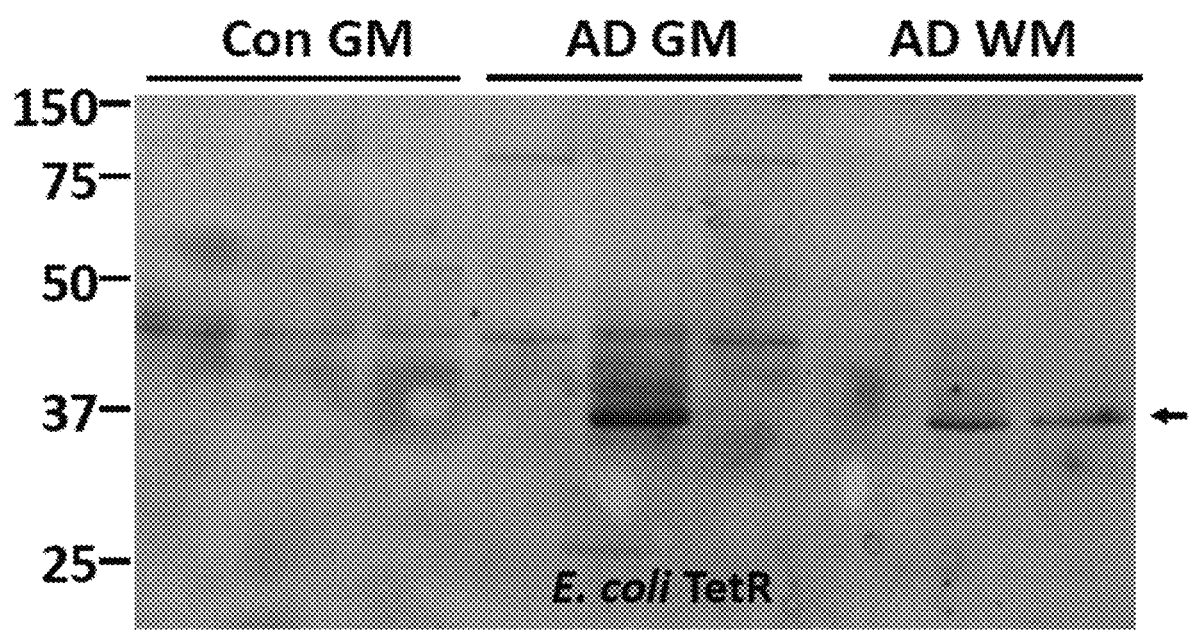
FIG. 19 illustrates Western blot analysis of *E. coli* TetR in human brains. Anti-TetR antibody detected a large band around 100 kDa, medium bands from 40 kDa to 60 kDa in control and AD brains and a small band at 37 kDa. Large band of 100 kDa was common in control GM (3/3 control GM) and AD GM (3/3 AD GM) but not in AD WM (0/3 AD WM). Medium bands were common in control GM (3/3 control GM), AD GM (3/3 AD GM) and AD WM (2/3 AD WM). Small band was specific to AD (1/3 AD GM, 2/3 AD WM). TetR=Tet Repressor Protein, Con=control, GM=gray matter, WM=white matter, AD=Alzheimer's disease.

Anti-TetR antibody detected a large band around 100 kDa, medium bands from 40 kDa to 60 kDa in control and AD brains and a small band at 37 kDa (FIG. 19). Large band of 100 kDa was common in control GM (3/3 control GM) and AD GM (3/3 AD GM) but not in AD WM (0/3 AD WM). Medium bands were common in control GM (3/3 control GM), AD GM (3/3 AD GM) and AD WM (2/3 AD WM). Small band was specific to AD (1/3 AD GM, 2/3 AD WM) (FIG. 19).

Detection of E. coli ALK in AD and Control Brains.

Figure 20:
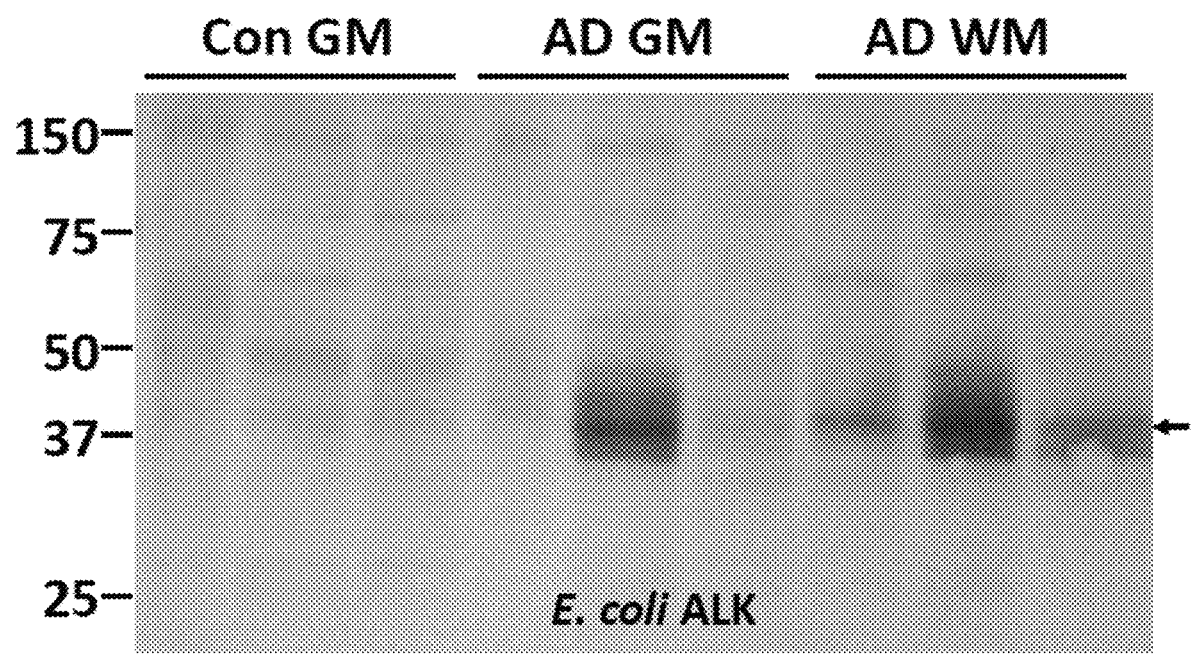
FIG. 20 illustrates Western blot analysis of *E. coli* ALK in human brains. Anti-ALK antibody detected multiple bands from 37 kDa to 150 kDa. Only band at 37 kDa was specific to AD (0/3 control GM, 1/3 AD GM, 3/3 AD WM). ALK=Alkaline Phosphatase, Con=control, GM=gray matter, WM=white matter, AD=Alzheimer's disease.

Anti-ALK antibody detected multiple bands from 37 kDa to 150 kDa (FIG. 20). Only band at 37 kDa was specific to AD (0/3 control GM, 1/3 AD GM, 3/3 AD WM) (FIG. 20).

Detection of E. coli β Gal in AD and Control Brains.

Figure 21:
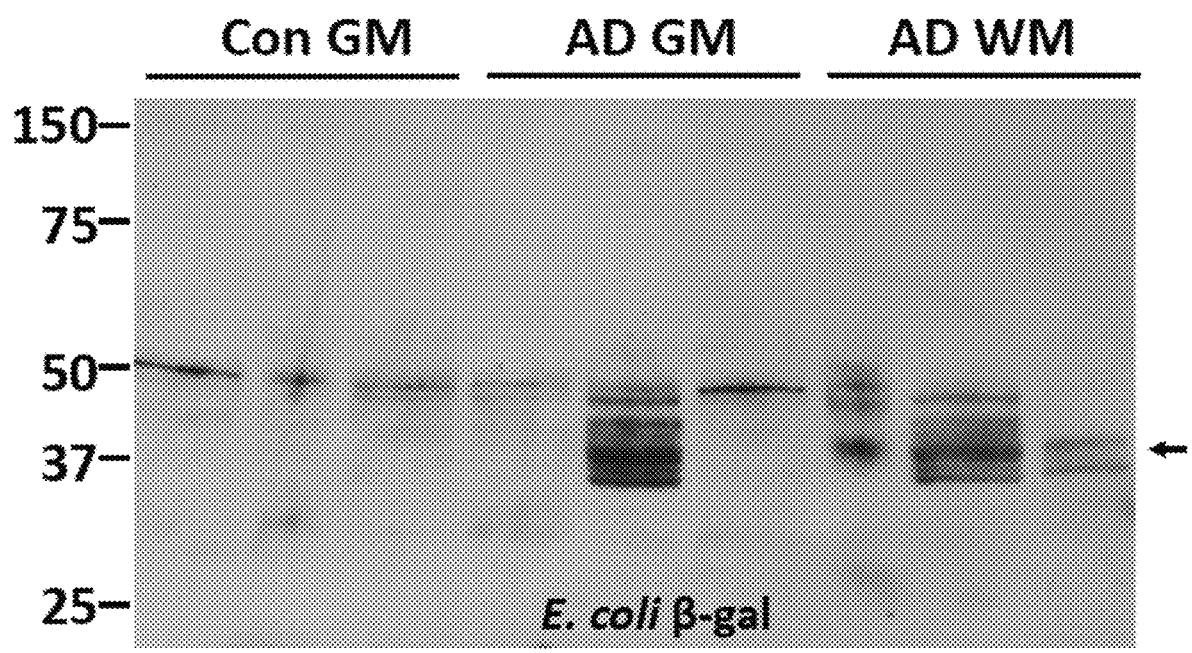
FIG. 21 illustrates Western blot analysis of *E. coli* β gal in human brains. Anti-β gal antibody detected a ladder pattern of bands from 30 kDa and 50 kDa in control and AD brains. Large band at 50 kDa was detected in 3/3 control GM, 3/3 AD GM, and 2/3 AD WM. Ladder pattern of bands around 37 kDa was specific to AD (0/3 in control, 1/3 AD GM, 3/3 AD WM). β gal=β-Galactosidase, Con=control, GM=gray matter, WM=white matter, AD=Alzheimer's disease.

Anti-β gal antibody detected a ladder pattern of bands from 30 kDa and 50 kDa in control and AD brains (FIG. 21). Large band at 50 kDa was detected in 3/3 control GM, 3/3 AD GM, and 2/3 AD WM. Ladder pattern of bands around 37 kDa was specific to AD (0/3 in control, 1/3 AD GM, 3/3 AD WM) (FIG. 21).

Example 3

Specific E. coli Strains in Human AD Brains Compared to Control Brains

We explored whether there are specific E. coli strains in AD compared to control brains. Since the antibody that we used for E. coli LPS studies is raised from E. coli J5 and the level of E. coli LPS distinguishes AD from control, we then targeted DNA coding LPS of E. coli J5 and related Gram negative bacterial strains.

Methods

PCR and DNA Sequencing.

E. coli DNA was detected using PCR amplification of an LPS GalT-GalE-MODF DNA fragment. This DNA fragment was selected because the PCR product detects LPS containing Gram negative bacteria including E. coli J5 that lacks the GalE gene. All reagents used for PCR were first tested for E. coli DNA contamination which is indicated by detection of E. coli DNA in endotoxin free water. Only those reagents which are free of E. coli DNA were used for PCR amplification in human brains. E. coli DNA from the J5, 0111:B4 and K12 are used as positive controls. DNA primers used in this study for PCR amplification and DNA sequencing were forward sequence (5'→3') CAGAATCCATTGCCCGGTGA and reverse sequence (5'→3') CCATGTCACACTTTTCG-CATCT (Eurofins MWG). PCR amplification was performed following standard protocols described in our recent publication (Zhan et al., Neurology (2016) 87:2324-2332). Identification of the GalT-GalE-MODF genes is confirmed by a 3' and 5' Sanger DNA sequencing assay on 20 control brains, 60 AD brains, E. coli J5, 0111:B4 and K12 strains at the UC Davis DNA Sequencing Facility where we have sequenced E. coli/bacterial DNA in AD and control before (Zhan et al., Neurology (2016) 87:2324-2332). DNA data are analyzed with ABI Prism® 3730 Genetic Analyzer, ABI Prism® 3730 Data Collection Software v. 3.0, and ABI Prism® DNA Sequencing Analysis Software v. 5.2.

Results

Figure 22:
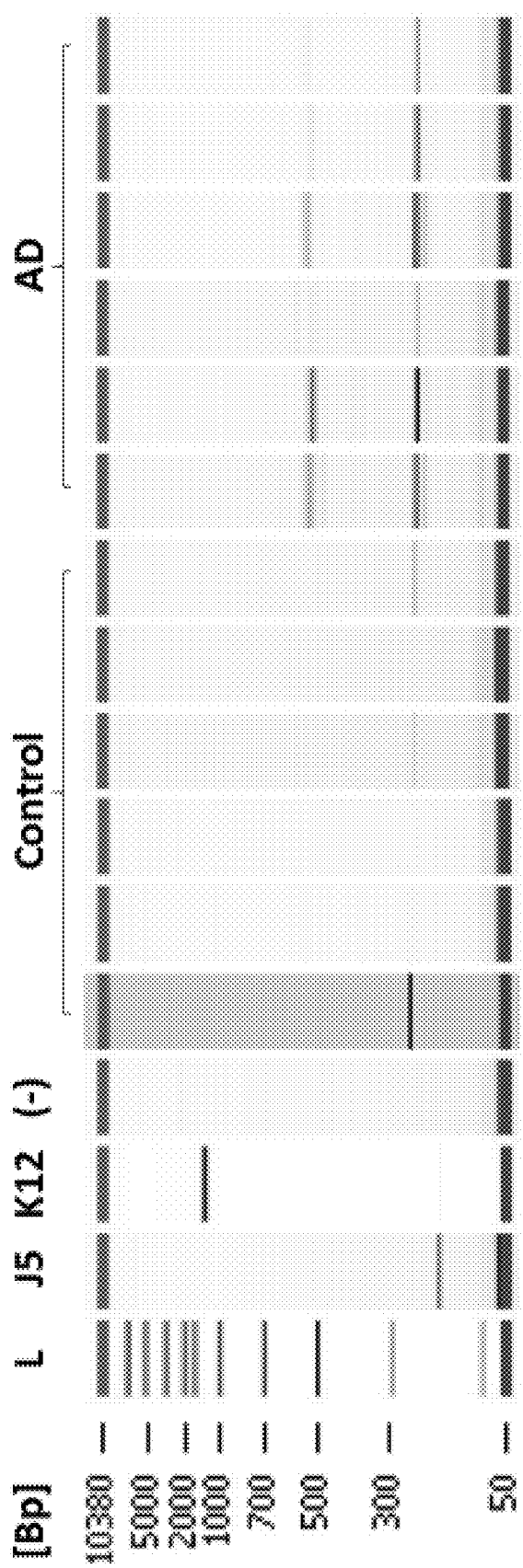
FIG. 22 illustrates PCR results of GalE-GalT-MODF DNA fragments. PCR product is about 200 bps for J5 and 1300 bps for K12, respectively. In human brains, a 250 bps PCR product is detected in 3/6 control and 6/6 AD brains; a 500 bps PCR product is detected in 5/6 AD brains and 0/6 control brains. These data are consistent with the conclusion that the 500 bps product is specific to AD.

LPS are large molecules consisting of a lipid and a polysaccharide composed of core oligosaccharide and O antigen (or O polysaccharide). It is O antigen that determines the strain of Gram negative bacteria (DebRoy, et al., *Anim Health Res Rev* 2011; 12:169-185). The presence or absence of O antigen determines whether the LPS is considered rough or smooth. Full-length O antigen would render the LPS smooth, whereas the absence or reduction of O antigen would make LPS rough. E. coli J5 is a UDP-galactose-4-epimerase (galE) rough mutant of E. coli O111:B460. As a result, it cannot use galactose to synthesize complete LPS and its LPS lacks a side chain of O antigen. In E. coli, the GalE gene encodes UDP-galactose-4-epimerase and the neighbor genes of GalE are galactose-1-phosphate uridylyltransferase (GalT) and molybdate ABC transporter ATP-binding protein (modF). We designed primers with the product spanning GalT, GalE and modF genes. Since E. coli J5 lacks the GalE gene, we identified a short PCR product from E. coli J5 compared to GalE contained E. coli strain such as E. coli K12. Indeed, the PCR product was about 200 bps for J5 and 1300 bps for K12, respectively (FIG. 22). In human brains, a 250 bps PCR product was detected in 3/6 control brains and 6/6 AD brains; a 500 bps PCR product was detected in 5/6 AD brains and 0/6 control brains. These data are consistent with the conclusion that the 500 bps product is specific to AD (FIG. 22). The 500 bps PCR product may also be useful for providing a prognosis or staging AD. A higher frequency of E. coli GalT-GalE-modF 500 bps DNA fragments may be detectable in AD brains with more severe pathology in the late stage of AD such as Braak & Braak stage V/VI compared to those in early stage such as Braak & Braak stage I/II. DNA sequencing of these products can confirm E. coli GalT-GalE-modF DNA in human brains and be used to identify E. coli strains specific to AD. DNA sequencing can be used to demonstrate how these DNA fragments detected in AD brains associate with specific E. coli strains. Neither J5 nor K12 DNA was found in control or AD brains.

It is understood that the examples and embodiments described herein are for illustrative purposes only and that various modifications or changes in light thereof are suggested to persons skilled in the art and are to be included within the spirit and purview of this application and scope of the appended claims. All publications, patents, and patent applications cited herein are hereby incorporated by reference in their entirety for all purposes.

---

What is claimed is:

1. A method of determining whether gram-negative bacteria molecules are co-localized with amyloid plaques in a subject exhibiting one or more symptoms associated with cognitive impairment associated with amyloid deposits in the brain, comprising determining in a central nervous system (CNS) sample from the subject the presence of gram-negative bacteria; and positively identifying the presence of gram-negative bacteria in the sample as indicative of gram-negative bacteria molecules co-localized with amyloid plaques in the subject, wherein positively identifying the presence of gram-negative bacteria in the sample comprises detecting the presence of E. coli K99 pili protein and the level of E. coli K99 pili protein is significantly greater in the sample from the subject exhibiting one or more symptoms associated with cognitive impairment associated with amyloid deposits in the brain than in a control CNS sample.

2. The method of claim 1, further comprising determining the presence of one or more gram-negative bacteria biomarkers selected from the group consisting of Gram-negative lipopolysaccharide (LPS), E. coli J5 LPS, Gram-negative GrpE, Gram-negative CAT (Chloramphenicol Acetyltransferase), Gram-negative TetR (Tet Repressor Protein), Gram-negative ALK (Alkaline Phosphatase), and Gram-negative β gal (β-Galactosidase) in the samples.

3. The method of claim 2, wherein the level of Gram-negative lipopolysaccharide (LPS) is greater in the CNS sample from the subject exhibiting one or more symptoms associated with cognitive impairment associated with amyloid deposits in the brain than in the control CNS sample.

4. The method of claim 2, wherein the gram-negative LPS co-localizes with Aβ1-40/42 in amyloid deposits and around blood vessels in the CNS sample from the subject.

5. The method of claim 1, wherein the presence of one or more gram-negative bacteria are identified by detecting in the sample from the subject an approximately 500 bp PCR product of bacterial galactose-1-phosphate uridylyltransferase (GalT)—UDP-galactose-4-epimerase (GalE)—molybdate ABC transporter ATP-binding protein (modF) DNA amplified using forward primer (5'→3') CAGAATCCAT-TGCCCGGTGA and reverse sequence (5'→3') CCATGT-CACACTTTTCGCATCT.

6. The method of claim 1, wherein the gram-negative bacteria are E. coli.

7. The method of claim 1, wherein the subject has mild cognitive impairment.

8. The method of claim 1, wherein the subject has Alzheimer's Disease.

9. The method of claim 1, wherein the subject is human.

10. The method of claim 1, wherein the subject is at risk of developing Alzheimer's disease.

11. The method of claim 1, wherein the subject exhibits or has exhibited olfactory impairment in an olfactory challenge test.

12. The method of claim 1, wherein the subject has a familial risk for having Alzheimer's disease.

13. The method of claim 1, wherein the subject has a familial Alzheimer's disease (FAD) mutation.

14. The method of claim 1, wherein the subject is free of and does not have genetic risk factors of Parkinson's disease or schizophrenia.

15. The method of claim 1, wherein the subject is not diagnosed as having or at risk for Parkinson's disease or schizophrenia.

16. The method of claim 1, wherein the subject does not have a neurological disease or disorder other than Alzheimer's disease.

17. The method of claim 1, wherein the subject is not diagnosed as having or at risk for a neurological disease or disorder other than Alzheimer's disease.

18. The method of claim 1, wherein the CNS samples are cerebral spinal fluid (CSF) samples.

19. The method of claim 1, wherein the CNS samples are brain tissue samples.

20. The method of claim 19, wherein the brain tissue samples are superior temporal gyrus gray matter (GM) samples and/or frontal lobe white matter (WM) samples.

21. The method of claim 19, wherein the E. coli K99 pili protein co-localizes to neuron-like cells in the brain tissue sample from the subject exhibiting one or more symptoms associated with cognitive impairment associated with amyloid deposits in the brain.

* * * * *